(12) United States Patent
Ramadan et al.

(10) Patent No.: US 12,270,016 B1
(45) Date of Patent: Apr. 8, 2025

(54) STRUCTURE AND FUNCTION OF MODULAR MICROFLUIDIC DEVICE FOR IN-VITRO MODELING OF HUMAN ORGANS

(71) Applicant: Alfaisal University, Riyadh (SA)

(72) Inventors: Qasem Ramadan, Riyadh (SA); Mohammed Zourob, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 18/815,181

(22) Filed: Aug. 26, 2024

(51) Int. Cl.
| | |
|---|---|
| *C12M 3/00* | (2006.01) |
| *C12M 1/00* | (2006.01) |
| *C12M 1/12* | (2006.01) |
| *C12M 1/34* | (2006.01) |
| *C12M 3/06* | (2006.01) |

(52) U.S. Cl.
CPC .......... *C12M 21/08* (2013.01); *C12M 23/16* (2013.01); *C12M 23/22* (2013.01); *C12M 23/34* (2013.01); *C12M 25/02* (2013.01); *C12M 29/14* (2013.01); *C12M 41/36* (2013.01)

(58) Field of Classification Search
CPC ........ C12M 1/08; C12M 23/16; C12M 23/22; C12M 23/34; C12M 25/02; C12M 25/16; C12M 29/14; C12M 41/36; C12N 5/0693; C12N 2531/00; C12Q 1/6886; C12Q 2600/136; C12Q 2600/158; C07K 2317/24; C07K 2317/76; C07K 16/2863; A61K 31/192; A61K 45/06; A61K 39/3955
See application file for complete search history.

(56) References Cited

U.S. PATENT DOCUMENTS

2013/0143230 A1* 6/2013 Tolias ............... C12Q 1/025
                                                    435/7.1
2015/0299631 A1* 10/2015 Prabhakarpandian ......
                                                    C12M 21/08
                                                    435/29

* cited by examiner

*Primary Examiner* — Michael L Hobbs
(74) *Attorney, Agent, or Firm* — Geeta Kadambi; RIDDHI IP LLC

(57) ABSTRACT

A method and system to make a modular microfluidic device in a miniaturized form for cell culture, co-culture, and organ-on-a-microfluidic device as in-vitro model of human organs within compartmentalized 3D structures is described. The modular microfluidic device enables co-culturing of heterogeneous cell assemblies that are adjacent or sequentially connected to promote enhanced cell-cell interaction. In vivo-like flow into and/or from one cell growth chamber to adjacent cell growth chamber is maintained by micro-engineered porous barriers i.e., porous walls and membranes. These porous barriers provide a tool for mimicking the paracrine exchange between cells in the human body. The system comprises of a set of microelectrodes for real-time and long-term monitoring and quantitative measurement of the impact of stimuli on the epithelial tissue permeability. The modular microfluidic system provides a platform technology for bio-fabrication of variety of miniaturized in-vitro models for mimicking the structure and function of single and multi-organ models.

20 Claims, 52 Drawing Sheets

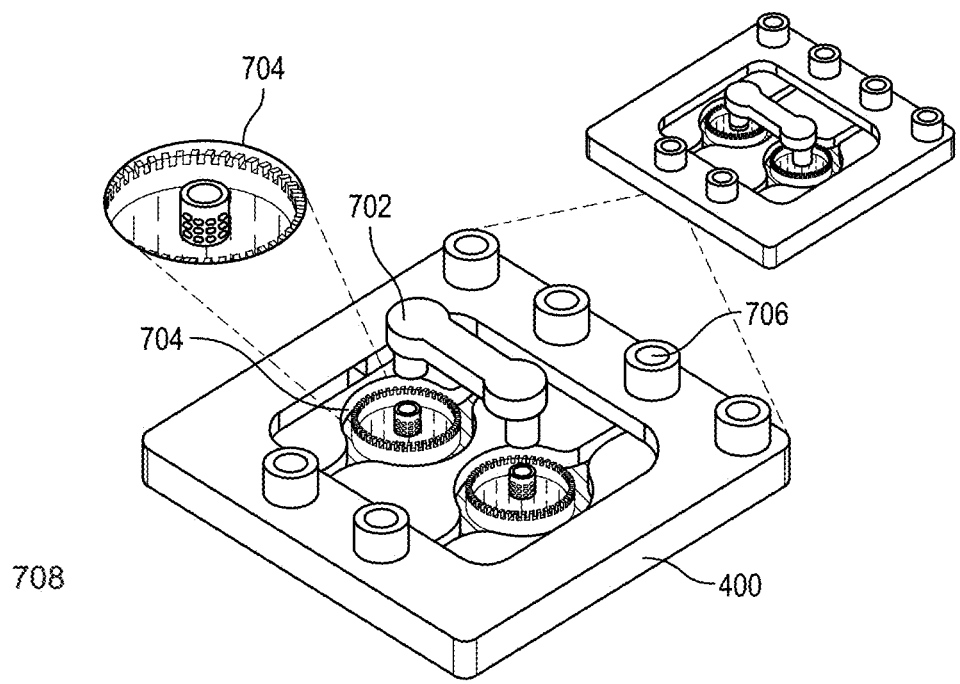
FIG. 7(a)
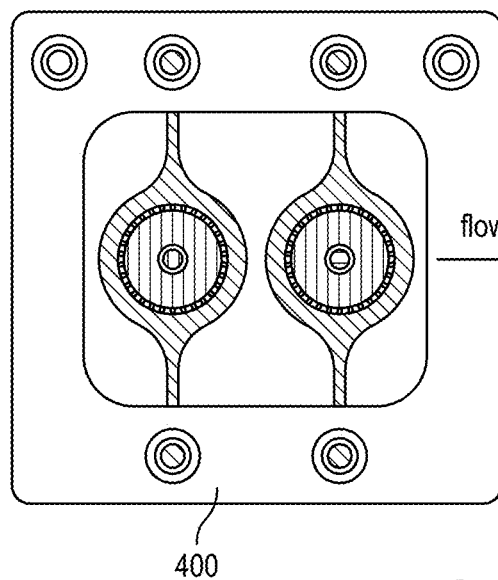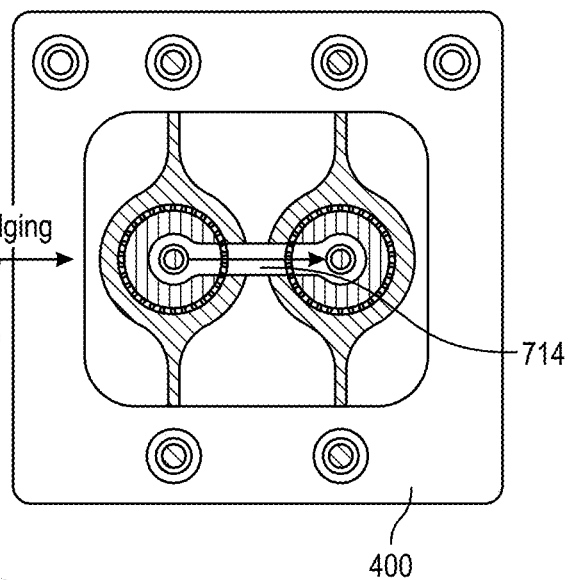
FIG. 7(b)

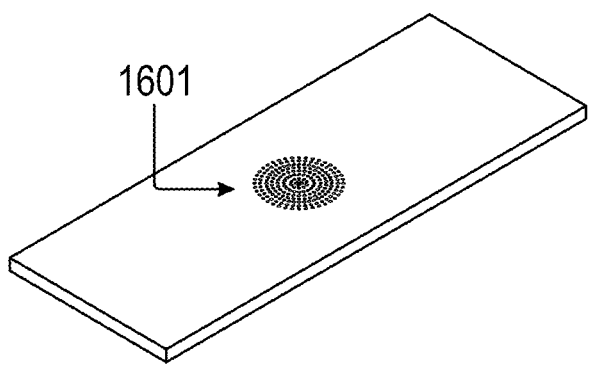
(i)
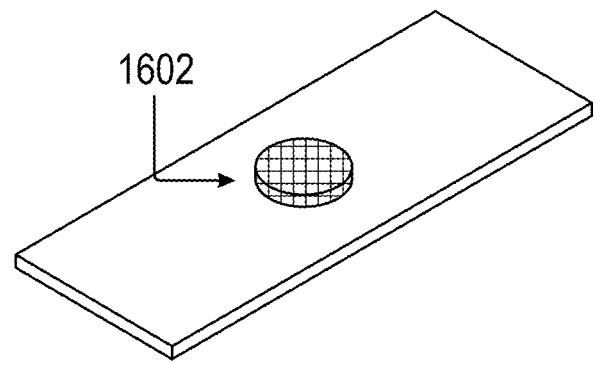
(ii)
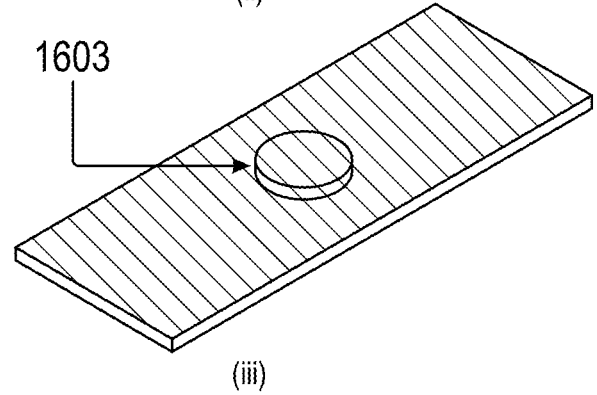
(iii)
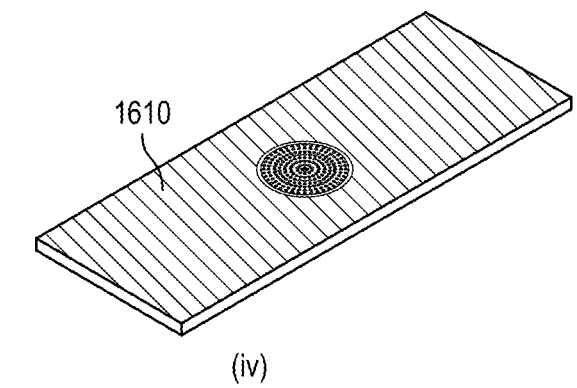
(iv)
FIG. 16(a)

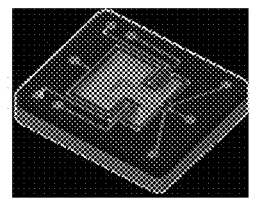
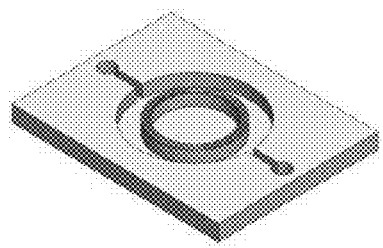
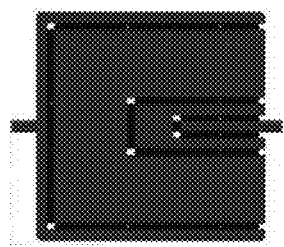
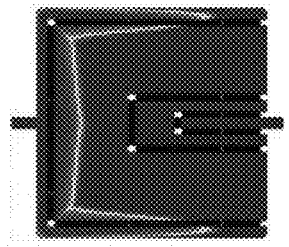
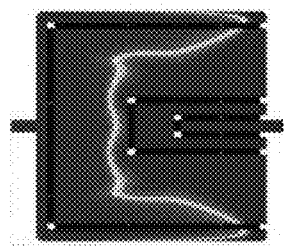
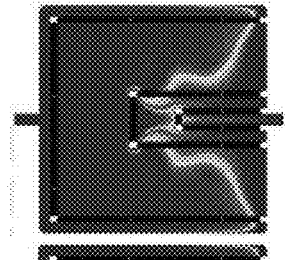
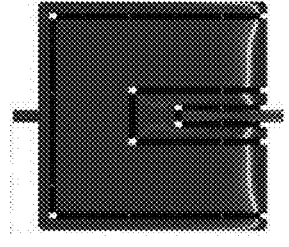
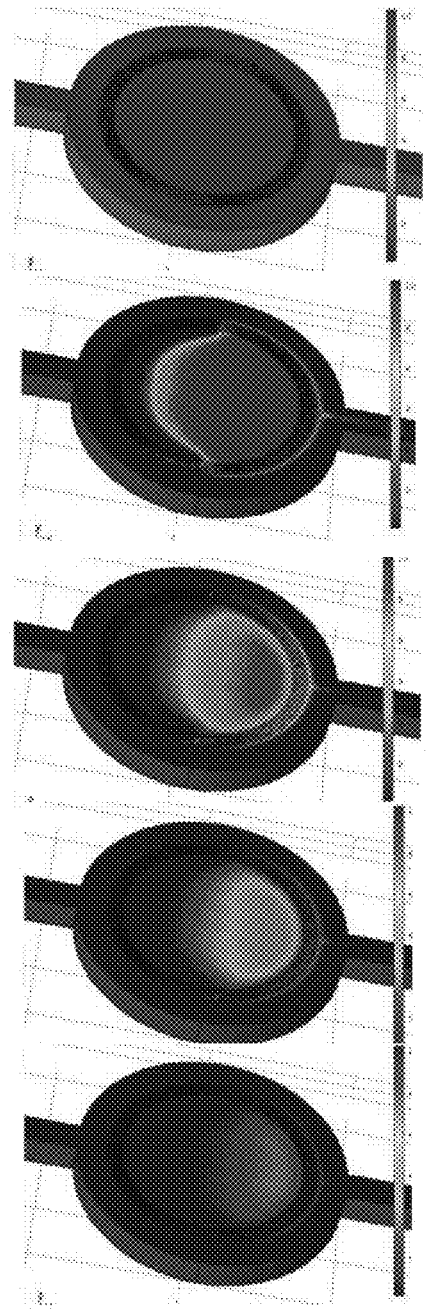
FIG. 18(a)                                    FIG. 18(b)

3D design

The fabricated chip

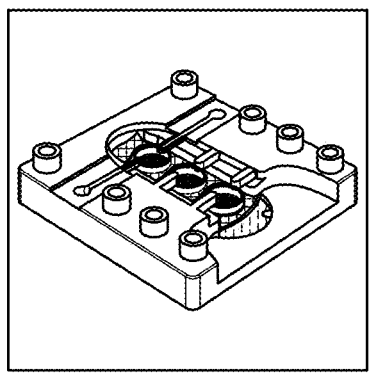
FIG. 28(a)
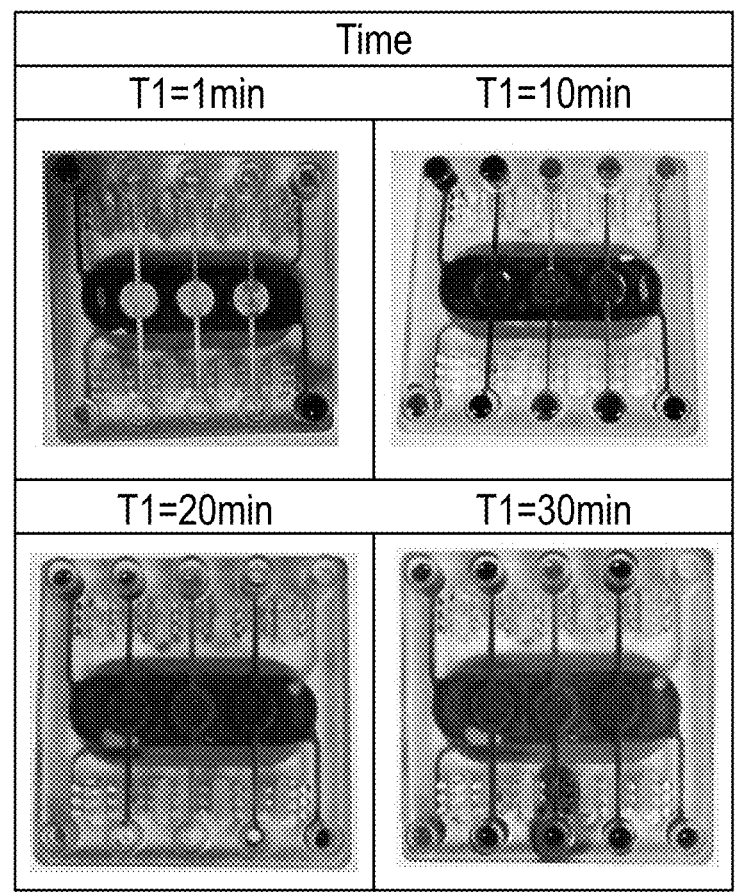
FIG. 28(b)  FIG. 28(c)

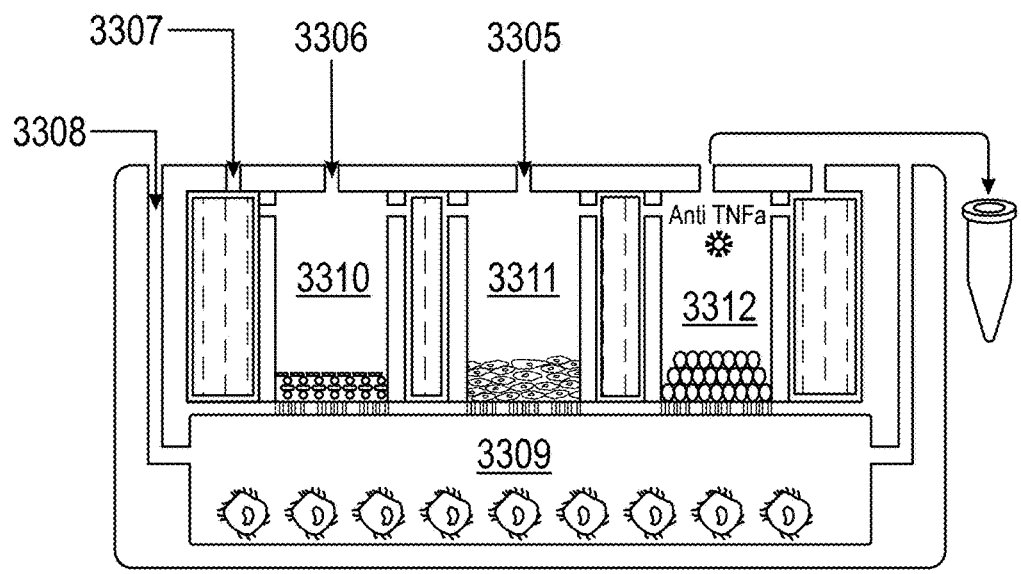
FIG. 33(b)
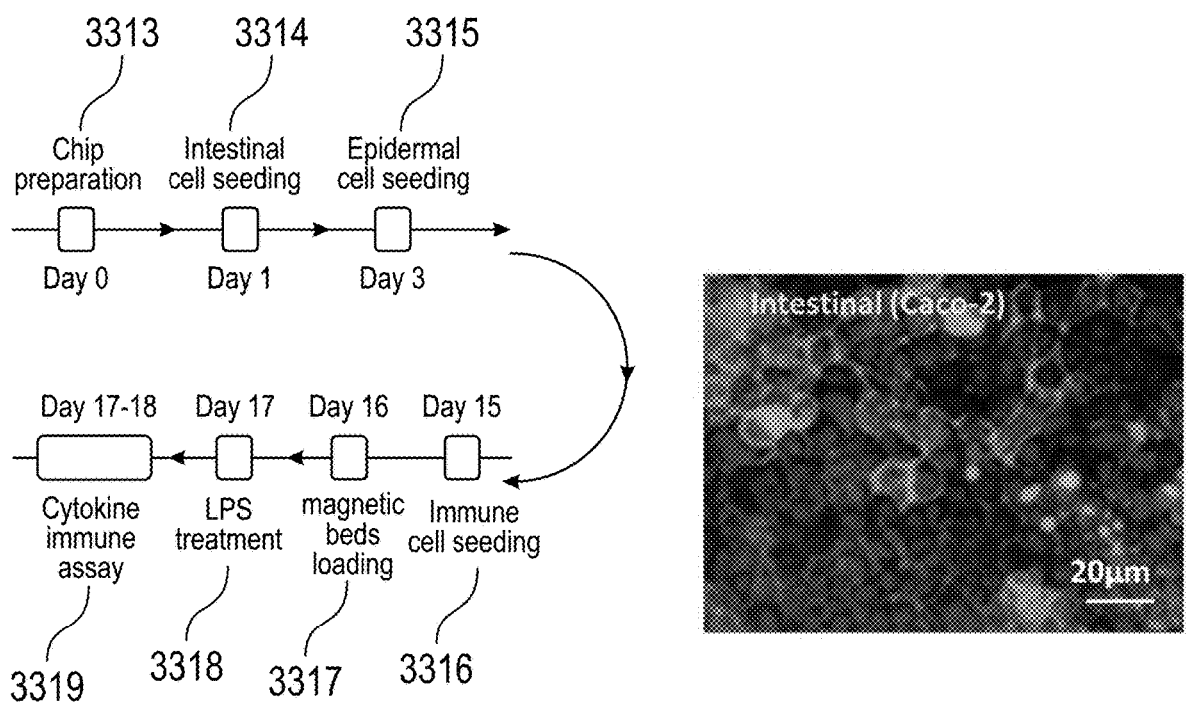
FIG. 33(c)          FIG. 33(d)

STRUCTURE AND FUNCTION OF MODULAR MICROFLUIDIC DEVICE FOR IN-VITRO MODELING OF HUMAN ORGANS

FIELD OF INVENTION

A microfluidic device and system for cell culture, co-culture, and organ-on-a-chip (multi organ cell co-culturing) as in-vitro modeling of human organs within compartmentalized 3D structures is described.

BACKGROUND

Significant research effort and attention are currently focusing on finding methods to transform drug screening and toxicity testing from a system reliant on animal studies to one based primarily on human-relevant in vitro models. In line with regulatory developments precluding the use of animal testing, as well as fundamental differences in animal versus human, human in vitro methodologies are required to replace the animal-based testes while permitting equivalent or superior prediction. Despite much effort, sufficiently acceptable in vitro approaches have not been developed to date, hence the major gap to predict drug response in human still exists. Current in vitro drug screening tools are static and include a limited number of simulated parameters. Furthermore, these in vitro studies use a single cell type to study the drug effect and toxicity. However, these cellular models do not reflect the in vivo multi-cellular structure and consequently do not allow the study of complex interactions under pathophysiological conditions over long periods. Using these methods requires a large number of cells, reagents and culture media, which makes this a rather expensive approach. Furthermore, they are less suited to provide a dynamically controlled cell microenvironment, therefore, provide only little physiological relevance. There is consequently a real need for in vitro models of the human involved organs that closely mimic the physiological processes of disease development with an acceptable level of flexibility, accuracy, and reproducibility for efficient screening of potential drug candidates.

SUMMARY

A modular microfluidic device having various permutations and combination of cellular growth compartment, fluidic channels, and different types of membranes between and below these compartments, that control the flow is created using fabrication and/or 3D printing is described. In one embodiment, a method of making a modular microfluidic device is done by layering a top and a bottom layer of the modular microfluidic device with a transparent material is described. A porous membrane is fabricated between the top and bottom layer to form a cell growth compartment. A compartmentalized fluidic system is created to enable the co-culture of different cell types; and semi porous walls (SPWs) are created around the cell growth compartments to contain a growth media for a different type of cells and enable the exchange of bio/chemical signals between the cells to mimic the human body system.

In another embodiment, a multi-cell growth compartment is created with a combination of planar and vertical organization interfaced with a planar and a vertical porous barrier. The cell growth compartment is configured as one of a parallel, horizontal, sequential design in relation to each other. Connecting the cell growth chambers is enabled using the compartmentalized microfluidic system which is organized in a planar and a vertical organization and the semi porous wall around the cell growth compartment has a specific structure for fluid to flow from one cell growth compartment to another.

The specific structure has an array of small pores which are located in the upper side, lower side, middle and entire wall length of the semi porous wall. In one embodiment, a tissue integrity in real time is monitored in the cell growth compartment using a trans-epithelial electrical resistance device. The other methods could be dyes or other means. In one embodiment, an inter-cell growth compartment flow of a nutrient, extracellular matrix fluid between two cellular growth compartments is controlled using a set of an external pump.

In one embodiment, the modular microfluidic device prior to layering is fabricated using one of a silicon micromachining, soft lithography, injection molding, 3D printing and laser machining. In one embodiment, the modular microfluidic device enables mapping of one or more tissues with a spatial and temporal architecture that emulates an in vivo human organ orientation for testing effect of a drug. In one embodiment, a multi-cell growth compartment structure with a combination of planar and vertical organization and interfaced with a planar and a vertical porous barrier. In another embodiment, the modular microfluidic device prior to layering is fabricated using one of a silicon micromachining, soft lithography, injection molding, 3D printing and laser machining. In another embodiment, the multi-cell growth compartment structure is one of a linear order structure, parallel structure, honeycomb structure and concentric structure and the semi porous wall is one of a straight, curved and meandering.

In one embodiment, the fluidic material flow is directed from a most outer compartment to a most inner one or vice versa. The perfusion channels within the walls surrounding the compartments create the pores hence, rendering the wall as porous. The semi porous wall has a porosity of ~50% and perfusion channels (pores) with width, height, and length of 3 μm, 10 μm and 50 μm. In another embodiment, the compartmentalized fluidic system is one of a channel, a bridging channel or a combination of the channel and a bridging channel. The other embodiments are stated in detailed description as well. In another embodiment, the compartmentalized fluidic system has two or more chambers which are connected with bridging channels.

BRIEF DESCRIPTION OF FIGURES

Example embodiments are illustrated by way of example and not limitation in the figures of the accompanying drawings, in which like references indicate similar elements and in which:

FIG. 7A, FIG. 7B, FIG. 7C, FIG. 7D, FIG. 7E and FIG. 7F shows two culture chambers selectively connected with a bridging channel.

FIG. 16A, FIG. 16B, FIG. 16C and FIG. 16D shows bonding process of the porous membrane to the upper layer with a porous wall structure.

FIG. 18A and FIG. 18B shows Finite Element Analysis of the flow profile through the perfusion system with various shapes of modular microfluidic device.

FIG. 28A, FIG. 28B and FIG. 28C shows multi-planner chambers connected to a bottom chamber connected via SPW's and porous membrane, 3D fabricated device and color diffusion through SPW's.

FIG. 33A, FIG. 33B, FIG. 33C, FIG. 33D, FIG. 33E, FIG. 33F, FIG. 33G and FIG. 33H shows cell culture arrangement in Vascular 4xC modular microfluidic device.

Figure 1A:
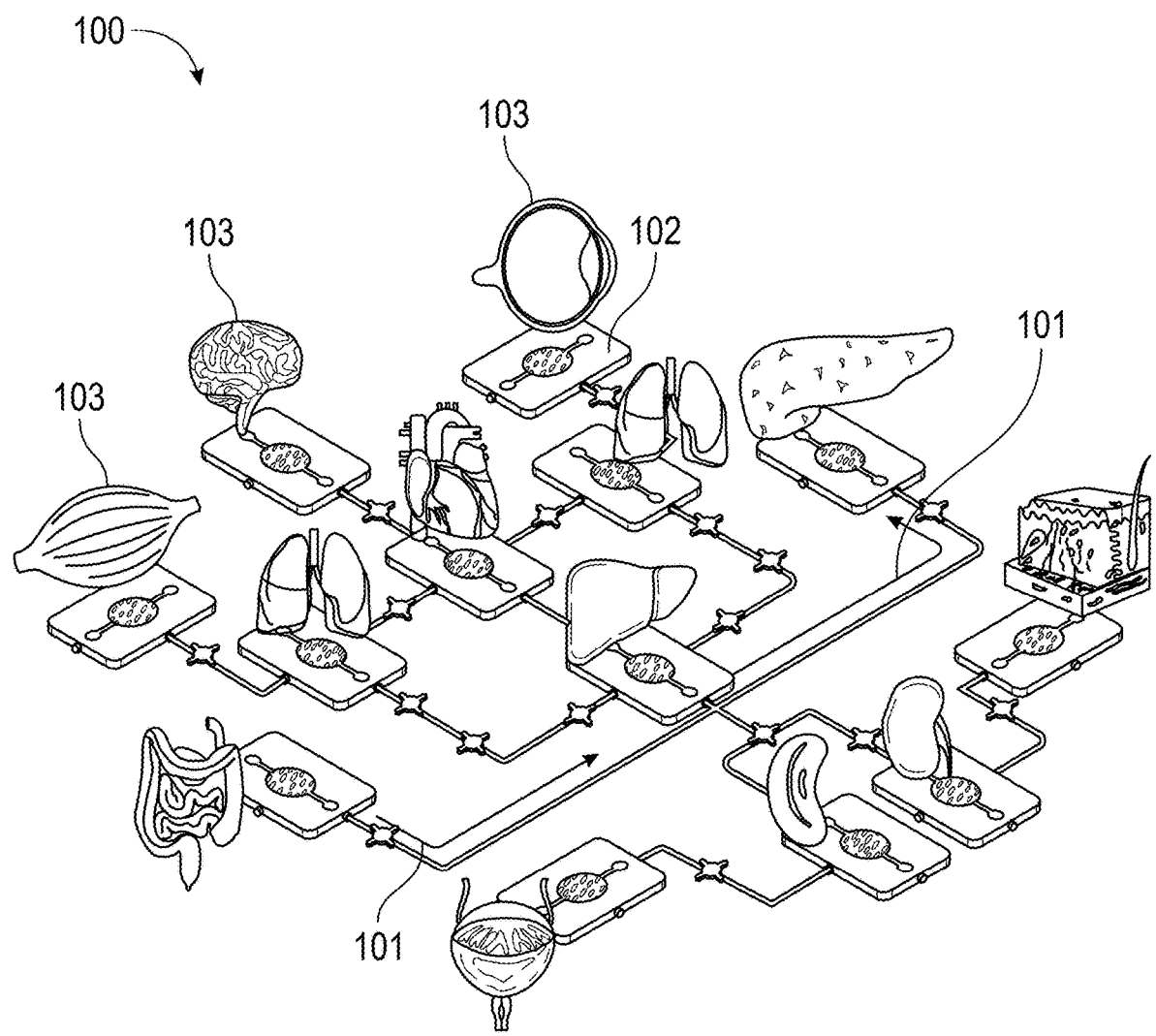
FIG. 1A, FIG. 1B, FIG. 1C, FIG. 1D, FIG. 1E, FIG. 1F and FIG. 1G shows conceptual drawings of multi-Organ-on-a-Chip Systems.

Others features of the present embodiments will be apparent from the accompanying drawings and from the detailed description that follows.

DETAILED DESCRIPTION

Instant disclosure describes a modular microfluidic device and system, and such devices can be used to create cell-based in vitro models that would increase the predictability of human response to drugs and significantly reduce experimentation expenses and speed up the screening processes. Microfluidic-based organotypic cell culture has the potential to create an "in vivo-like" cell microenvironment, and they are more amenable to automation and integration, and therefore providing efficient tools for disease modelling and screening, hence narrowing the gap between in vivo and in vitro systems by providing a controlled cell microenvironment and integrating various cellular systems with enhanced cell-cell interactions.

The cellular organization within an organism is a direct reflection of the specific functions of its tissues. This is because cells, tissues, and organs engage in communication through the secretion of diverse soluble factors and extracellular vesicles. These molecules play a crucial role in facilitating peripheral crosstalk with the circulatory system. The interconnection of different organ modules in an in vitro setting has a significant impact on their functionality and efficacy. To study inter-organ communication, common medium that serves as a mimic of circulating blood is used. This medium facilitates the transportation of essential components such as nutrients, soluble factors, cell metabolites, and drugs, enabling organ crosstalk. Developing a universal cell culture medium that effectively maintains the phenotypes and functions of all organs within an in vitro system poses a considerable challenge. However, it is important to note that this approach is limited to tissues that have already reached maturity and exhibit phenotypic stability. It necessitates the exploration of innovative solutions and approaches.

In vivo, organs are interconnected through complex networks of blood and lymphatic vessels, allowing for effective communication between them. This communication takes place through diverse mechanisms, such as the exchange of signalling molecules, exosomes, and cells that are transported between organs. Homotypic and heterotypic interactions are essential for various biological processes, including tissue development, repair, and the maintenance of homeostasis.

Organ-on-a-microfluidic device (OOC) technology (instant claimed microfluidic device and system) represents an advanced approach to cell culture architecture. It offers means to achieve accurate cellular positioning and in vivo-like cell polarization. This is accomplished by providing a template where cells can reproduce a complex assembly and mimic the organization found in actual tissues. To construct an in vitro organotypic cellular structure that allows for fluidic, biochemical, and chemical exchange, microfluidic systems are fabricated to enable the organization of different cell types in a manner that accurately reflects the tissue architecture in vivo. Employing 3D cell culture techniques allows for the creation of multicellular structures, spheroids, or organoids. However, tissue architectures in vivo often do not naturally form spheroidal structures. As a result, cell culture methods must be employed to induce the formation of cell assemblies and their surrounding extracellular milieu. This is necessary to enable the development of physiologically relevant structures before utilizing the in vitro model for analysis. An example of such architectural feature is the polarity which is an inherent characteristic of the epithelial cells. Polarity is established through the asymmetrical distribution of proteins in the cell membrane and is determined by the formation of tight junctions (TJs) between cells. These TJs separate the basolateral and apical membranes and play a crucial role in creating polarity. Polarity is a defining characteristic of epithelial, endothelial, and liver structures and functions.

The advancement of microfluidic technology has facilitated the integration of different cell types and organs within a single fluidic circuit. This innovative approach allows for the establishment of organ-organ crosstalk while maintaining the individual functionality of each organ. Furthermore, it mimics the role of vascular perfusion observed in vivo.

The successful design of a compartmentalized fluidic system for OOC technology is crucial to establish a relevant and effective in vitro model. This design involves considering several critical parameters. These include determining the appropriate size of individual compartments, which should correspond to the size of the hosted organ. Additionally, the order in which the organs are connected, the tissue orientation, and the perfusion rate within each compartment must be carefully considered.

The design of OOC systems is primarily guided by the physiological parameters that must be replicated in an in vitro setting. This can be accomplished by creating a minimal functional structure of an individual organ or by integrating multiple organs within the system. Key cell models, selected from either cell lines or induced pluripotent stem cell (iPSC) sources, are utilized to represent the specific organ or organs of interest. In addition, biochemical stimuli such as drugs and toxins, as well as physical stimuli like hydrodynamic, mechanical, and electrical cues, are employed to simulate the relevant physiological conditions within the OOC system. OOC systems facilitate dynamic interactions between diverse cell types, thus allowing for the replication of specific functions in an in vitro setting with the ability to conduct time-resolved measurements at various checkpoints, thereby providing insights into dynamic biological processes.

To establish a physiologically relevant organotypic structure and facilitate functional coupling that supports cell nutrient supply, chemical signalling, and paracrine communication, OOC systems employ various connection strategies: (i) Convection-based fluidic transfer, which can be achieved through manual pipetting or the use of tubing. This connection method does not rely on micro-fabricated channels to link the fluidic chambers. However, this approach method has certain limitations mainly its inability to fully recapitulate the physiological flow between organs. This method is limited to using organs that can be sustained by the same culture medium. The arrangement of cell types in this particular design does not accurately replicate the in vivo organization, where there is a significant distance between different types of cells in terms of cell-cell interfacing (e.g., the channel/tubing). This design is well-suited for connecting cells or tissues that are separated by a certain distance, such as heart-liver or intestine-liver connections. However, it does not provide a physiologically relevant cell-cell interface when attempting to model the complex cellular structure of an individual organ, such as the liver, which comprises multiple cell types (hepatocytes, hepatic stellate cells, sinusoidal endothelial cells, and Kupffer cells). Furthermore, it does not facilitate the interaction between parenchymal and nonparenchymal cells or immune cells, where the proximity between cells is crucial. Few commercial platforms became available. For example, TissUse GmbH (Berlin, Germany) introduced a variety of HUMIMIC Microfluidic devices, such as HUMIMIC Microfluidic device2, HUMIMIC Microfluidic device3, HUMIMIC Microfluidic device4, and HUMIMIC Microfluidic device XX/XY, for different in vitro modelling purposes, which enable the integration of 2, 3, and 4 organs. (ii) Utilizing porous barriers or gels with a planar orientation. In this configuration, cells are assembled and cultured in a two-dimensional (2D) arrangement within two/three planar compartments that are separated by semi-porous vertical barriers. This arrangement allows cells of different types to be cultured in close proximity to each other, ensuring physical isolation while maintaining fluidic and chemical connectivity between the compartments. The horizontal order of cell co-culture is a frequently employed structure in OOC systems. This arrangement is preferred due to its ease of fabrication and its suitability for studying the interaction between cells. While the planar arrangement is a commonly used configuration in OOC systems, it may not fully replicate the anatomical cellular assembly observed in vivo. In certain cases, the orientation of cells assembly is characterized by cell stacking with specific polarizations, such as the blood capillaries located beneath the intestinal or skin barriers. (iii) Using porous membranes. In this configuration, two fluidic compartments are vertically stacked and connected through a porous membrane. This organization allows for the co-culture of two or more cell types in close proximity to each other in two vertical orientations. By culturing epithelial, endothelial, or epidermal cells on the upper surface of the membrane, and the corresponding parenchymal tissue on the lower side, this structure closely mimics the architecture and functionality of critical biological barriers found in the human body. These barriers include the small intestine, lung parenchyma, skin, and blood vessels, which play crucial roles in regulating the interaction between the body and external factors such as drugs, food, and the environment.

OOC systems are fabricated to emulate the multifaceted nature of human physiology. Consequently, these systems inherently exhibit a remarkable degree of integration and complexity. To construct an in vitro model that is sufficiently physiologically relevant, it is imperative to include the minimum number of cell subsets in the co-culture system. However, the incorporation of additional cell types, tissues, or organs into the system leads to an expansion of compartmentalization. As a result, the complexity of the biological model necessitates the engineering of a sophisticated device with multiple fluidically connected compartments that enable dynamic mapping of the tissues with a spatial and temporal architecture that emulate that of in vivo.

Current bioengineered systems necessarily are developed to model a single tissue/organ, such as a lung, gut, liver or tumour within one or two compartments with poor interfacing mechanism between physiological components. The majority of OOC devices are commonly produced using soft lithography techniques and PDMS which tends to absorb small organic compounds, including the analytes of interest. Using this technique, it is difficult to achieve precise and consistent positioning of different cell types in close proximity, which is crucial for efficient and physiologically relevant paracrine signalling.

In order to study the effects of communication between organs, multiple tissue environments are required. In vivo, it is challenging to isolate the interactions between just two organs, because they are embedded within the complex whole-body environment; signals released by each organ are quickly diluted into the bloodstream and delivered too many other tissues. Therefore, it is difficult to determine the relative contributions of each cell type to any physiological event.

In the instant disclosure we describe micro-engineered modular cell co-culture systems that enable the recapitulating of the structure of an individual human organ or a network of organs so that metabolites and paracrine signals can be transported and exchanged between various tissues or organ models towards bridging the existing gap between in vivo and in vitro studies. The 3D microfluidic systems can be utilized to grow different type of cells in various architectures which can take the shape of 2D or 3D with improved cell-cell/tissue-tissue interaction. Therefore, this platform system can be used to build various in vitro models. The 3-dimensional perfusion nature of our microsystem would improve the nutrient mass transfer into the constructed tissue and consequently prolong the tissue (i.e., organ model) viability for multi-parametric analysis. In addition, biological barriers such as intestinal/lung/skin epithelium, which are considered the gateway to drug delivery, can be monitored in real time by employing a set of micro-electrodes.

Figure 1B:
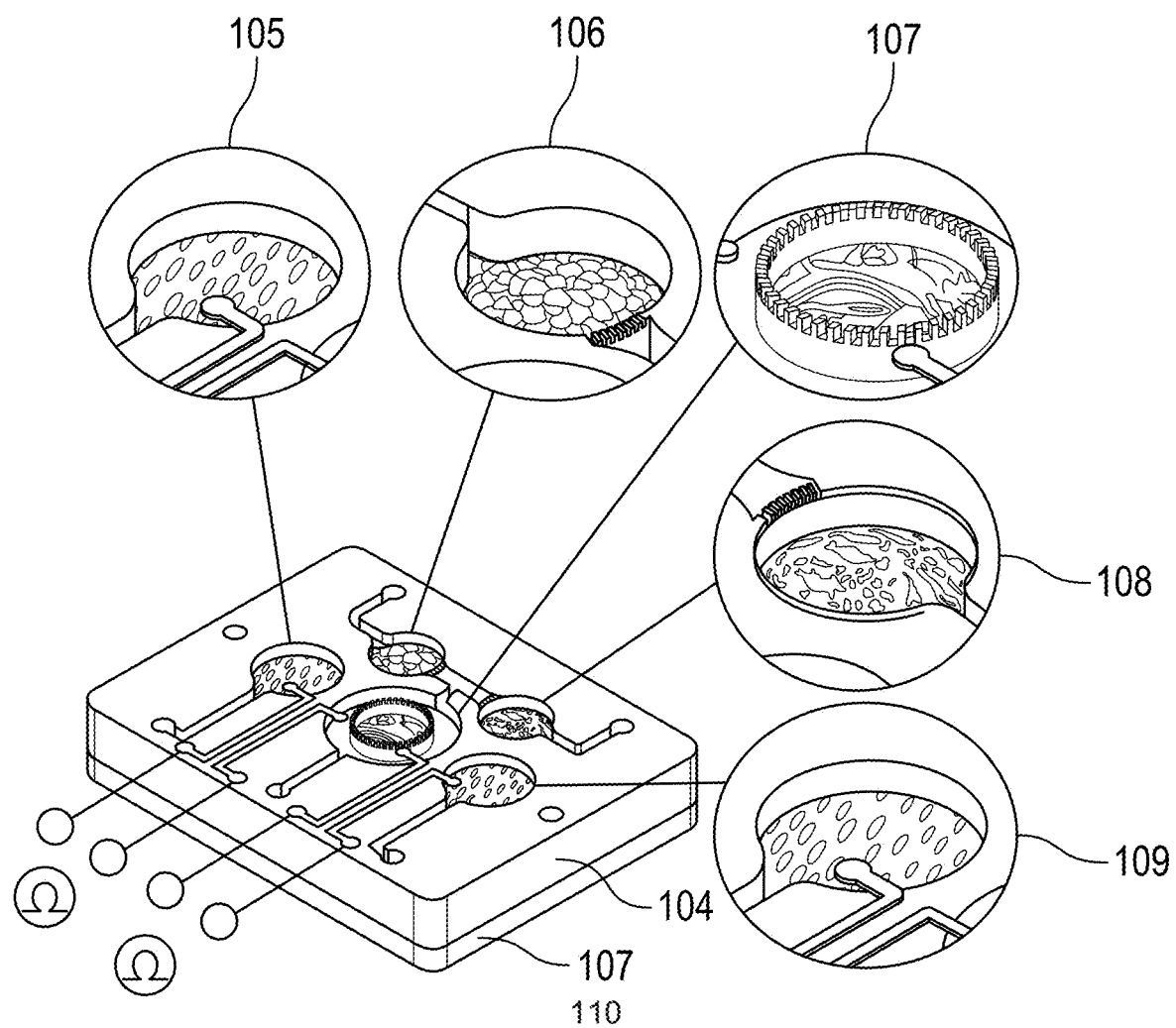
Figure 1C:
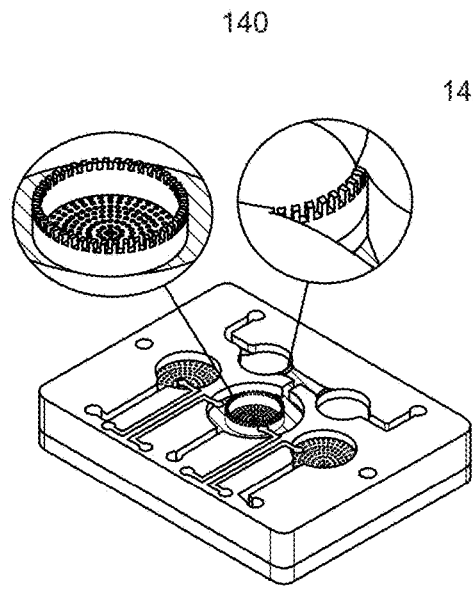
Figure 1D:
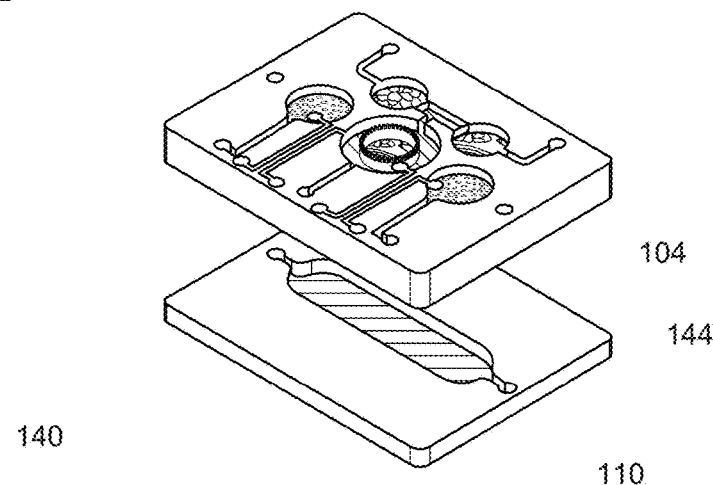
Figure 1E:
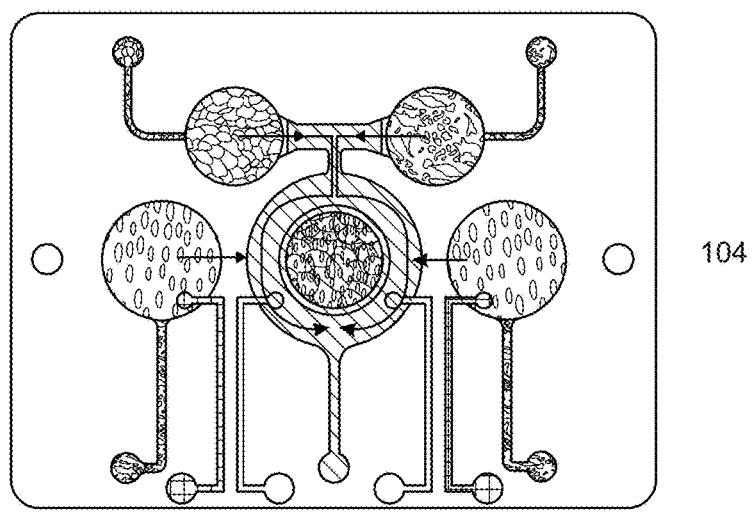
Figure 1F:
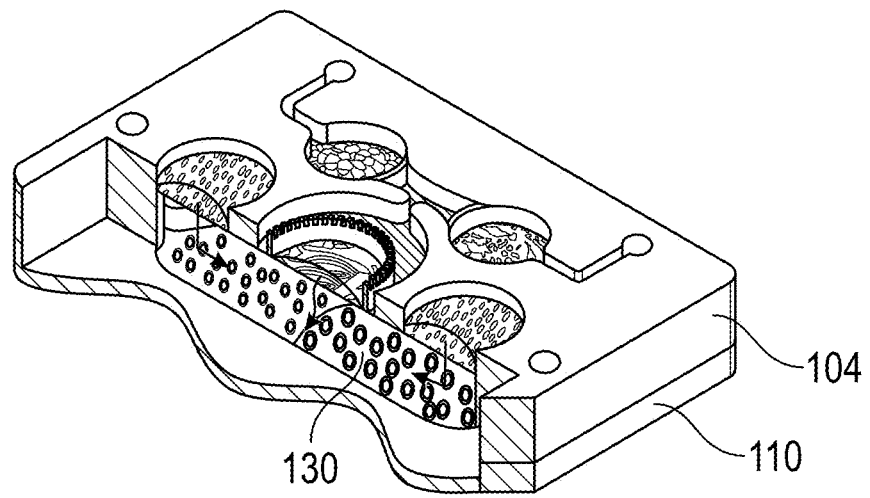
Figure 1G:
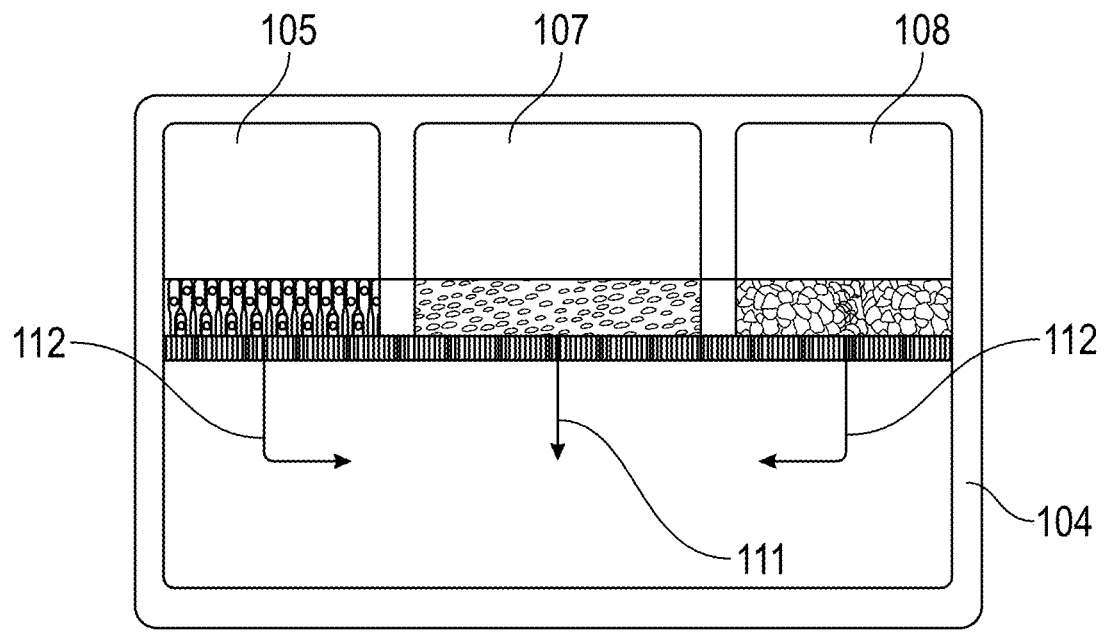

FIGS. 1A, 1B, 1C, 1D, 1E, 1F and 1G shows conceptual drawings of multi-Organ-on-a-Microfluidic device System. FIG. 1A shows a schematic conceptual drawing (100) of the system which hereafter called multi-Organ-on-a-Microfluidic device System (mOOCS). Cell models of specific organs (103) can be grown in individual microfluidic devices (102) and connected through channels (101) and porous barriers. FIG. 1B shows a representing example of the mOOCS (104) which is a compact system that allows efficient communication between (110 lower plate) various cell culture models 105, 106, 107, 108, and 109 through porous barriers (in horizontal 104 and vertical orientation 110). FIG. 1C shows the compartmentalized system 104 comprises a number of porous barriers in horizontal positioning (membrane 140) and vertical positioning (porous walls 142) that allow cell signalling between the various cell cultures. FIG. 1D shows the system comprises vertically stacked compartments 104 and 110 separated by porous membrane that enable fluidic/chemical crosstalk between the various compartments. The lower plate 110 has a reservoir 144 for nutrients storage. FIG. 1E shows top view of the mOOCS device 104. FIG. 1F shows 3D cross-sectional view of the a mOOCS device with a top layer 104, bottom layer 110 and a membrane in between 130. FIG. 1G shows a 2D cross-sectional view of the a mOOCS device. Th upper cell growth compartments with different culture cells from different organs 105, 107, 108 are linked to the lower layer 110 via a membrane (112). There is media (111) that contains circulated cells and shows circulation of media and calle. The system 100 involves four innovative features and rest of the systems that shown in figures throughout is an improvement, addition and modification of a base system:

- Novel 2D/3D compartmentalized fluidic structure (101) that enables culturing various types of cells (103) in planar and vertical organization with enhanced cell-cell/tissue-tissue interaction.
- Perfusion channel array for mimicking the physiological flow in the human body (e.g., blood flow in capillaries).
- Novel porous barrier structures, with horizontal and vertical orientation, for recapitulating the drug/nutrients/toxin absorption, paracrine signalling through the various biological barriers and downstream distribution, metabolism and exertion (ADME).
- Novel design for sensor-tissue interface. Particularly for monitoring the permeability of molecules through the biological barrier models.

The system is designed with micro-engineered features that allow controlling the fluidic characteristics (101), such as flow rate, mass transfer and mechanical shear stress, through a compartmentalized bioreactor which can host various cellular modules to recapitulate various physiological and metabolic characteristics in the human body. These include:

a. Maintaining the tissue/tissue size ratio between the different organs in vivo by custom design the size of each tissue compartment as well as maintaining a physiologically relevant tissue/liquid ratio within each cell growth compartment.

b. Controlling spatiotemporal fluidic flow into and from the cell culture compartments to emulate the local flow of blood flow and mass transport of nutrients into and out of the tissue as well as maintaining physiologically relevant shear stresses onto the surface of specific tissue such as the endothelium and epithelium.

c. Controlling the transport and distribution of nutrients and metabolites into the body through the different barrier tissues such as skin, gastrointestinal tract epithelium and blood vessels endothelial.

d. Allowing micro-scale spatial heterogeneity of cells and tissue.

e. Facilitating efficient cell-cell and tissue-tissue interaction between heterogeneous cell cultures.

f. Allowing spatial organization of different type of cells/tissue (105, 106, 107, 108, 109) in 2D and 3D architectures with physiologically relevant order.

g. Allowing recruitment of circulating immune cells with high spatiotemporal resolution of cell-cell interaction.

h. Allowing real-time monitoring of tissue (epithelial/endothelial/epidermal) integrity by measurements of the Trans-(epithelial/endothelial/epidermal) Electrical Resistance (TEER).

The microfluidic device and system described here represents a highly controllable miniaturized system that enable faithfully reproducing key physiological aspects of the complex human physiology by allowing the simultaneous presence of all main cellular actors and testing potential therapeutic agents in a physiologically relevant environment. The fabrication of these system relies on multiple microfabrication processes to realize a manufacturable prototype. Despite the inherited complexity of the systems, further development of its engineering structure and interface will transfer the prototype to a user-friendly and its modularity allows for certain simpler components of the system to be custom designed to meet specific applications. It is important to note that the primary focus of this work is on the engineering aspects, specifically the design and fabrication of the microfluidic device.

Design of the systems: We have designed and fabricated compartmentalized perfusion platform (107 and 104) that enables the construction of a variety of customizable microscale in vitro models of human individual organs or multi-organs. The design of the system allows creating an appropriate cellular environment by mimicking the in vivo cell exposure to nutrients and stimuli flow as well as the interaction between different types of cells. Conventional cell culture-based in vitro systems are routinely used in drug discovery and development. These systems rely on a single cell type cultured in multi-well plates, in which the ratio of fluid to cells is large and physiologically not relevant. The drug candidates are directly applied onto the cell culture at doses that are not accurately correlated to that when taken by human (in vivo) which make it unrealistic. In addition, the response of multiple tissue types to the drug and the exchange of metabolites between organs are lost. In this study, the multi-compartment microfluidic system can be designed such that each compartment represents an organ/tissue and the sizes of the chambers that host the in vitro model of the organs reflect the sizes of the corresponding organs or tissues in the body. The size of these compartment as well as the concentration of the drug can be calculated from a physiologically based pharmacokinetic (PBPK) modeling or from clinical data. For example, data from PBPK can be used to scale a multi-organ microfluidic device to represent the appropriate tissue ratios, hepatic clearance and renal elimination of drug. In addition, due to the miniaturized nature of the microfluidic system and by maintaining a continuous flow of culture media into the cell culture chamber, the ratio between the cell volume and media can be reduced to minimum to simulate that in vivo. For example, when cells are cultured in a conventional culture flask with a surface area of 75 cm$^2$. 10 mL of culture media is added onto the cell culture which results in media/cell ratio (volume/volume) of 67 times, on the other hand, when the same cells are cultured in a microfluidic device with a surface area of 10-2 cm$^2$, the volume of media covering the cells is within the range of 20-30 µL which result in a ratio of media/cell of 6 only. Additionally, the cell culture compartments that represent the multi-organs can be organized in a hierarchy that mimics the physiological order (see FIG. 2 for example) which may allow tracking the key physiological events in disease progression and treatment.

Figure 2:
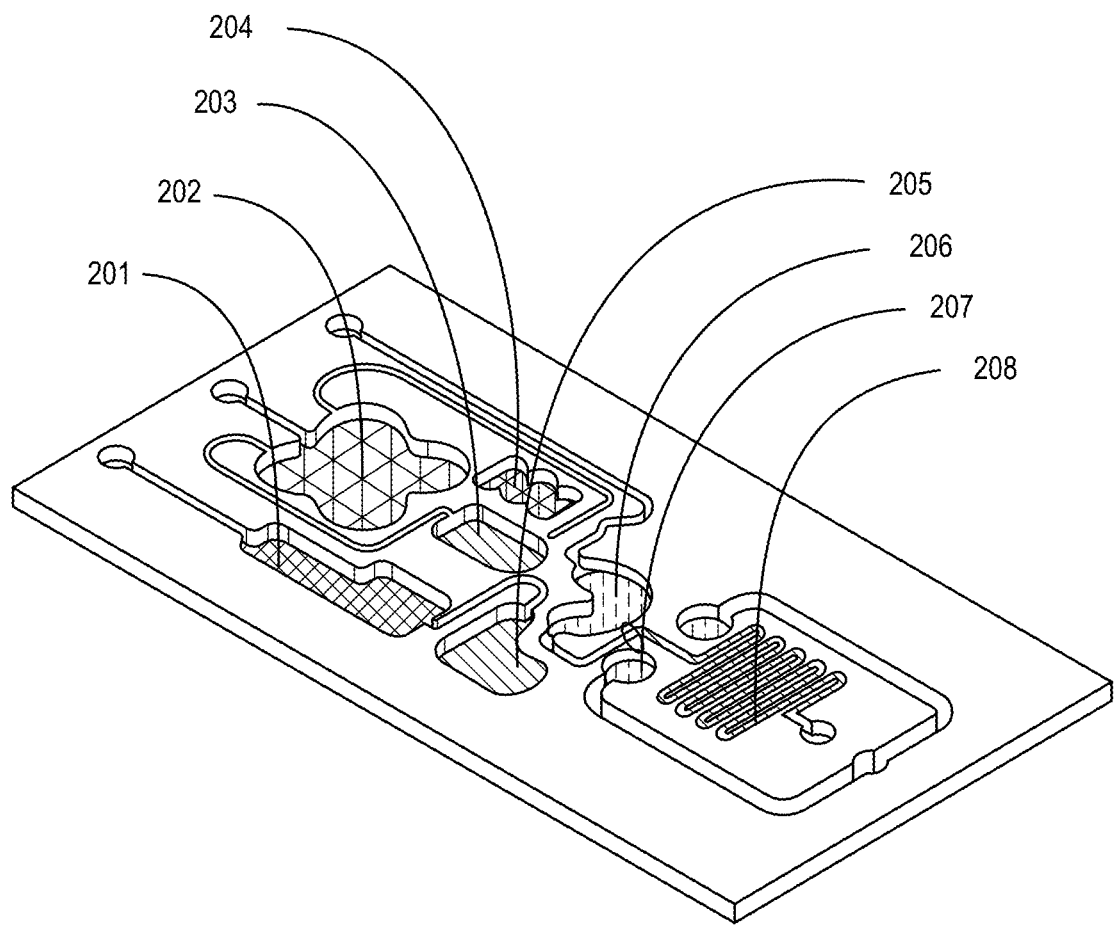
FIG. 2 shows a-microfluidic device hierarchical organization.

FIG. 2 shows a microfluidic device as Organs-on-a-microfluidic device hierarchical organization in another embodiment. Recapitulating the in vivo structure of an organ in vitro using cell culture is a challenging task because tissues and organs in the human body are not simply connected through fluidic ducts but through homotypic and heterotypic interaction that maintain the crucial tissue and organ structure and function by autocrine, paracrine and endocrine signaling. To close the currently existed huge gap between in vivo and in vitro systems and to allow recapitulating the physiological characteristics of organs, its crucial to maximize the presence of cell types which compose the specific organ and to mimic the specific cellular organization that insure in vivo-like cell-cell and tissue-tissue interactions. Here, we are addressing this concern and proposing a system that allows co-culturing various cell types/tissues in physically separated compartment while allowing fluidic connection/communication in three-tiered interaction modes between heterotypic cell co-cultures. Heterogeneous cell-culture assembly can be designed to emulate the structure of an individual organ or multi-organ in a porous compartmentalized microfluidic structure that enables cells and organ to interact through paracrine and endocrine chemical signals like in vivo. As an example, but not limited to, a modular microfluidic device having a skin (201), lung (202, heart 203, adipose tissue cells 204, liver 205, stomach 206, kidney 207 and intestine 208 are shown to be cocultured in cell growth compartments together. The organotypic structure can be organized/assembled in three different configurations: planar or complex 3D organizations with various permutations and combination of organ cells.

Figure 3A:
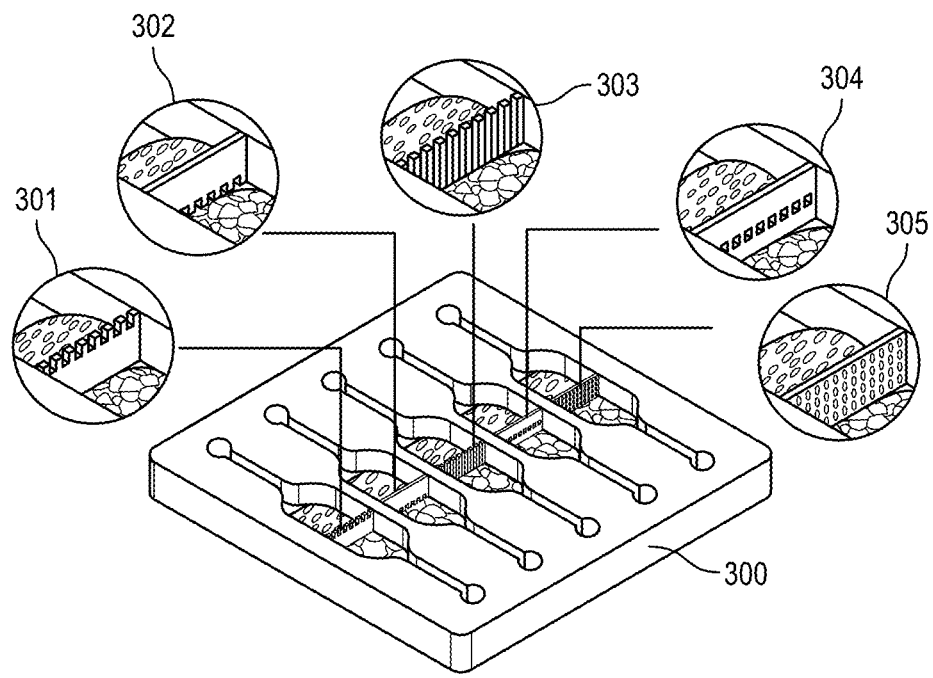
FIG. 3A and FIG. 3B show planner compartment organization with vertical semi-porous walls.
Figure 3B:
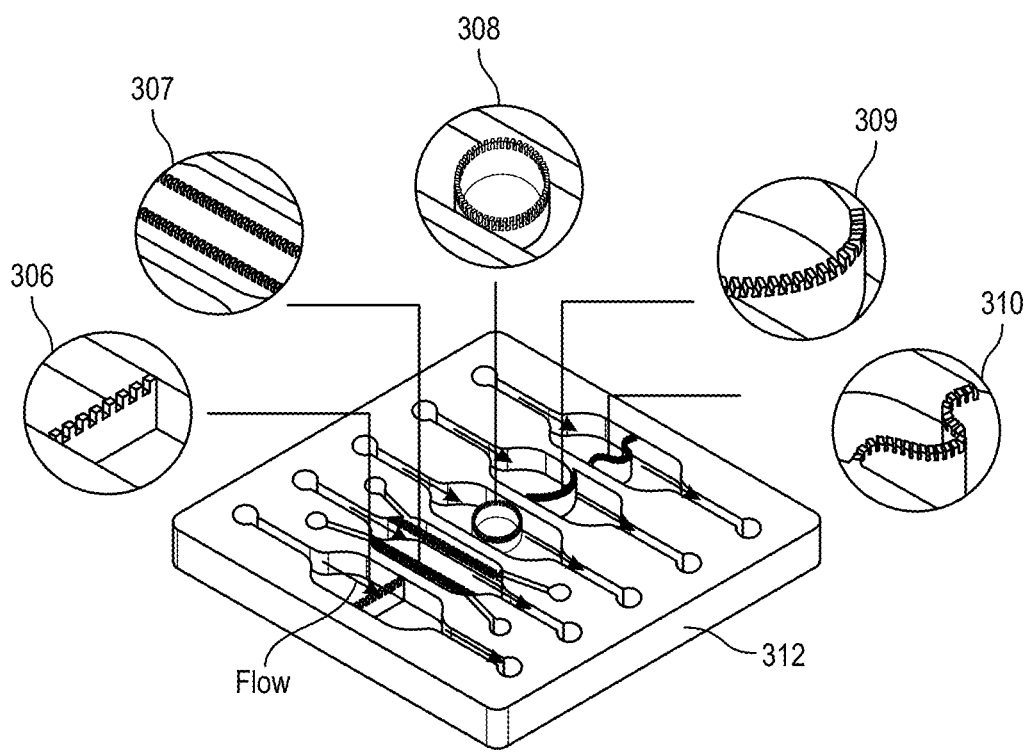

FIG. 3A shows a microfluidic device (300) having SPWs are characterized by an array of small pores which are located either in the upper 301, the lower side of the walls 302, through the entire wall height 303, in the middle of the barrier wall 304, and/or distributed through the entire surface of the cellular wall 305. FIG. 3B shows a microfluidic device 312 having a different SPW configuration. The SPWs can be fabricated in various orientations such as: perpendicular to the flow direction 306, parallel to the flow direction 307, a single curved wall 309, a circular 308 and a meandering wall 310.

Planner organization: Different types of cells can be cultured in a 2D organization within a planar compartmentalized structure. The multi-compartments in such a structure are physically separated by vertical semi-porous walls (SPWs). In such cellular organization, each cell type is cultured in its corresponding compartment that is contained in a SPW structure. Therefore, cells of different types are fluidically and chemically connected. The size of these pores can be customized to specific requirement to retain the cells in their corresponding compartment and enabling the exchange of bio/chemical signals and between the different compartments with controlled mass transfer between the various compartments. In sequence, this would enable chemical/biological interactions (paracrine signaling) between the cells in the different neighboring compartments. Each pore within the SPW creates a short micro-channel called perfusion micro-channel which connects the two compartments through perfusion. The ratio between the micro-channel depth and the compartment depth can vary from 1/100 to 1. In the latter case, the two compartments will be physically separated by an array of pillar structures. The rate and direction of the inter-compartment flow can be controlled using a set of external pumps and the heterotypic cell chemical interaction then can be emulated by the micro-flow through the SPWs.

Figure 4A:
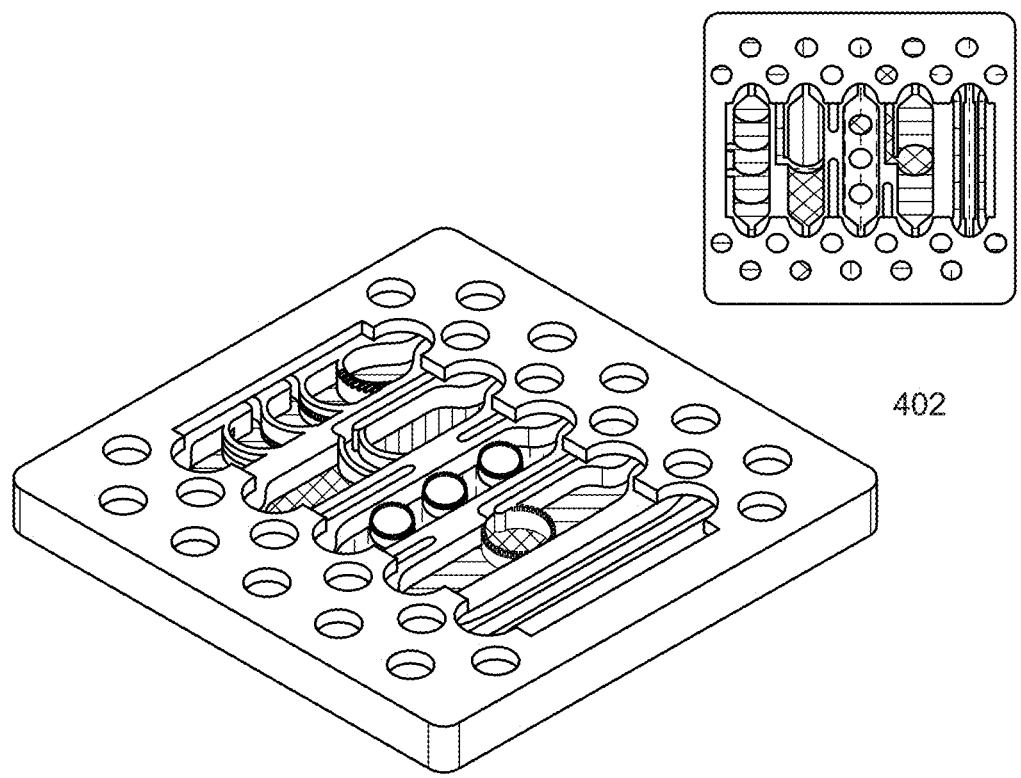
FIG. 4A, FIG. 4B, FIG. 4C and FIG. 4D shows arrangements of compartments on an organ on a chip.
Figure 4B:
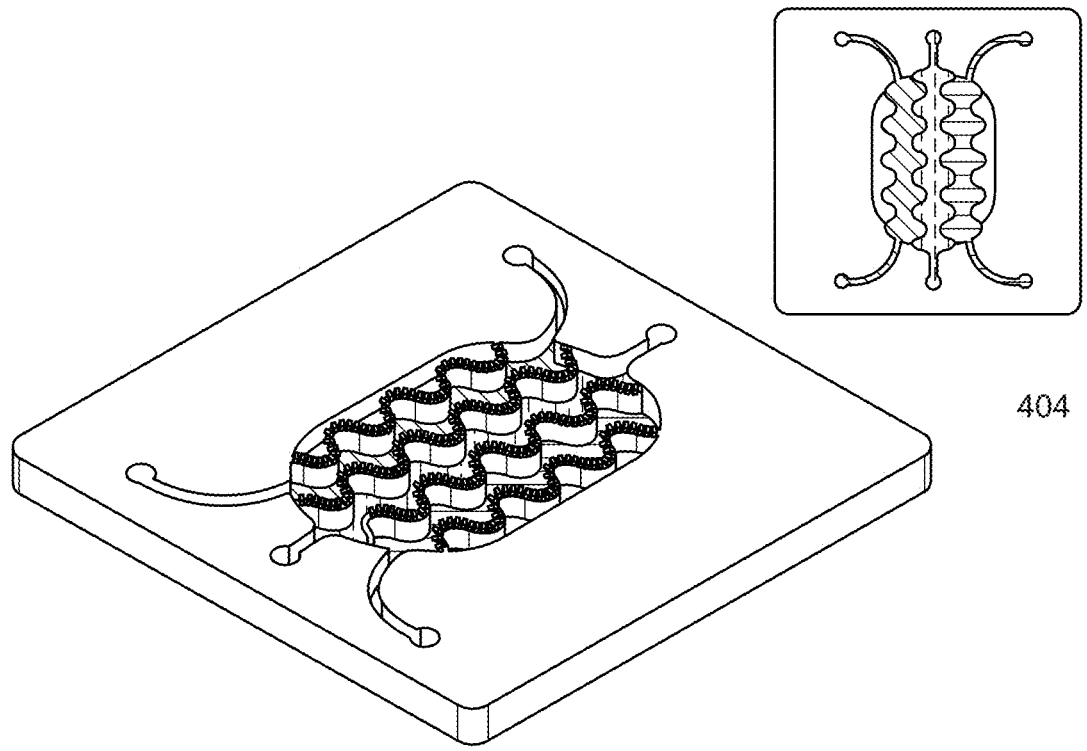
Figure 4C:
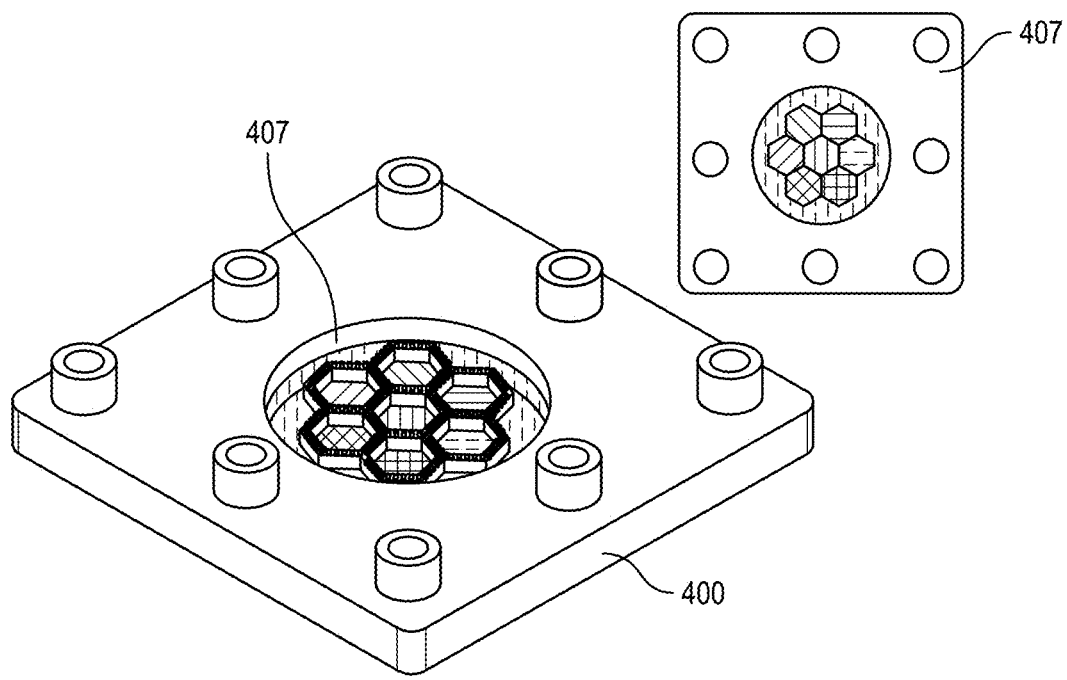
Figure 4D:
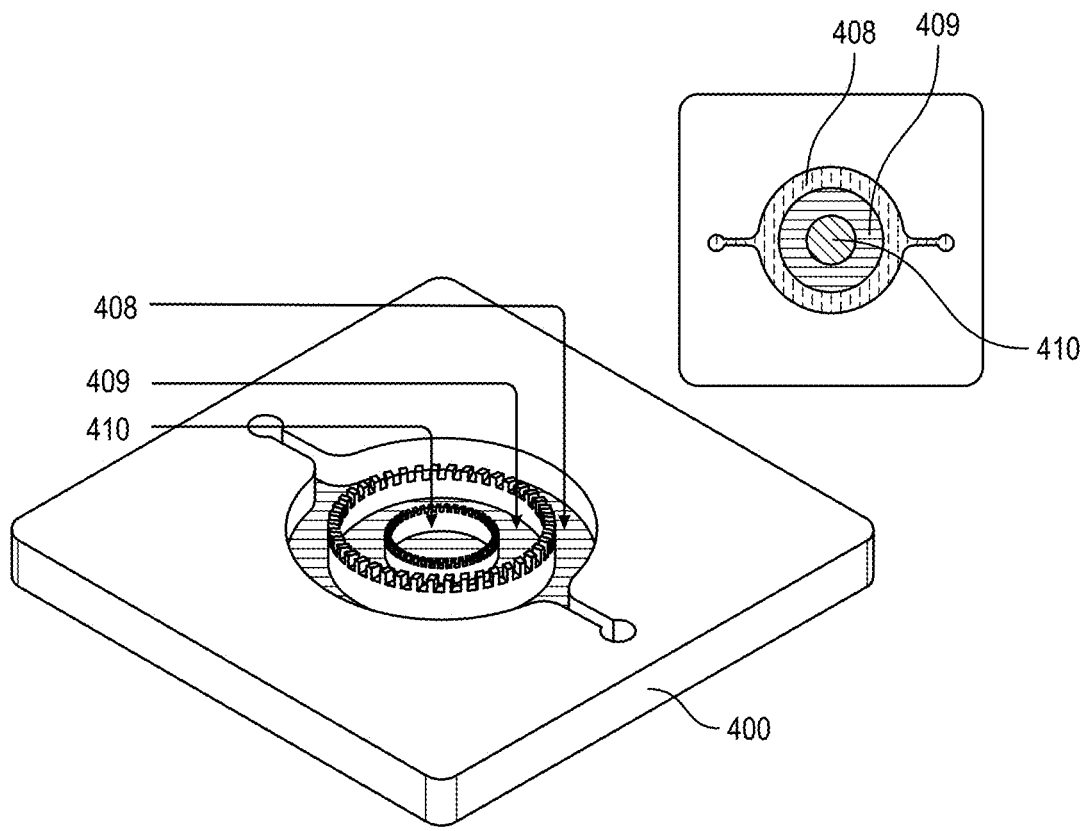

FIG. 4A shows a simple linear order: that the compartments are arranged in series in the same direction of flow 402. FIG. 4B shows parallel arrangement 404 along the flow direction. The SPWs can be straight, curved of meandering. FIG. 4C shows having microfluidic device 400 in a honeycomb structure 407: A central hexagonal compartment surrounded by 6 hexagonal compartments. All the compartments are fluidically connected through the porous walls. FIG. 4D shows concentric compartments 408,409 and 410: two or more compartments can be created sharing the same center and surrounded by porous walls. The SPWs can be arranged/designed to organize the planer in various orders/organizations such as:
 a. Simple linear order such that the compartments are arranged in series in the same direction of the flow (FIG. 4*a*).
 b. In parallel arrangement along the flow direction (FIG. 4*b*) the SPWs can be straight, curved of meandering.
 c. Honeycomb structure: such as a central hexagonal compartment surrounded by 6 hexagonal compartments (FIG. 4c). All the compartments are fluidically connected through the porous walls.
d. Concentric compartments (FIG. 4d): two or more compartments can be created sharing the same center and surrounded by porous walls. The fluid flows can be directed/switched from the most outer compartments to the most inner one or vice versa.

Figure 5A:
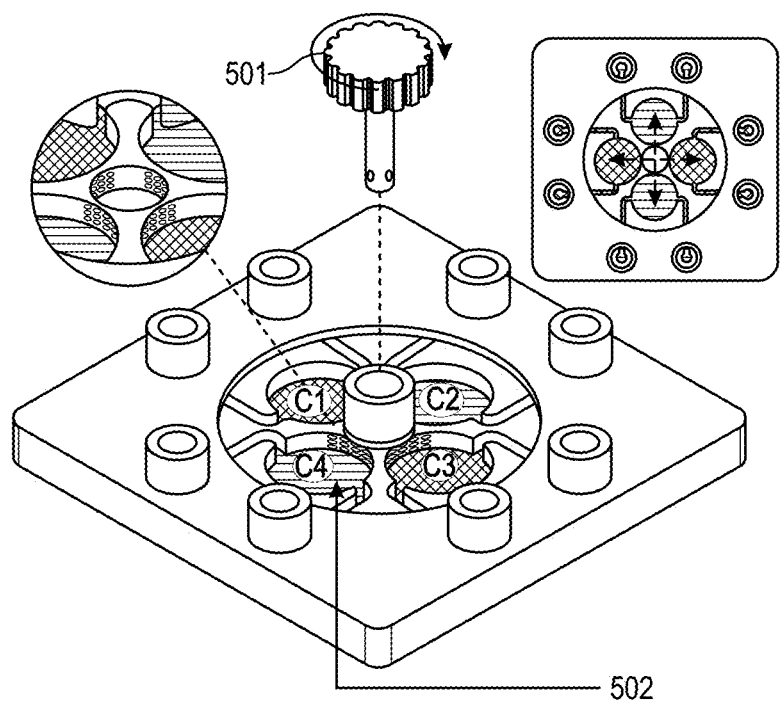
FIG. 5A and FIG. 5B shows a method of controlling the flow of fluid between compartments using a valve.
Figure 5B:
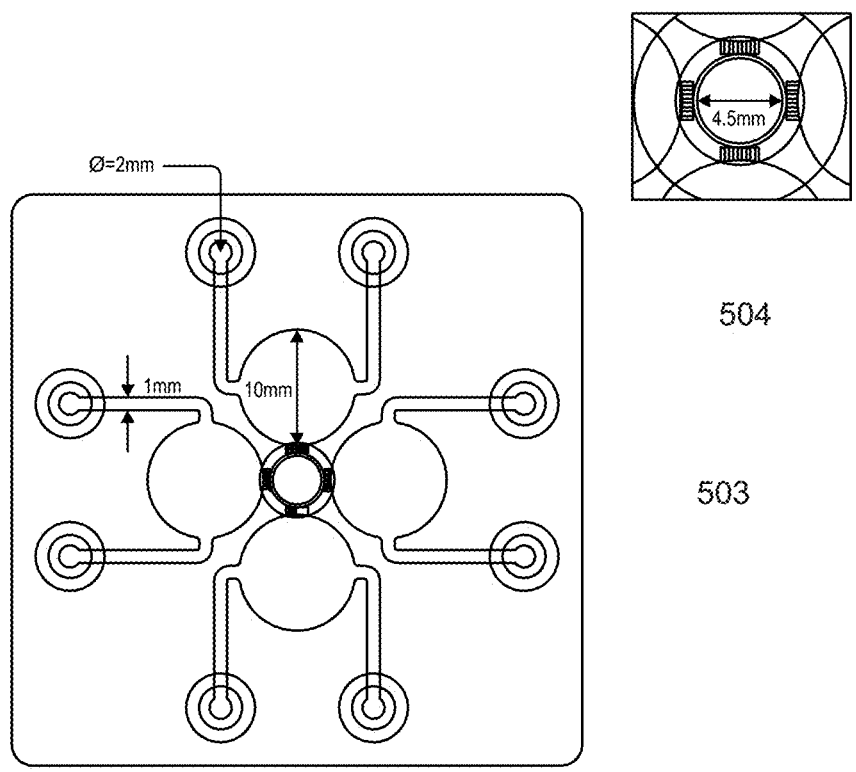
Figure 6A:
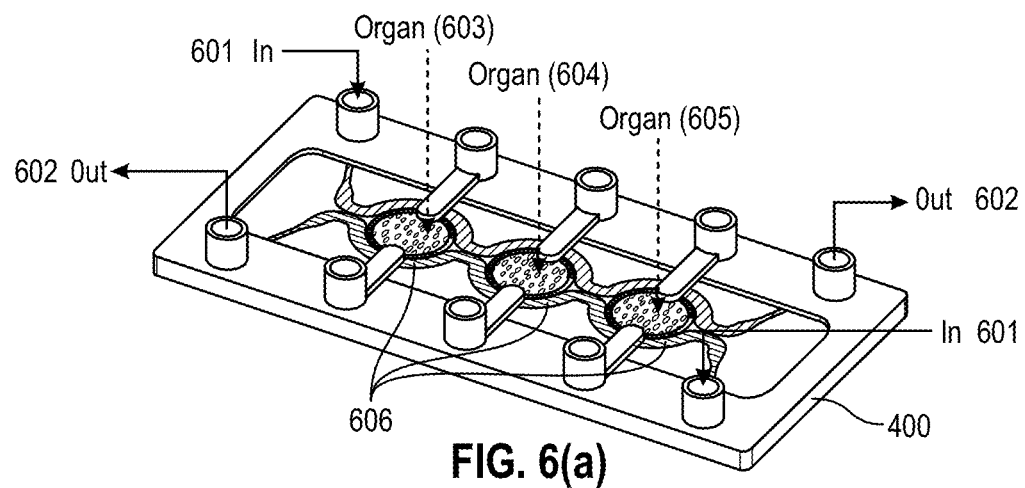
FIG. 6A, FIG. 6B and FIG. 6C shows different cell cultures in different compartments.
Figure 6B:
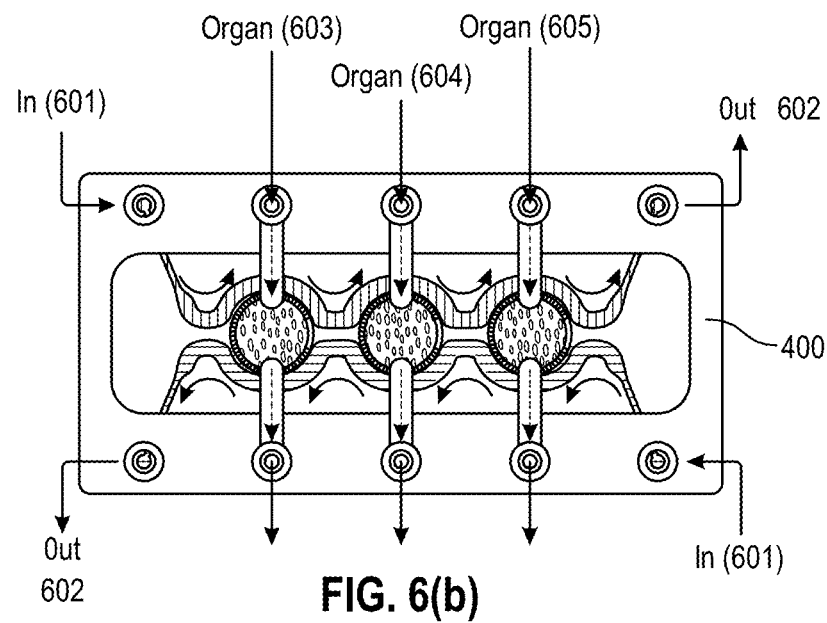
Figure 6C:
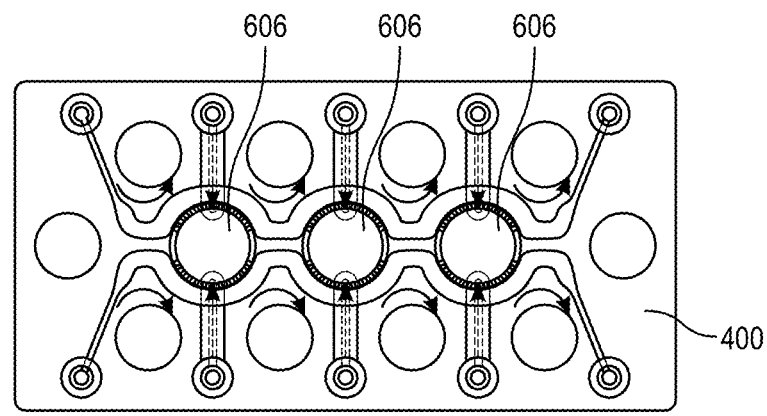

The crosstalk between two fluidic planer compartments can be controlled by a valve. FIG. 5a, shows four compartments 502 with a central cylindrical cavity with porous wall. The cavity links the four compartments through the SPWs. A cylindrical rod 501 with a hole close to the lower side can serve as a valve such that when the rod is inserted in the cavity, the hole in the rode will be aligned to the pores in two compartments in the two opposite sides (e.g., C1 and C3), meanwhile the other compartments (C2 and C4) are disconnected. The cylindrical valve can be rotated to open/close the pores between two opposite compartments to selectively allow the cells in the two compartments to communicate or to be completely separated. FIG. 5b shows a top view of the device highlighting the important dimensions, FIGS. 6A, 6B and 6C shows different cell cultures in different compartments in a microfluidic device (400). Two or more circular compartments with SPWs can be arranged in various planner organizations (e.g., linear). These compartments can be linked through two side channels in close proximity such that the fluid in the side channels is allowed to infuse into the compartments through the micropores (FIG. 6a). One side channel can be dedicated to providing the cells in the compartments with nutrients and growth factors (i.e., cell culture media) or stimuli (e.g., drugs and antibodies) and the other side channel will be dedicated to remove the waste from the cell compartments or extract the cell product for analysis. FIG. 6A shows three fluidic compartments 606 with different types of cell culture (i.e., organ model 603, 604, 605) are with SPWs surrounded by two sided channels. The compartments and the channel are allowed to exchange the fluid through the micropores which are surrounding the compartment. One channel can supply the nutrients or stimuli 601 (1.2 mm) while the other can be dedicated to waste removal or extracting 602 (1 mm) the cellular products for analysis. FIG. 6B shows the top view of the device which shows the flow directions in the compartments and the side channels. FIG. 6C shows the design of the cell growth compartment 606 in a microfluidic device 400 highlighting the flow direction of the two side channels which can be parallel or antiparallel. Each compartment can be accessed by its own fluidic inlet and outlet as shown in FIG. 6C.

Different types of cells often require tailored culture conditions and media compositions to support their growth and differentiation. Therefore, co-culturing multiple cell types with divergent nutritional and environmental demands can be challenging. A viable approach is to culture the cells separately during initial seeding, proliferation, and differentiation, before fluidically connecting the mature cell populations to enable paracrine signaling between them. This strategy allows optimal differentiation prior to assembly of a complex co-culture model. For instance, two or more cell monocultures can be maintained in fluidically isolated systems and eventually can be connected to other cells by using a bridging channel which can be selectively connected or disconnected at any time.

Figure 7C:
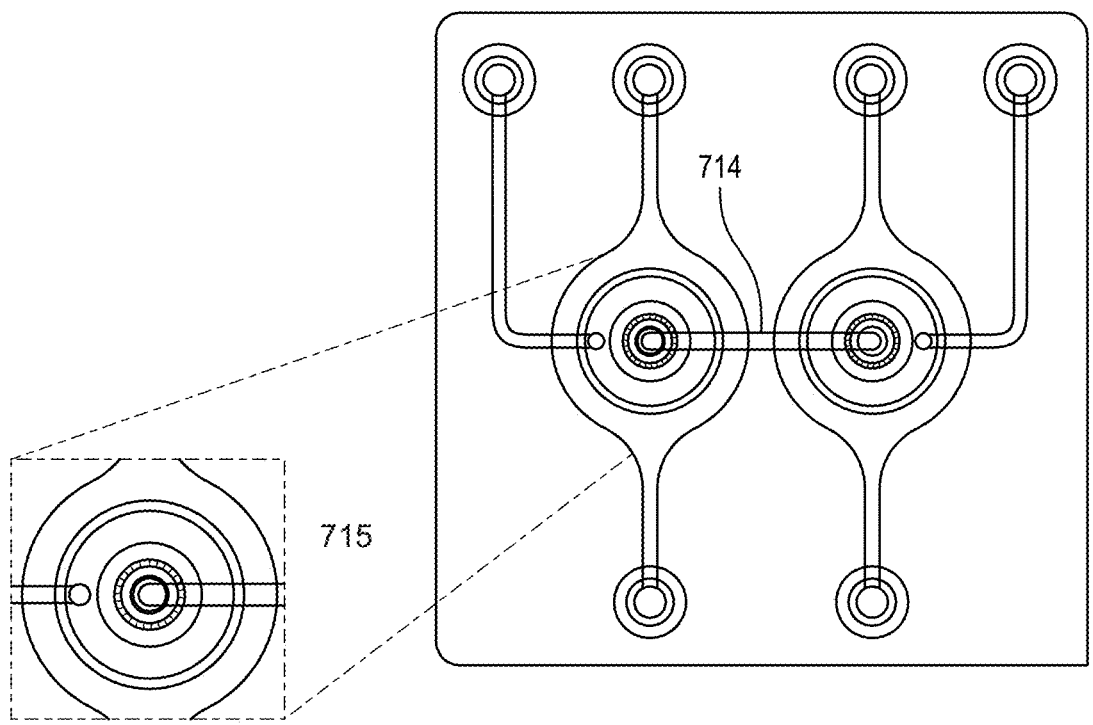
Figure 7D:
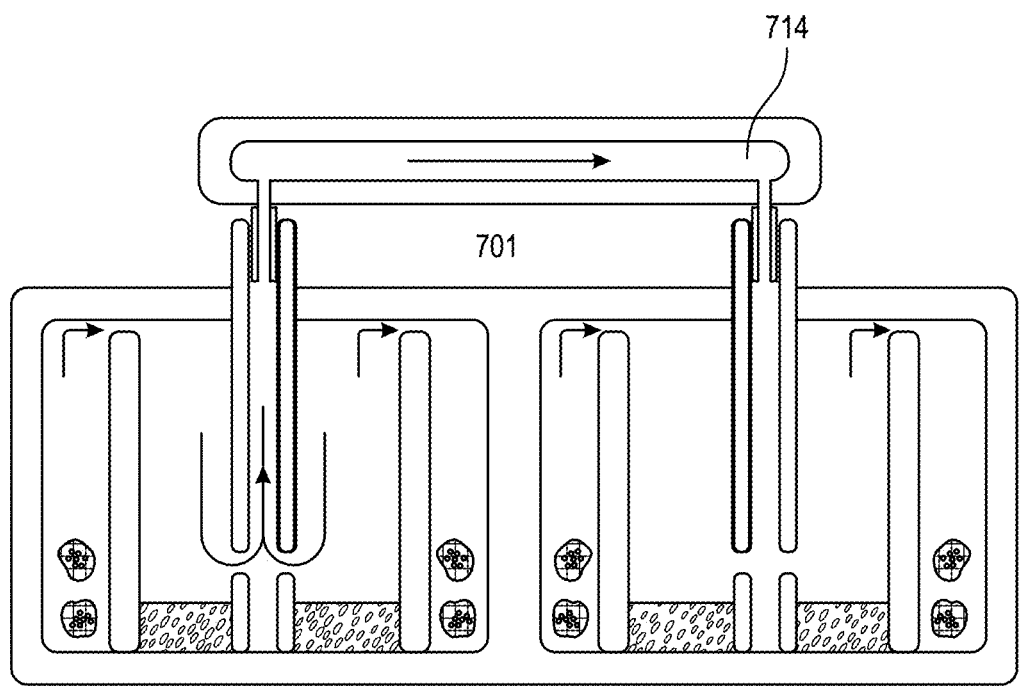
Figure 7E:
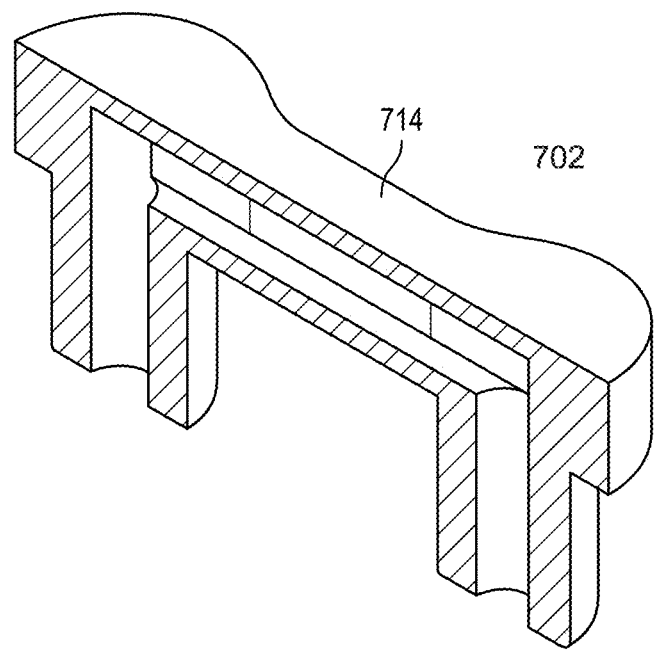
Figure 7F:
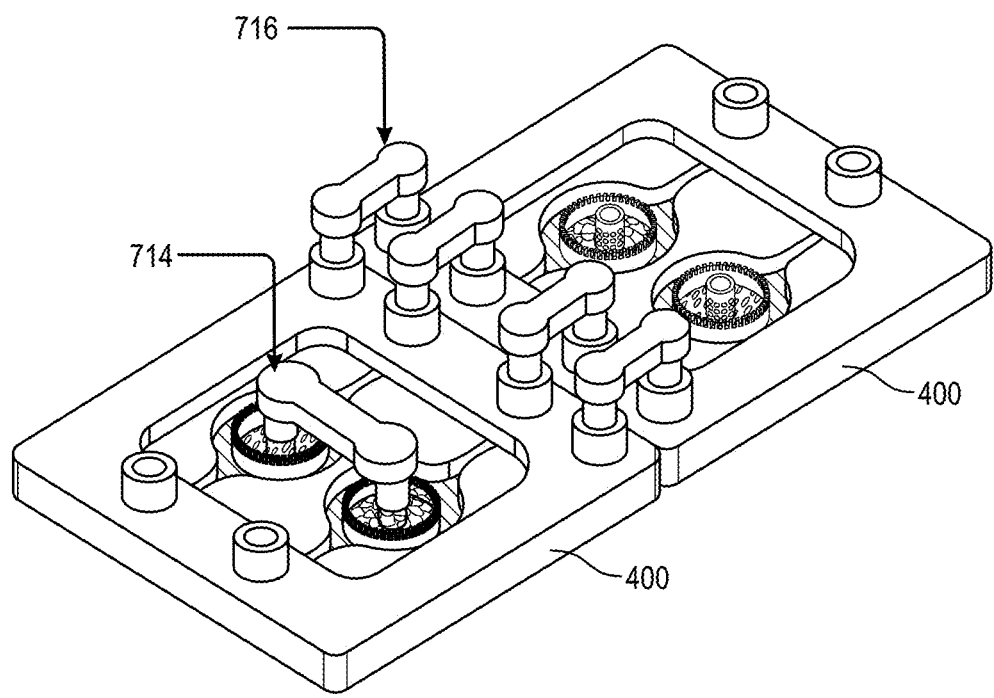

FIGS. 7A, 7B, 7C, 7D, 7E and 7F shows two cell culture chambers selectively connected with a bridging channel. FIG. 7A shows an over view of the two chamber microfluidic system 400 with each chamber comprises two concentric cell growth 704 compartment separated by a SPW and a central porous cavity (inset 708). An inlet and outlet for nutrients 706 are also shown. A bridging device 702 is shown where it could be connected to central porous cavity. Once the bridging device is assembled, the fluid from the first chamber will infuse through the pores of the cavity and flow inside the bridging device towards the second chamber and consequently infuse into the second chamber through the porous cavity. The dimensions of the bridging device may be 11 mm in length, inner width 6.5 mm, height 4 mm, inner channel 1.5 mm. FIG. 7B shows the two chamber in disconnect (left 710) and connected (right 712) states. FIG. 7C shows a top view of the device with a bridging channel 714 with a top cut to show the inside embedded channel. An enlarged figure of the growth chamber 715 is shown as well. FIG. 7D shows a detailed 2D crossectional view of the device which shows the flow direction 701 when the two chambers 704 are connected by the bridging channel 714. FIG. 7E shows a U-shaped bridging channel 714. When desired, a U-shaped bridging channel 714 can be assembled to connect the two chambers together such that the two ends of the bridging channel are inserted inside the porous cavity of each chamber. The two ends of the bridging channel can be inserted in the central porous cavities to connect the two chambers together.

Figure 8A:
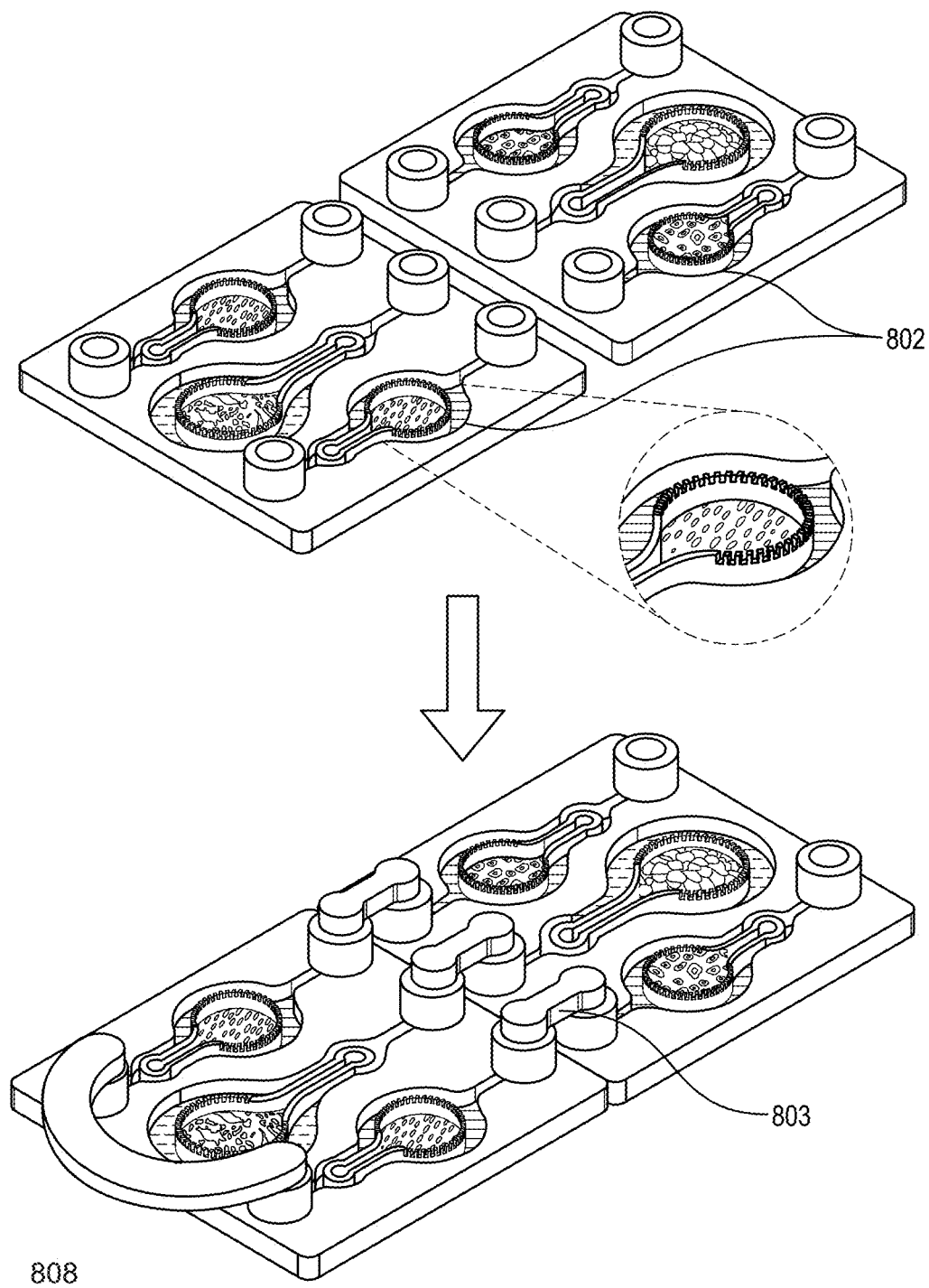
FIG. 8A and FIG. 8B shows bridging of two fluidic systems through external bridging channel.
Figure 8B:
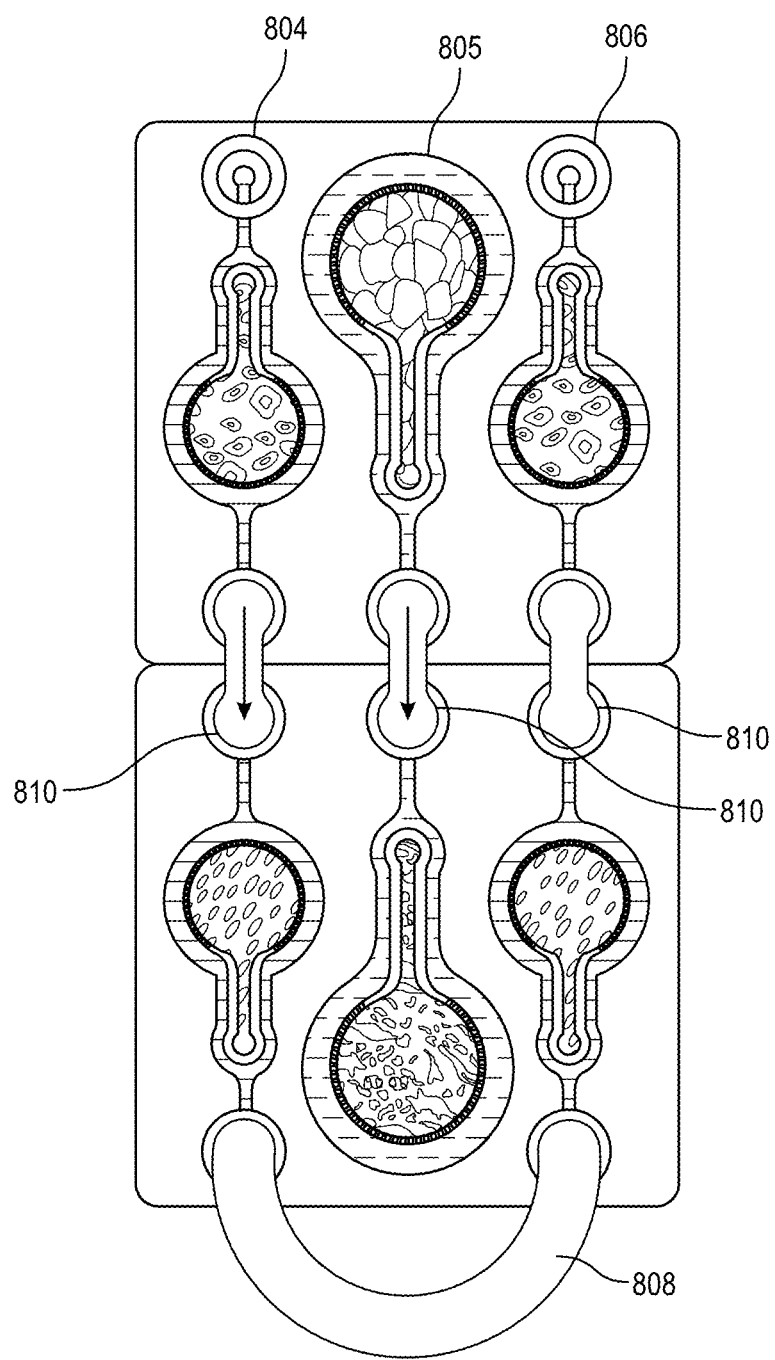

FIG. 8A and FIG. 8B show another configuration where bridging channels link two chambers either within the same microfluidic device or another external microfluidic device. FIG. 8A Top figure shows the two systems (802) are disconnected and within each system the cells are initially cultured separately. Bottom: After cell differentiation/maturation, the two systems (802) can be connected through external bridges (803) to enable organ-organ crosstalk. FIG. 8B shows top view of the connected system showing the possible routes of cell-cell communications. The figure clearly shows the cell growth chambers 805, inlet 804, outlet 806 abridging section 810 connecting two cell growth chambers a bridging section 808 to connect the entire system.

Figure 9A:
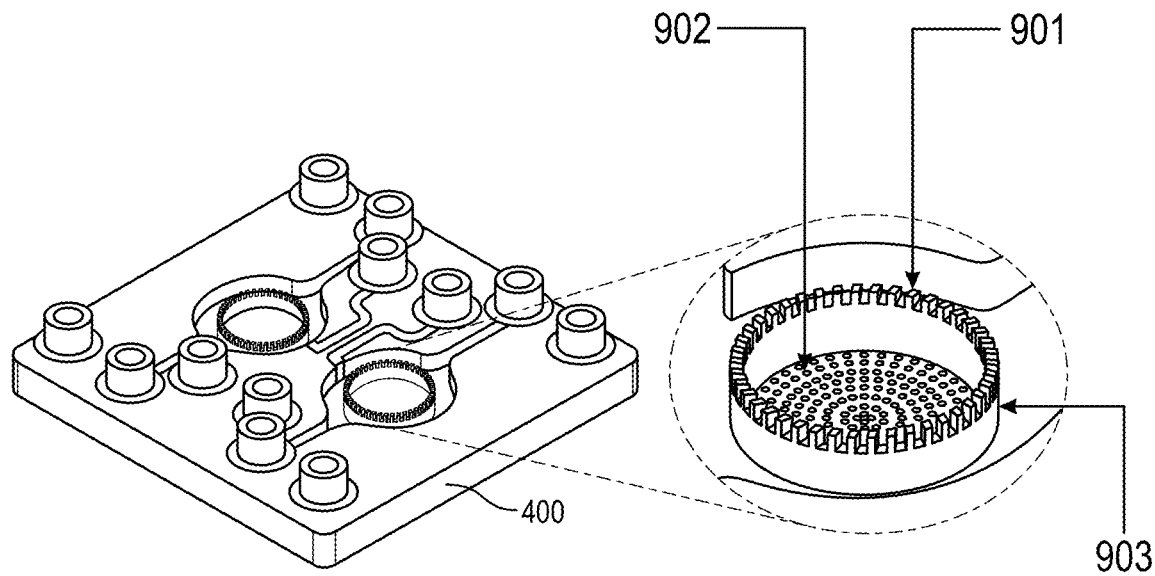
FIG. 9A, FIG. 9B, FIG. 9C and FIG. 9D show vertically stacked fluidic chambers from different angles.
Figure 9B:
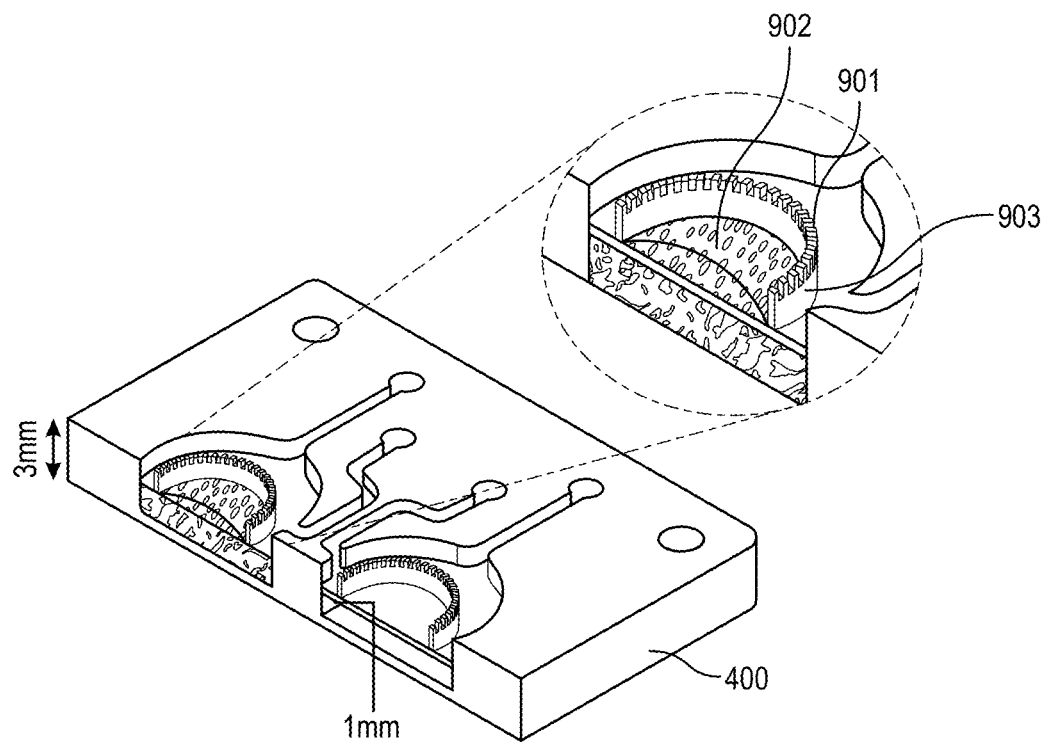
Figure 9C:
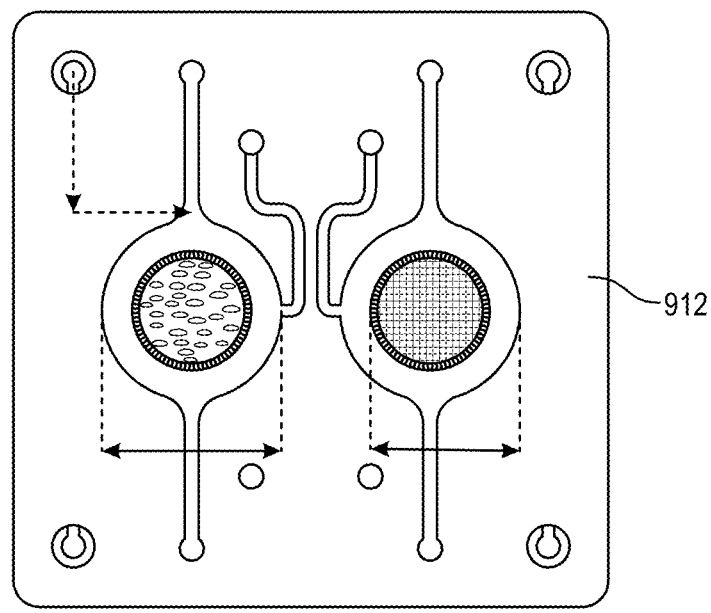
Figure 9D:
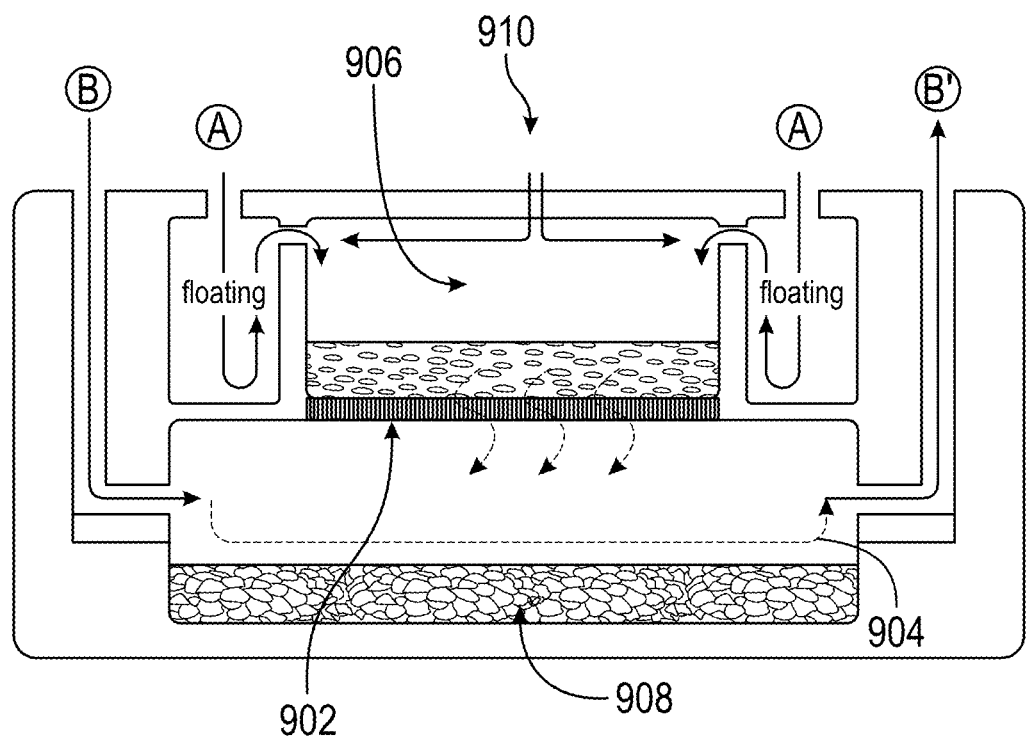

FIG. 9A shows a view of two vertically stacked fluidic chambers on a modular microfluidic device 400. The bottom surface of the top chamber is a porous membrane 902 with thickness within the range of 1 µm to 200 µm and pore size within the range of 0.4 µm to 50 µm. The circular chamber is surrounded by a feeding chamber and the two concentric chambers (the central and feeding chambers) are separated by a SPW 903 with pore size of 1 µm to 50 µm having the pores 901 are located on the upper side of the SPW. FIG. 9B shows a cross-sectional view of the microfluidic device. Underneath the porous membrane is another chamber that is perfused through dedicated channels. FIG. 9C shows a top view of the microfluidic device 912 with a total dimension of 50 mm*50 mm and concentric wells are 15 and/or 9 mm in diameter and thickness of the microfluidic device may be 1 mm. FIG. 9D shows a detailed cross-sectional view of the microfluidic device with possible fluidic flow directions 910, hence the crosstalk between the two cell cultures. For instance, an epithelial layer can be grown on top of the membrane within the upper chamber and another cell type (908) is grown in the lower cell growth chamber 904.

Three-dimensional organization: To improve cell-cell or tissue-tissue crosstalk, the fluidic chamber can be constructed with a porous basal membrane 902. In this structure, a porous membrane with optimized thickness and pore size can be used to physically separate two or more cellular structures. The porous basal surface is particularly crucial which can serve as a substrate to cultivate epithelial/endothelial/epidermal cells that enable mimicking the structure and function of the key biological barrier such as the small intestine, lung parenchyma, skin and blood vessels which generally control the interaction of the body with drug, food and environmental exposure. The compartments under the porous membrane can host another cell type as a model of a specific organ such as the liver, adipose, muscle, bone, etc. This structure can be used to recapitulate the transport (absorption and distribution) of bioactive materials or drug through the epithelial and measuring the bioavailability of these substances in the target organs and its metabolic profile. Another example, the same lower compartment can be used to model the activation of the immune system after the transport of a foreign substance through epithelia. Immune cells can be continuously perfused through the lower/basolateral compartment to mimic the circulating immune cells in vivo. By utilizing both the planner and vertical porous structures, complex heterotypic cellular organization can also be realized.

Figure 10A:
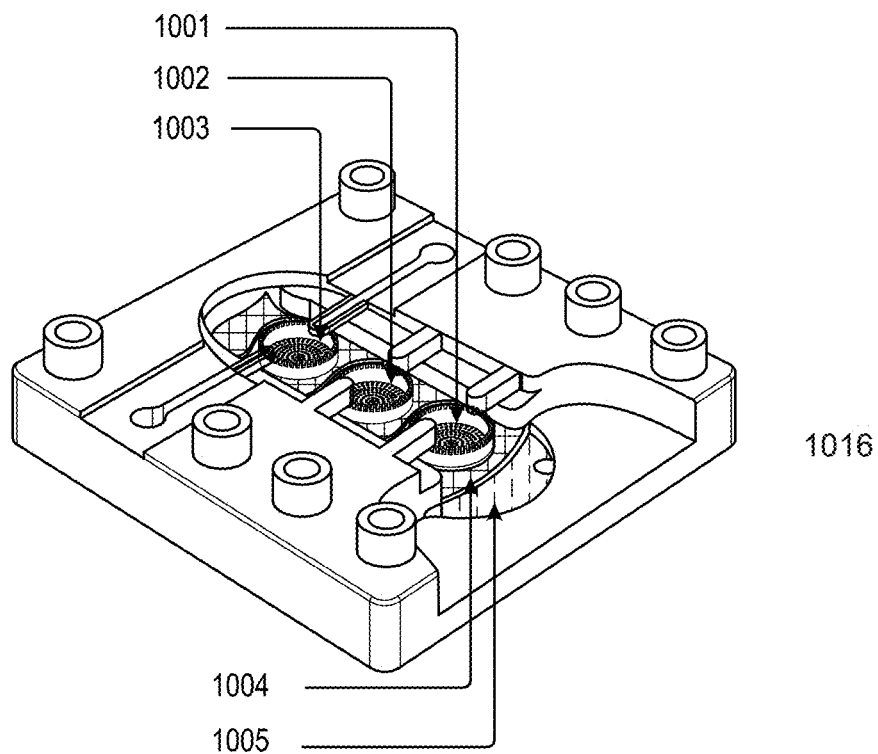
FIG. 10A, FIG. 10B, FIG. 10C, FIG. 10D, FIG. 10E and FIG. 10F shows a lower and upper chambers with membranes and fluidic flow configurations of a modular microfluidic device.
Figure 10B:
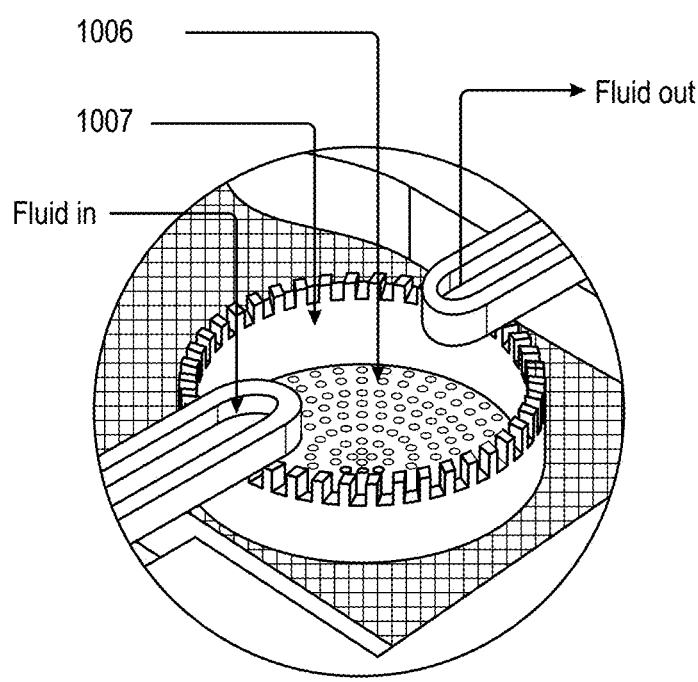
Figure 10C:
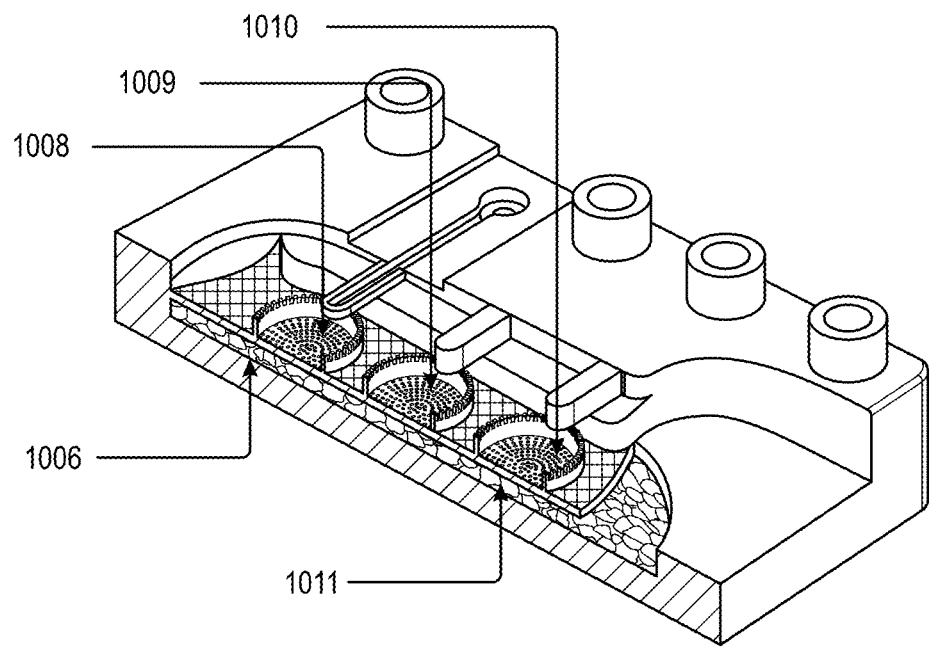
Figure 10D:
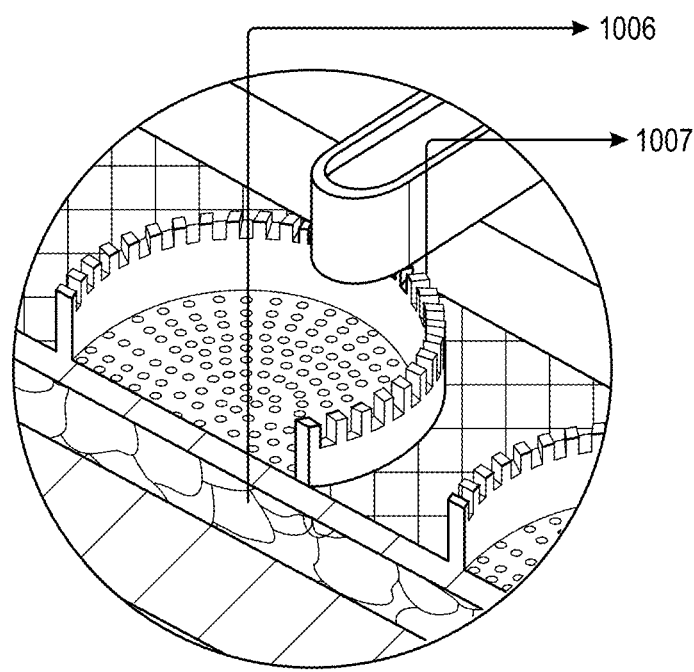
Figure 10E:
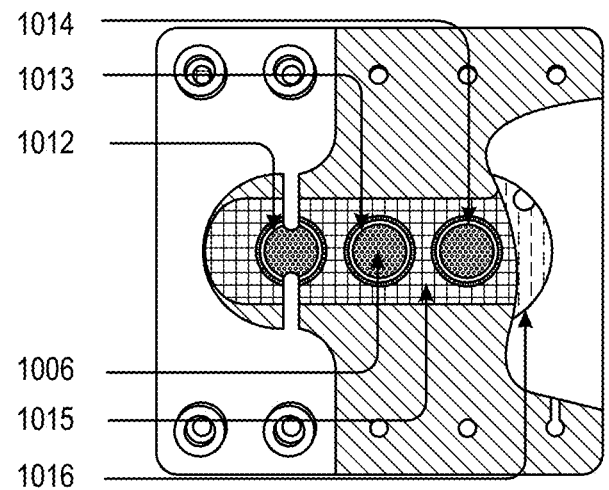
Figure 10F:
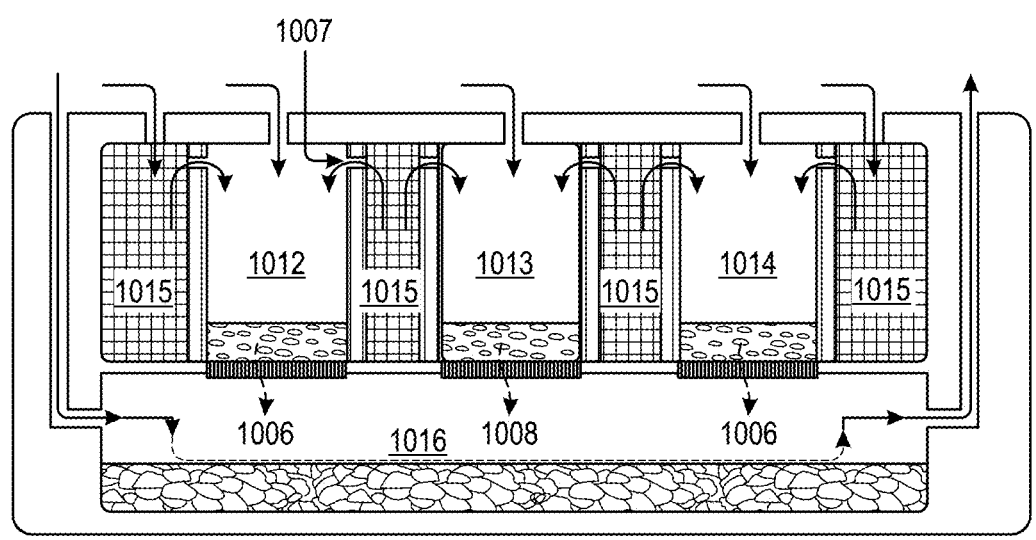

FIG. 10A shows three-side by side porous upper chambers (1001, 1002, 1003) i.e., with porous membrane bottom 1004 and surrounded by porous walls. Three upper chambers with bottom membrane (1004) and porous walls located in one feeding chamber 1016. The porous membrane is interfaced with a lower chamber (1005) that overlap with the three chamber. FIG. 10B shows an enlarged view of a single upper chamber. FIG. 10C shows a cross-sectional view of device showing all components. FIG. 10C shows a detailed 3D cross-sectional view of the device. FIG. 10D shows a cross-sectional view of a single upper chamber and the lower chamber with porous membrane 1006 and SPW 1007. FIG. 10E shows a top view of the device with clear cut of top parts for better visualization. Upper chamber 1012, 1013 and 1014 are shown. Porous membrane 1006 feeding chamber 1015 and lower chamber 1016 are shown too as a configuration. FIG. 10F shows a detailed 2D cross-sectional view of the device with possible cell culture configuration and flow directions. The three chambers (1012, 1013 and 1014) are located within one common feeding chamber (1015). Underneath the membrane there is a larger lower chamber (1016) that overlaps with all the upper chambers. The upper chamber and lower chambers can crosstalk through the porous membrane (1006, 1008) while the upper chambers located within the feeding chamber can crosstalk through the SPWs FIG. 10f. The three upper cell growth chambers (1012, 1013 and 1014) can host in vitro models of epithelial barriers such as the small intestine, lung and skin which are the major gates for the entry of food, drugs, and exogenous factors. The lower chamber can serve as an acceptor chamber (1016) which can host a variety of tissue models such as liver, bone, immune cells, etc (1018). In between cell growth chambers feeding chambers are shown cross sectional as 1015. The flow is depicted by arrows 1007.

Trans-Epithelial Electrical Resistance (TEER) setup (TeerMicrofluidic device): A microfluidic device with two upper chambers and one common lower chamber separated by a porous membrane. The design enables fluidic crosstalk between the two upper chambers through the porous membrane. Four-electrode system are positioned to be in direct contact with the fluid inside the upper chambers with two are connected to a voltage source and two connected to electric current meter (a) overall view of the device (b) cross-sectional view of the device showing the three chambers. (c) Cross-sectional view of the device shown the electrode positioning and ion transport. The key characteristics of the inner gastrointestinal tract epithelium, blood vessel endothelium, and skin epidermis include the primary structure, consisting of strongly expressed intercellular tight junctions (TJs) between epithelial/endothelial/epidermal cells (ECs). Due to the crucial role of the TJs in in-vitro drugs/nutrients transport experiments, reliable measurement techniques become necessary to assess the epithelial barrier integrity and investigate the impact of drugs/nutrients on the TJs and consequently on health. Current techniques are mainly based on the measurement of the trans epithelial electrical resistance (TEER) of barrier forming cells grown on porous membranes using two sets of electrodes that are connected to a volt-ohmmeter. This non-invasive method can be applied to living cells without markers and allows them to be monitored during growth and differentiation. The TEER reflects the resistance to the passage of ions through the physiological epithelial barrier and is recognized as one of the most accurate and sensitive measures of epithelial integrity and permeability. Current techniques of integrating TEER measurement electrodes into microfluidic systems do not provide technical basis to perform time-resolved TEER measurements to continuously monitor the integrity of the epithelium. Here, an integrated three-dimensional set of electrodes that access the apical and the basolateral sides of the epithelial cell layer is realized.

The electrical behavior of a cell/cell layer is frequency dependent. The cell membrane is a poorly conducting lipid bilayer and at low frequencies, the cell behaves as an insulator. As the frequency increases, the electric field lines penetrate the cell so that the cytoplasmic resistance of the cell can be probed. Therefore, the frequency-dependent impedance measurements would provide a wealth of information not only about the cell layer integrity but provide information about the molecular pathway of transported bio/chemical substances through the monolayer because impedance measurements allow for the separation of paracellular resistance (governed by TJ properties) from transcellular resistance (determined by conductive structures residing in the cell membranes).

Figure 11A:
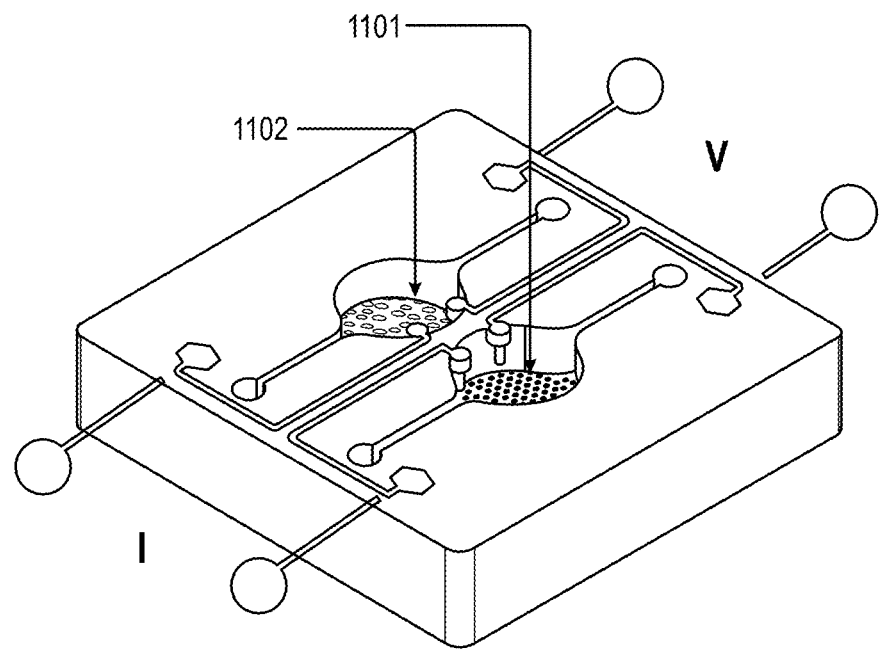
FIG. 11A, FIG. 11B and FIG. 11C shows a modular microfluidic device with two chambers separated by a porous chamber and two set of electrodes positioned at both sides of the membrane FIG. 12A, FIG. 12B, FIG. 12C, FIG. 12D
Figure 11B:
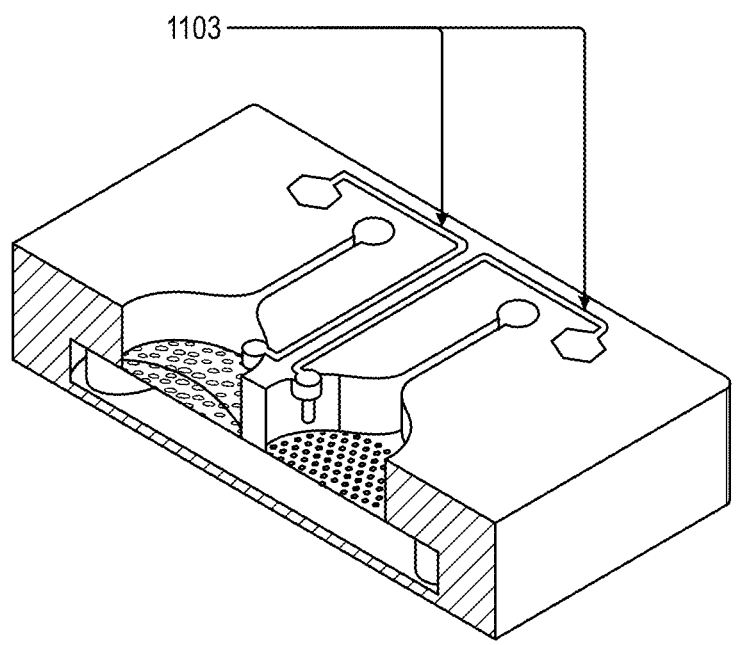
Figure 11C:
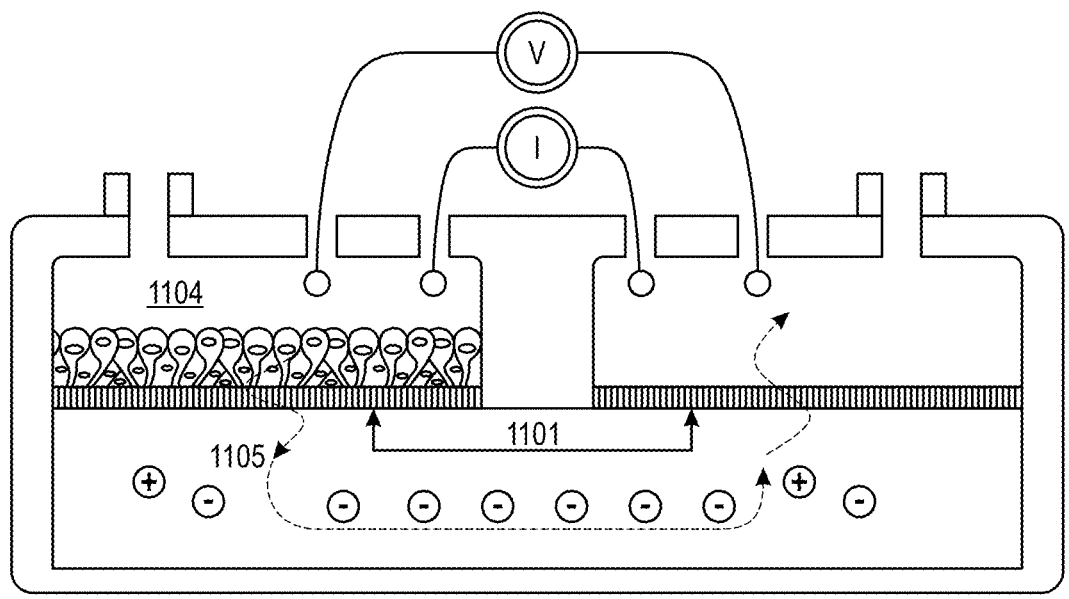

FIG. 11A and FIG. 11B shows a device with two upper chambers (1101,1102) and one common lower chamber separated by a porous membrane. This design enables fluidic crosstalk between the two upper chambers through the porous membrane. FIG. 11b shows four-electrodes system (1103) are positioned to be in direct contact with the fluid inside the upper chambers with two are connected to a voltage source and two connected to electric current meter. Measuring the TEER of an epithelial tissue (1104) within a microfluidic device requires positioning of two sets of electrodes, one facing the apical (upper) side of the epithelial layer and the other set facing the basolateral (lower) side. In the current state of art, accessing the lower chamber is done through a hole in the bottom which renders the device structure cumbersome especially during the microscopic imaging. In our design, the electrodes access the apical and basolateral chambers from top via the two membranes (1101) and the lower chamber (1105). FIG. 11b and FIG. 11c show cross-sectional views of the device which illustrate in detail the combination of the 3d-perfusion with TEER measurement.

Materials and Methods: PMMA sheets with thicknesses of 0.5 mm, 1 mm and 2 mm were purchased from a local vendor. Double-sided adhesive (3M 467MP Adhesive Transfer Tape Acrylic 2.3 mil) is from 3M (Saint Paul, MN, USA). 3D printing resin (DentaGuide) from Asiga (NSW, Australia). Human colorectal adenocarcinoma cells (Caco-2) are from American Type Culture Collection (ATCC) (Manassas, VA, USA). Poly-L-lysine (PLL) solution, 0.1% (w/v), collagen (type 1, rat tail) and Trypsin/EDTA were purchased from Sigma Aldrich (Burlington, Massachusetts, USA). Dulbecco's Modified Eagle Medium/Ham's F-12 (DMEM/F12) containing 10% (v/v) fetal bovine serum and 1% penicillin-streptomycin antibiotic was purchased from Gibco., human pre-adipocytes (HPAd) cat #802s-05a, pre-adipocyte growth medium, adipocyte differentiation medium, adipocyte maintenance medium, and adipocyte starvation medium from Cell Applications (USA); iMDM medium from Thermo Fisher Scientific (USA); Lipid A (LPA) from $E.\ coli$ serotype R515 (TLR grade) from Alexis Biochemical (SA, USA); TNF-α, IL-6 and IL-8 ELISA kits, CD11b-FITC (clone ICRF44), CD45-PE (clone: 2D1), CD3-PerCP-Cy5.5 (cline: HIT3A), CD19-PE-Cy7 (clone: calceine-AM from ThermoFisher Scientific (USA); 2-NBDG glucose uptake cell-based assay kit from Cayman Chemical (USA); Hoechst 33342 from Molecular Probe (OR, USA); Bradford reagent and 0.4% trypan blue, metformin hydrochloride and docosapentaenoic acid (DPA) from Sigma Aldrich (USA); Other chemicals were of analytical grades from Sigma Aldrich (USA).

Figure 12A:
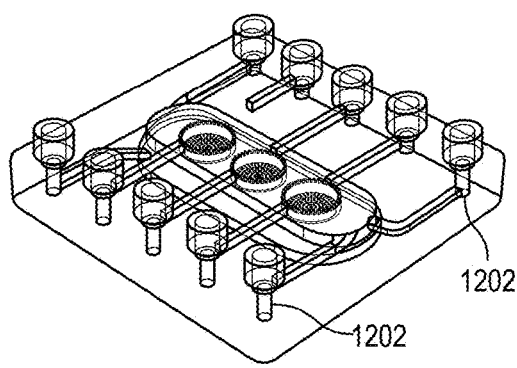
FIG. 12E shows a 3D design of the modular microfluidic device and an optical image of the fabricated device.
Figure 12B:
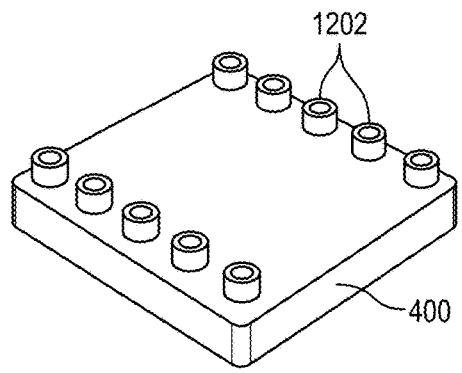
Figure 12C:
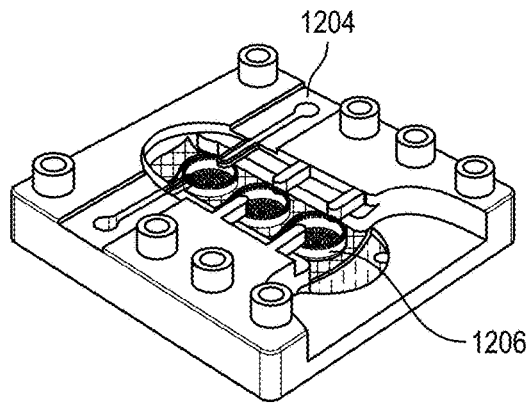
Figure 12D:
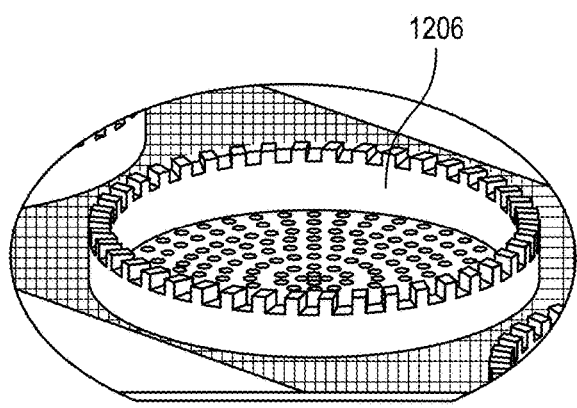
Figure 12E:
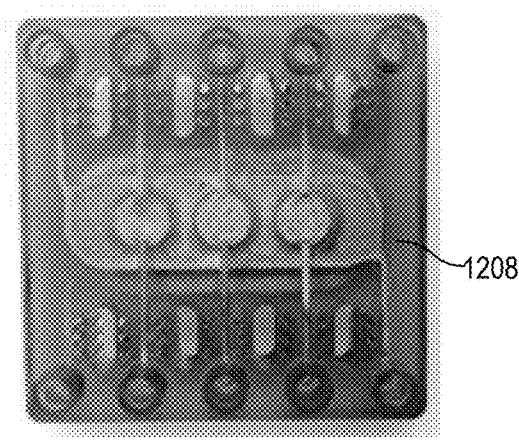

Fabrication: The microfluidic systems can be fabricated using a variety of micro fabrication techniques including silicon micromachining, soft lithography, injection molding, 3D printing and laser machining. FIG. 12A shows the 3D design of the microfluidic device with inlet port 102. FIG. 12b shows the fabricated microfluidic device with inlet ports. FIG. 12C shows detailed view of the fabricated modular microfluidic device with cell growth chambers with porous membrane 1206 and microfluidic system 1204. FIG. 12D shows a detailed view of one upper chamber with the porous structures (membrane and walls 1206). FIG. 12E shows an optical image 1208 of the fabricated modular microfluidic device. Here we will briefly describe the fabrication process of one system as an example using a combination of 3D printing and laser machining techniques. The device was designed using SolidWorks software (Dassault Systèmes, Vélizy-villacoublay, France). In one scenario, the entire microfluidic microfluidic device can be 3D printed as shown in FIG. 12A. The microfluidic device is fabricated using Digital light processing (DLP)-based 3D printer (ASIGA MAX UV 3D printer, NSW, Australia). DLP-based 3D printing uses a projected light source to cure a photopolymer resin and create 3D objects. The DLP 3D Printer comprises four main components: The Digital Light projector, the light source for the DLP 3D printer which projects the image of each layer onto the resin, the Digital Micromirror Device (DMD) made up of thousands of micromirrors and helps navigate the light beam projected by the digital light projector, and the Vat (Resin Tank) which holds the liquid photopolymer resin. It has a transparent bottom to allow the projected light to reach and cure the resin, and the Build Plate which is the surface onto which the printed objects adhere during the printing process. The process begins with a 3D model, which is prepared using slicer software (Asiga composer). This software slices the 3D model into hundreds/thousands of layers, creating a PNG stack of images. Then the 3D model file is uploaded to the DLP printer, and the resin is poured into the vat. The build platform is lowered into the resin, leaving a small space between the vat's bottom and the build plate. The digital light projector flashes an image of each layer onto the vat's bottom, curing the resin and forming the first layer. The build platform then moves up one layer in height, and the process is repeated until the entire part is printed.

Figure 13A:
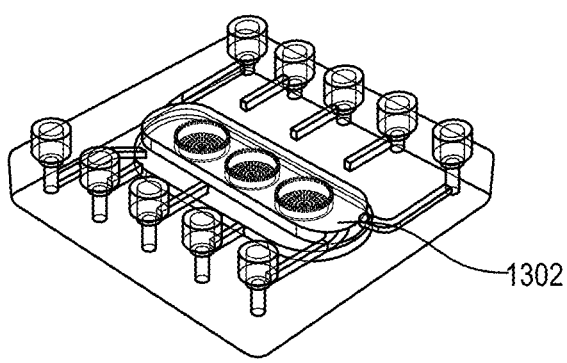
FIG. 13A, FIG. 13B, FIG. 13C, FIG. 13D and FIG. 13E shows another version of the 3D image of the microfluidic device.
Figure 13B:
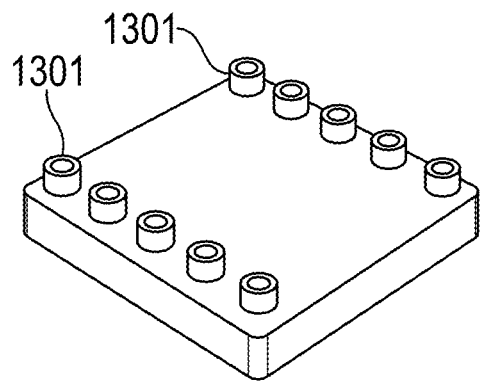
Figure 13C:
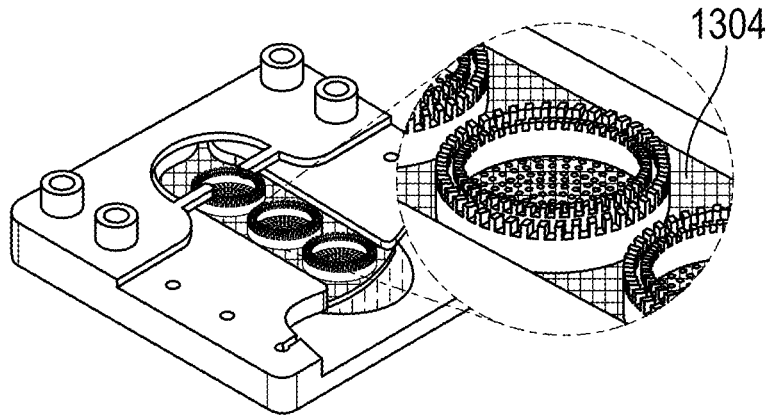
Figure 13D:
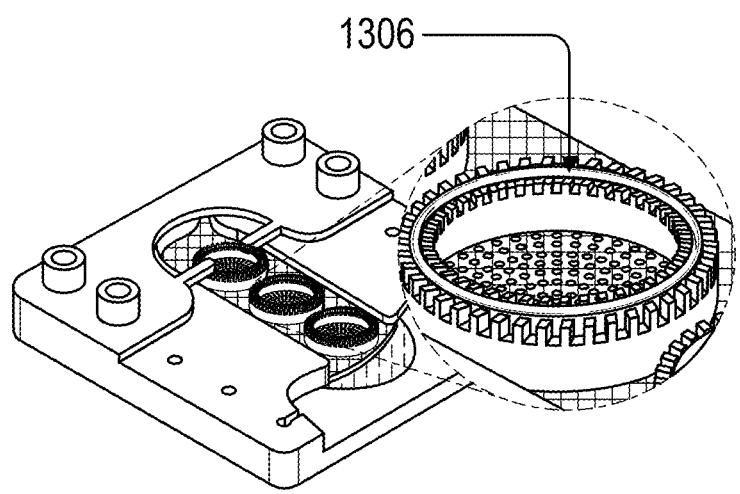
Figure 13E:
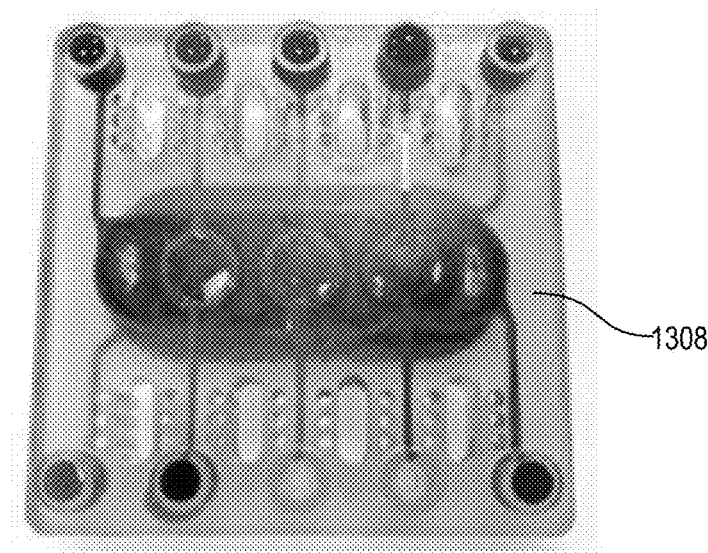

FIGS. 13A. 13B. 13C. 13D and 13E shows another version of the 3D image of the microfluidic device. FIG. 13A shows the fabrication process of a similar modular microfluidic device but with a hydrogel layer included between two porous walls 1306. In the 3D printing part, the 3D drawing was transformed into a STL file and transferred to the 3D printer (ASIGA MAX UV 3D printer (NSW, Australia)). The laser cut part was transformed to a DXF file and transferred to a CO2 laser cutter (Beambox, Flux, Taipei, Taiwan). A variety of biocompatible materials can be used including poly (methyl methacrylate), Polystyrene (PS), PET membranes, polydimethylsiloxane (PDMS), glass, and a variety of 3d printable resins. FIG. 13B shows the fabricated microfluidic device with inlet ports 1301. FIG. 13C shows a detailed view of the fabricated microfluidic device (without gel) 1304. FIG. 13D details a view of the fabricated microfluidic device (with gel) 1304. FIG. 13E shows an optical image of the fabricated device 1308.

Figure 14:
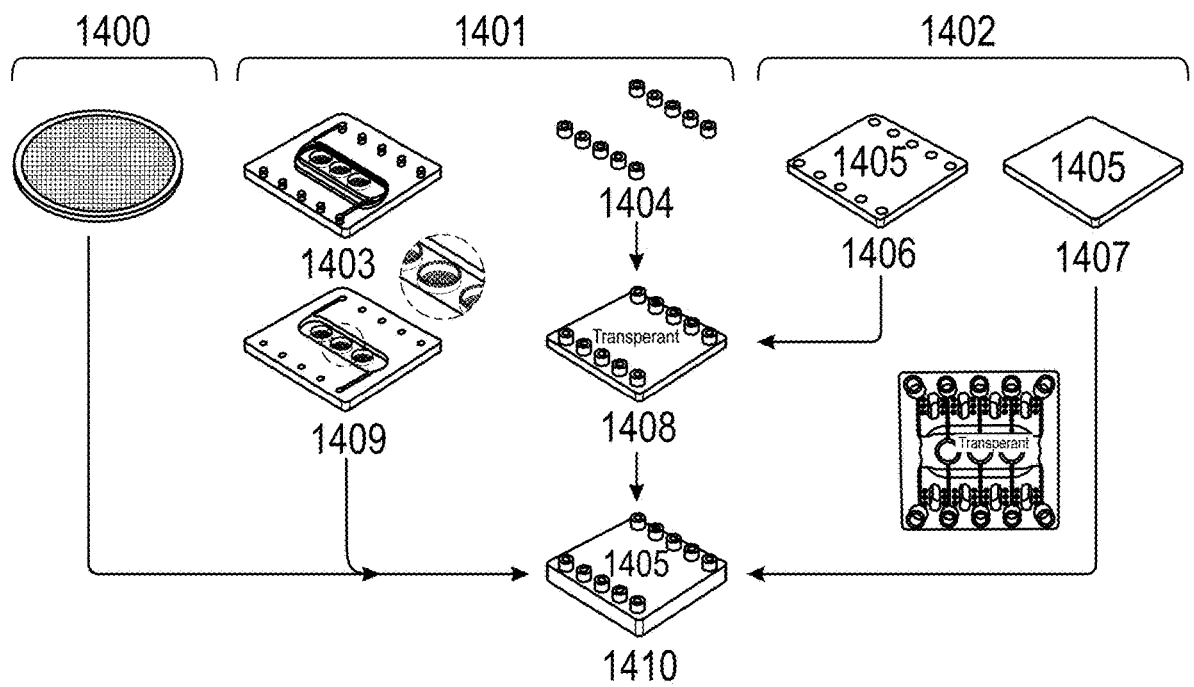
FIG. 14 shows a multi-compartment device with planner and vertical porous structures being fabricated using 3D printing technique.

To enable better imaging of the cells within the microfluidic device, the bottom and top layers of the microfluidic device need to be glassy clear and transparent. In this scenario, a major part of the microfluidic device with SPWs can be fabricated using the 3D printing technique while the top and bottom layers can be fabricated of PMMA or other transparent material and assembled as shown in FIG. 14. The porous membrane, either from a commercial source or separately fabricated, with the desirable pore size and thickness can be assembled as well (FIG. 14). FIG. 14: The major (middle) part of the microfluidic device with SPWs can be fabricated using the 3D printing technique while the top and bottom layers can be fabricated of PMMA or other transparent material and assembled as shown. The porous membrane, either from a commercial source or separately fabricated, with the desirable pore size and thickness can be assembled as well. FIG. 14 shows a Porous membrane 1400, 1401: The 3D printed part, 1402: The laser cut part, 1403: The 3D printed main fluidic device without top cover, 1404: 3D printed tubing holders, 1405: fluidic ports, 1406: Top transparent cover (laser cut), 1407: Bottom sheet, 1408: The tube holders assembled to the top cover, 1409: The 3D printed fluidic device coated with UV-curable resin, and 1410: The fully assembled device.

The device comprises two components: 3D printing and laser cutting. The process began with 3D printing the main part of the fluidic device, which includes the fluidic chambers, channels, porous walls, and porous membrane. The top and bottom covers were fabricated using the laser cutting technique. Hollow cylindrical tube holders (1404), which were 3D printed, were assembled to the top cover (1406). This cover contains the fluidic port that facilitates liquid injection into the device and sample collection. A thin layer of UV-curable resin (1409) was applied to the top and bottom surfaces of the main 3D printed part (1403). The top and bottom covers were then assembled to the main fluidic part and cured under UV light, resulting in a fully sealed microfluidic device (1410).

Figure 15A:
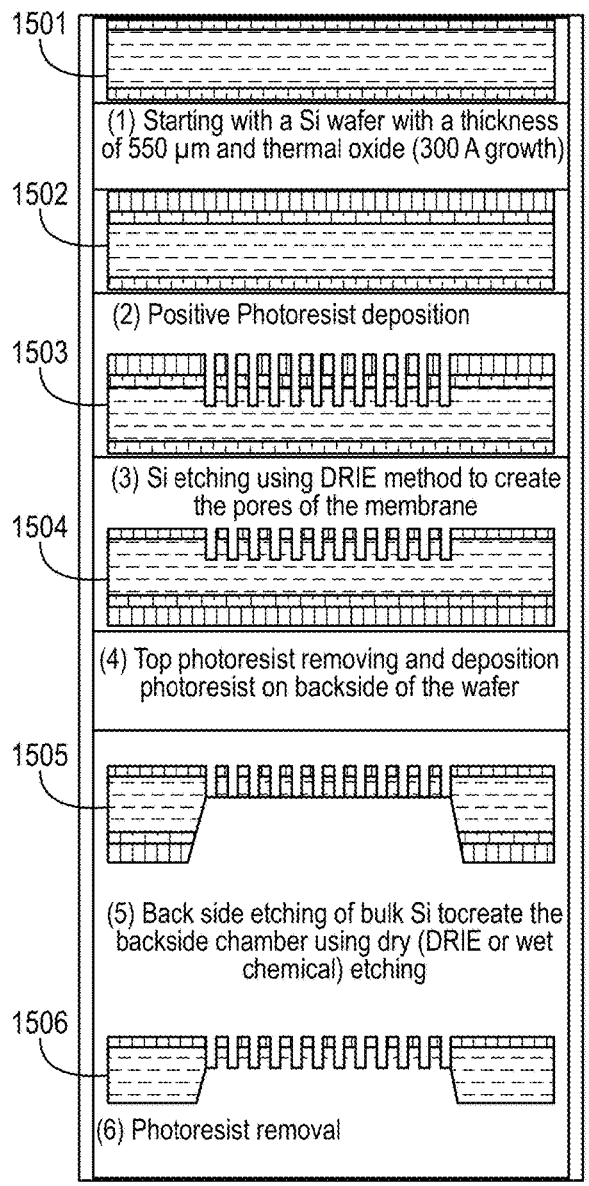
FIG. 15A, FIG. 15B, FIG. 15C, FIG. 15D, FIG. 15E and FIG. 15F shows fabrication of porous membrane and porous wall structure in silicon.
Figure 15B:
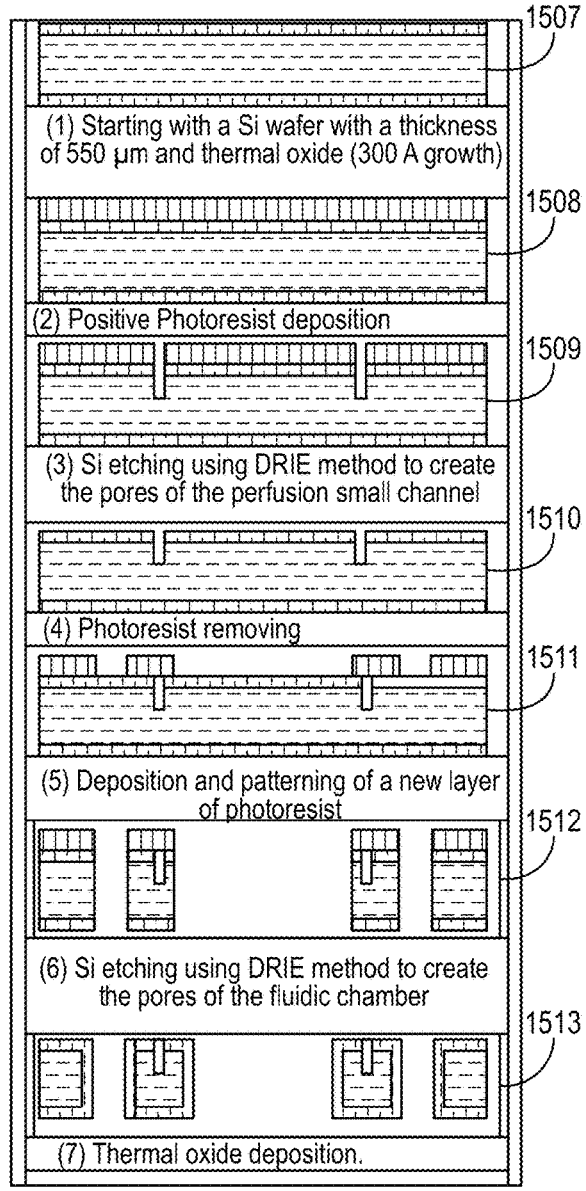

Si microfabrication technology provides powerful means to realize nano- and micro-scale features necessary to fabricate the microfluidic system. Particularly, it provides tools to realize the desired pores size of the planar membrane and SPWs. Here, we describe the fabrication process of one modular microfluidic device using Si microfabrication combined with polymer bonding technique to realize a hybrid system with dimensions smaller than the single cell size (FIG. 15A and FIG. 15B). FIG. 15a: A 300 Å thermal oxide was deposited on both sides of Si wafer 1501. The oxide layer acts as a masking layer and protects the rest of the substrate during the etching of the pores. The wafer then was coated with a thin layer of positive photoresist 1502 to prepare for the photolithography. Deep reactive-ion etching (DRIE 1505) was employed to etch the wafer to create the pores with diameter of 1 µm. Then the photoresist was removed 1506, and the wafer was cleaned. Another photoresist was coated on the backside of the wafer to prepare for the second lithography step 1504. A backside cavity was realized by wet etching using potassium hydroxide (KOH) and tetra-methyl-ammonium hydroxide (TMAH). Lastly, the individual microfluidic devices with membrane were released by wafer dicing with microfluidic device dimensions of 40×15 mm.

Figure 15C:
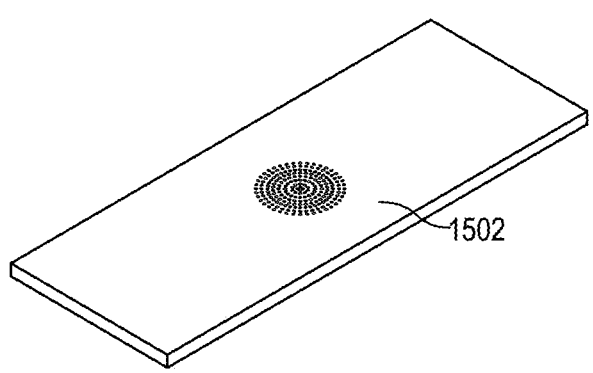
Figure 15D:
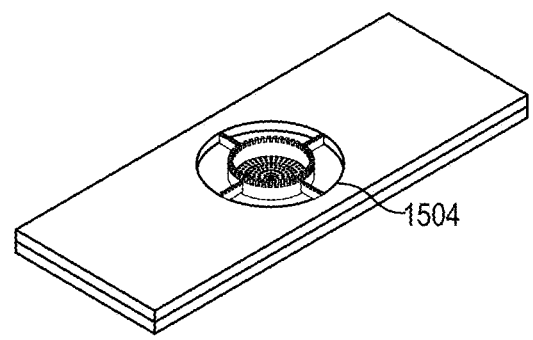
Figure 15E:
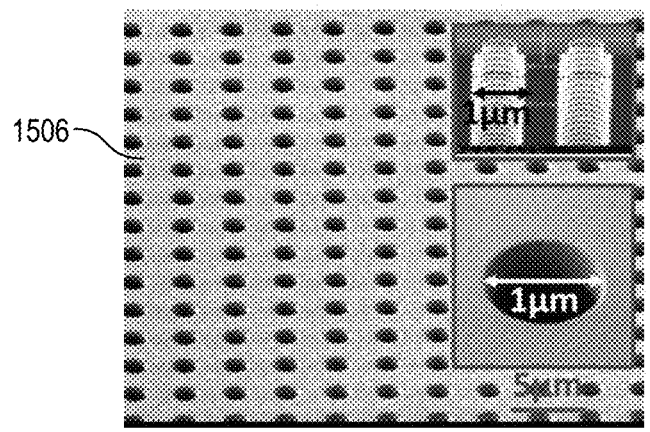
Figure 15F:
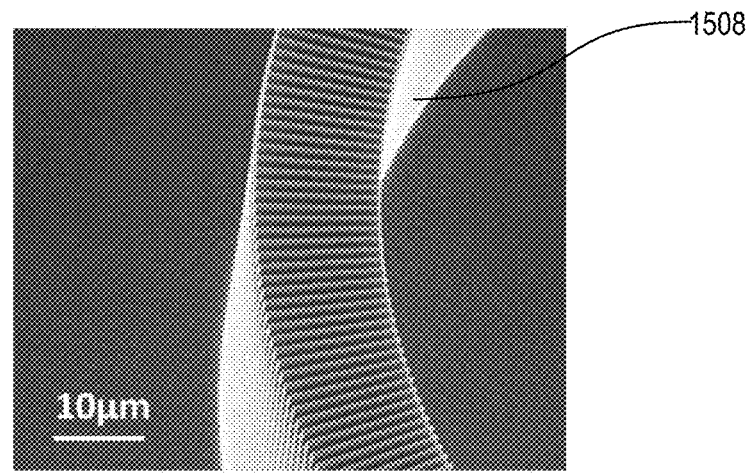

FIG. 15*b*: A bilayer of silicon oxide was deposited on Si substrate with a thickness of 300 Å (1507). A thin layer of positive photoresist was deposited on top of the Si wafer 1508. Using the deep reactive ion etching (DRIE) technique, shallow trenches with width, length and depth of 5 µm, 50 µm and 5 µm, respectively, were created to form the microchannel array of the porous barriers between the fluidic compartments 1509. Then the photoresist was removed 1510. A new photoresist was deposited and patterned 1511. Afterwards, wide and deep trenches, with a depth of 200 µm, were etched using DRIE to form the fluidic compartments as well as the fluidic inlets/outlets 1512. The fluidic inlets and outlets were opened by further backside wet etching such that the fluidic port would be accessed through the backside of the microfluidic device. Following this, a thermal oxide layer 1513 was grown on both sides of the wafer. Finally, the silicon wafer was diced to individual microfluidic devices with dimensions of 40×15 mm. FIG. 15C shows the final product of the fabrication 1502 steps explained in FIG. 15A (i.e. a Si substrate with the porous membrane). The dimensions are 40 mm in length and 15 mm in width. The center chamber has a diameter of 5 mm and pore size is 0.5 µm. FIG. 15D shows the final product of the fabrication steps explained in FIG. 15B (i.e., the upper apical chamber). FIG. 15E shows a scanning electronic microscope (SEM) image of the fabricated membrane with cross-sectional view and enlarged view in the insets. FIG. 15F shows a scanning electronic microscope (SEM) image of the fabricated porous wall 1508.

Figure 16B:
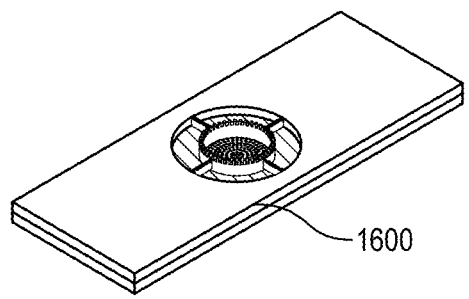
Figure 16C:
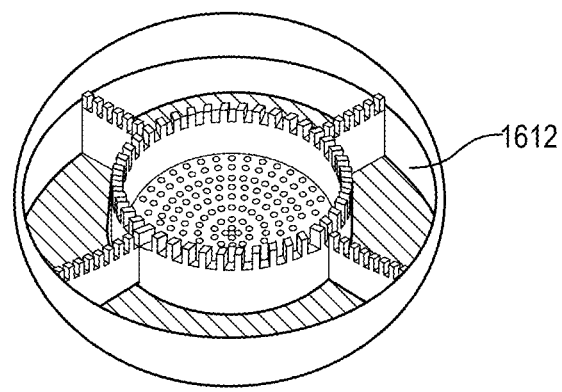
Figure 16D:
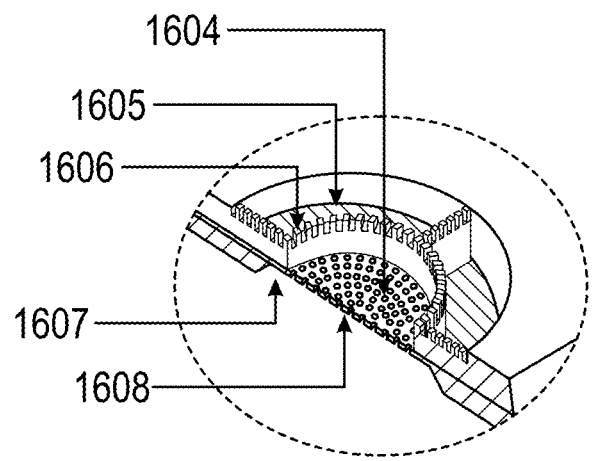

FIG. 16A shows the porous membrane Si layer 1601 coating process in preparation for bonding with the upper layer. The membrane layer was coated with a thin layer of PDMS 1602. Prior to the PDMS layer deposition, the membrane was covered with a protection cover to prevent micro-pore blockage (1602). After PDMS deposition, the cover was removed (1610) and the two parts (the membrane layer and upper layer) were brought together and bonded at a temperature of 70° C. for three hours 1600 (FIG. 16*b*). It should be noted that a variety of bonding techniques can be used such as thermal (with various boding polymers) and anodic bonding. FIG. 16B shows a 3D schematic of the two bonded layers and FIG. 16C show detailed view of the bonded structures 1612. FIG. 16D shows the resulting structure comprises two vertically stacked shallow chambers 1604 and 1607 separated by a porous membrane 1608. The upper chamber 1604 is surrounded with a SPW 1606. The fabricated membrane has a pore size of 500 nm with a porosity of ~ 50% and the fabricated SPW has perfusion channels with width, height, and length of 3 µm, 10 µm and 50 µm. At this stage the structure is open at the top and bottom.

Figure 17A:
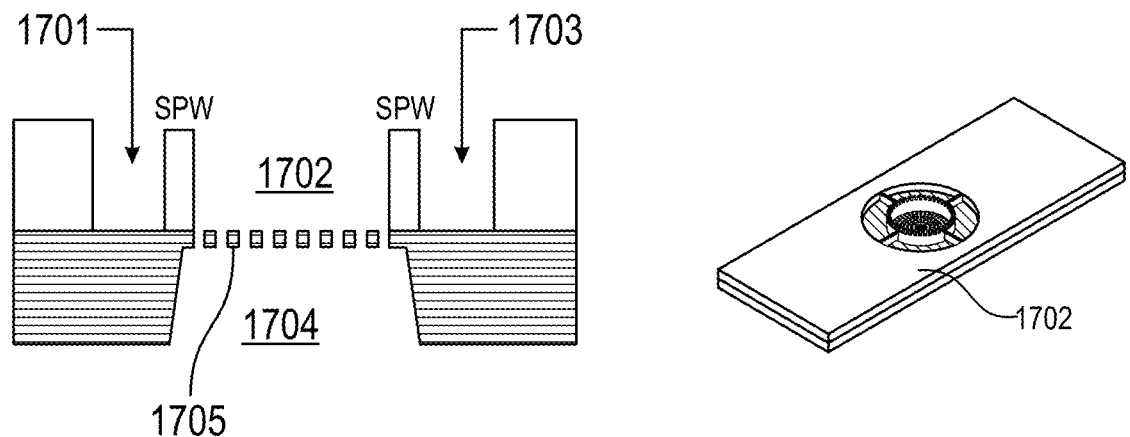
FIG. 17A, FIG. 17B, FIG. 17C, FIG. 17D and FIG. 17E shows a COMPOS unit in a customized 3D printed modular microfluidic device.
Figure 17B:
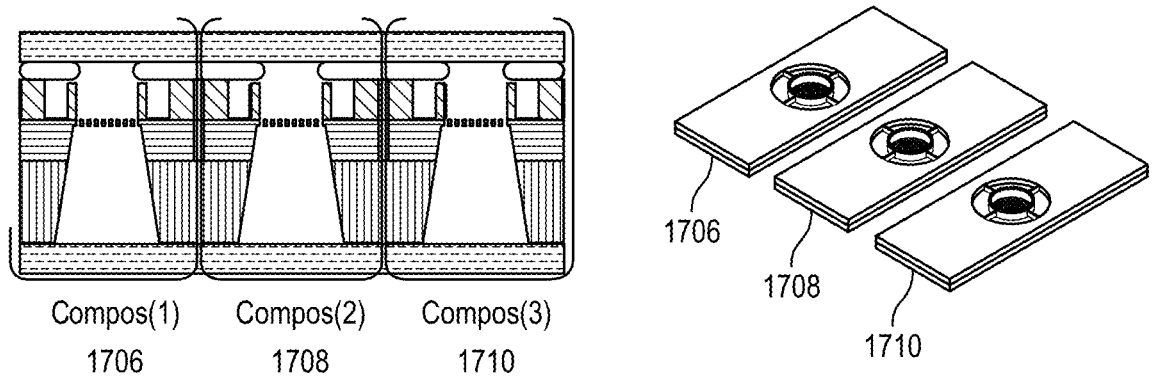
Figure 17C:
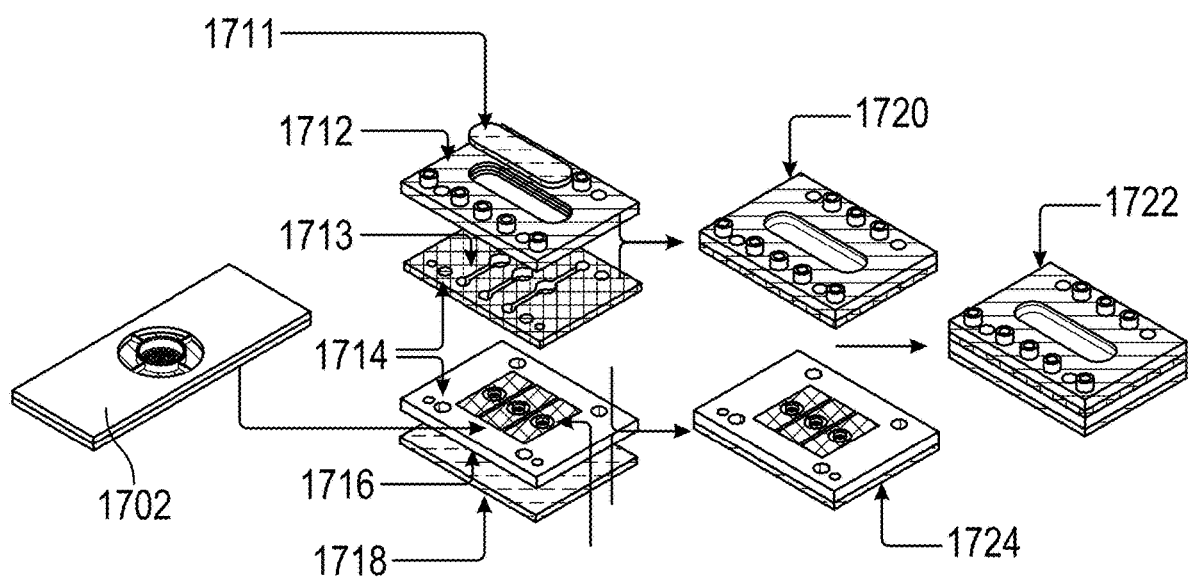

The fabricated compartmentalized porous structure described above, which from now on termed "COMPOS", would form the basic unit of a more complex fluidic structure. An individual unit of COMPOS can be used to grow 1-6 cell types in close proximity and multi-directional crosstalk as sketched in FIG. 17A. Two or more COMPOS units can be integrated together by combining them in a customized fluidic package to form a complex fluidic structure xCOMPOS (FIG. 17*b*). Three COMPOS units were assembled by encapsulating them in a custom-3D printed fluidic package (FIG. 17*c*). The fluidic packaging structure allows connecting the three lower chambers such that they become one large chamber. The three upper chambers were kept unconnected by employing an elastic ring (O-rings) which were 3D printed using an elastic resin. The fluidic package comprises the following components/layers (FIG. 17*b*):

A. Bottom layer (1718): a transparent layer which was cut out of PMMA and enables cell visualization under microscope.
B. Middle layer (1) (1716): holds the three COMPOS units. The bottom of the layer has a common channel/chamber that enables connecting the lower chambers of the three COMPOS units to become one large chamber. The top surface has three resets to accommodate and hold the three COMPOS units.
C. Middle layer (2) (1713): contains three separated chambers which are aligned to the Si upper chambers. Each chamber is linked to an inlet and outlet hole through a long channel. Under each chamber, an O-ring is fixed to ensure tight fluidic sealing of this layer with the COMPOS.
D. Top layer (1712): used to fully seal the whole structure on top. To enable light to go through during imaging, a transparent window 1711 was cut of PMMA and fixed within the center of the layer.

Figure 17D:
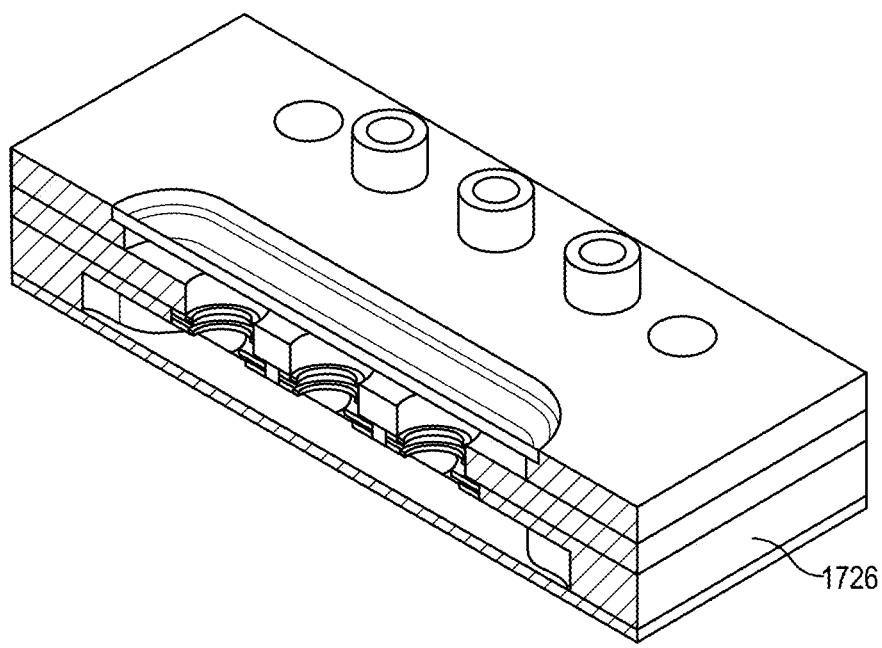
Figure 17E:
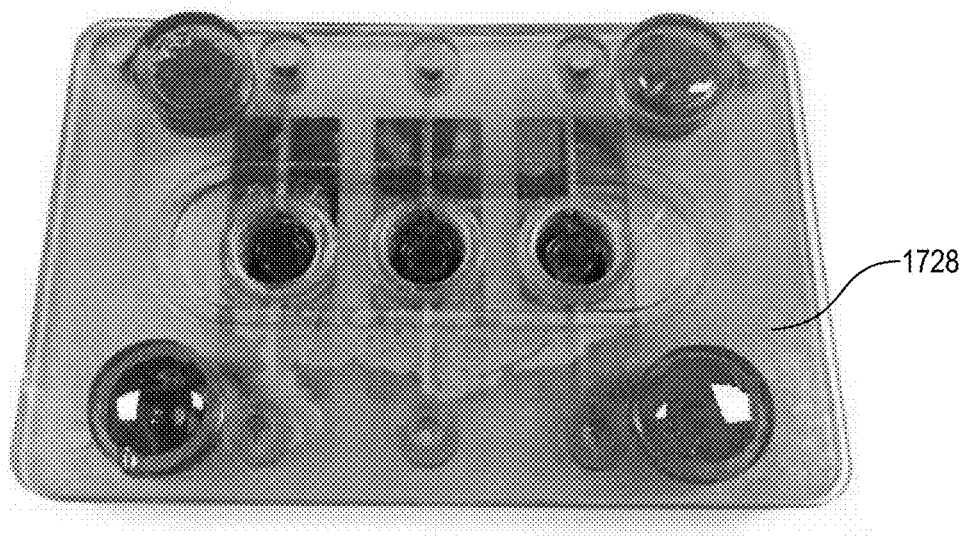

The bottom and middle layer (1) were bonded together using UV-sensitive resin to form Part 1 (P1) 1724, and the top and middle layer (2) were also bonded together to form part 2 (P2) 1720 (FIG. 17*c*). P1 and P2 are clamped together using a set of magnets 1714 which were pre-fixed within the middle layers. FIG. 17*d* shows a cross-sectional view of the packaged xCOMPOS 1726 and FIG. 17*e* shows an image 1728 of the fabricated system. The xCOMPOS can be used as a template for organization a variety of cell type assembly to recapitulate the anatomical structure of a specific organ or multi-organs that mimic the cell-cell or tissue-tissue crosstalk.

TABLE 1

Table 1 lists the dimensions of the important features of the system as well as the range within which the system can be fabricated.

| Feature | Fabricated feature | Feasible Range |
| --- | --- | --- |
| Fluidic chamber dimensions | 1000 µm-20,000 µm | 50 µm-100,000 |
| Fluidic channel (width, Depth) | 200 µm-1000 µm | 20 µm-2000 µm |
| Thickness of the wall separating the fluidic chambers | 50-100 µm | 10 µm-1000 µm |
| Perfusion channel dimensions (width, depth) | (2 µm, 5 µm), (5 µm, 5 µm), (50 µm, 50 µm) and (100 µm, 100 µm) | (1-200) µm × (1-200) µm |
| Perfusion channel length | 50-200 µm | 10 µm-500 µm |
| Gap between perfusion channels | 5-100 µm | 1 µm-500 µm |
| Membrane pore size | 0.5 µm, 0.8 µm, 1 µm, 2 µm and 3 µm, 50 µm | 0.5 µm-200 µm |
| Membrane thickness | 10-100 µm | 2 µm-1000 µm |

Characterization of the flow within the devices: The fluidic ports of the device were connected to a set of syringes, which are mounted on a programmable syringe pump (KDScientific, Holliston, MA, USA), through PEEK tubing with an inner diameter of 0.5 mm. To visualize the flow profile within the device, colored liquid was injected into the inlet of a selected chamber and the infusion of the liquid into the subsequent chambers monitored over time. To examine the mass transfer between adjacent chambers, the transport of FITC-dextran (4K Da) tracer through the porous barriers was monitored by injecting the tracer solution with a concentration of 10 µl/mL in a selected upstream chamber which was initially filled with phosphate-buffered saline (PBS) solution, and the fluorescence intensity due to the diffusion of the tracer was measured at different downstream check points using a fluorescent plate reader (Perkin Elmer, Richmond, CA, USA).

Cell Culture: In vitro model of the human inflamed adipose tissue (adipocyte/immune cell coculture): Prior to seeding the cells into the microfluidic device, the fluidic compartments underwent a sterilization process by filling them with 70% ethanol for a minimum of 4 hours. Afterward, the microfluidic devices were washed with deionized water, and each microfluidic device was loaded with 100 µL of Poly-L-lysine solution (0.1 mg/mL in H2O) and incubated overnight at 37° C. The microfluidic devices were then washed again, first with sterilized deionized water and then with phosphate-buffered saline (PBS). Next, the microfluidic devices were primed with a preadipocyte growth medium from (Cell Applications). A suspension of Human Preadipocytes (HpA) with a cell density of $1.5 \times 10^6$ cells/mL and cell viability above 85% was inoculated into the central compartments. The cells were allowed to attach under static culture conditions without perfusion for 2 hours in a 5% CO2 humidified atmosphere. Following cell attachment, perfusion was initiated at a flow rate of 8 nL/s. The preadipocytes were cultured under perfusion conditions until they reached confluence, which typically took around 2-3 days. To induce cell differentiation, the preadipocyte growth medium was replaced with an adipocyte differentiation medium (#811D-250, Cell Applications). After 12-14 days of differentiation, an adipocyte maintenance medium (#811M-250) was applied for at least two days before further cell characterization or co-culture with immune cells. Morphological images of the cells were acquired throughout the process. Once the adipocytes were fully differentiated, U937 cells were collected and suspended in an adipocyte maintenance medium. A 50 µL suspension of U937 cells was then inoculated into the adjacent compartment of the microfluidic device. The adipocyte maintenance medium was continuously perfused through the microfluidic device at a rate of 8 nL/s for 2-3 days. Cell viability and morphological changes were monitored using a microscope. A mixture of calcein-AM (2 µM) and ethidium homodimer-1 (4 µM) diluted in Dulbecco-PBS (D-PBS) was used to assess cell viability. To induce an inflammatory state, the cells were treated with lysophosphatidic acid (LPA) at a concentration of 100 ng/mL. Supernatants from the sampling outlet were collected for further analysis. The concentrations of Tumor Necrosis Factor (TNFα) and Interleukin-6 (IL-6) in the supernatants were measured using an ELISA method. To serve as controls, experiments were also conducted on untreated samples and adipocyte monocultures. The percentage of calcein-AM-labeled cells was used to quantify cell viability. The growth and morphology of the cells were regularly monitored under the microscope. After the Human Preadipocytes (HPADs) reached confluence, which typically took around 3-5 days after seeding, they were perfused with a differentiation medium. Lipid droplets were observed in the cells after approximately 2 days of differentiation. To assess cell differentiation of the adipocytes, the lipid content within adipocytes was monitored by staining the lipid droplets with Oil Red O (Sigma-Aldrich, St. Louis, MO, USA).

The cells were initially fixed with 4% paraformaldehyde (PFA) and subsequently treated with the Oil Red O solution for a duration of 30 minutes at room temperature. Afterward, the cells were washed with deionized (DI) water. Brightfield images were captured using a microscope.

Intestinal epithelium in vitro model: A simplified in vitro model of the human was constructed using a confluent monolayer layer of Caco-2 cells (American Type Culture Collection (ATCC) Manassas, VA) was grown on top of the porous membrane. Caco-2 cells were initially grown on 25 mL tissue culture flasks in DMEM/F-12 cell culture media with high glucose and with 10% (v/v) fetal bovine serum (FBS) and 1% penicillin/streptomycin antibiotic at 37° C., 5% CO2 in 95% relative humidity till reaching 80% confluence. Culture medium was refreshed every 24h hours and cells were harvested by passaging Trypsin/EDTA solution. The microfluidic microfluidic devices were sterilized with 70% ethanol and exposed to UV light for 1 hour. Then, the microfluidic devices were washed with deionized (DI) water and subsequently, a volume of 300 µL of a Poly-L-lysine solution (0.1 mg/mL, in H2O) was loaded into the microfluidic device and incubated overnight at 37° C. Afterward, the microfluidic devices were washed with sterilized DI water and PBS. The apical and basolateral chambers of the microfluidic device were filled with fresh culture media and incubated for 24 hrs. Then, the medium in the apical chamber was replaced with Caco2 cell suspension at a concentration of $3 \times 10^6$ cells/mL. The medium in the basolateral chamber was also replaced with fresh one. The microfluidic devices were then placed inside the CO2 incubator with prefusion flow is OFF for 24 hrs to allow cell attachment. Then, the perfusion was switched ON as described above at a flow rate of 10 nL/s.

Human epidermis in vitro model: Human epidermis in vitro model was constructed by culturing Immortalized human keratinocytes (KCs), HaCaT (Addexbio Biotechnologies, San Diego, USA) on a porous membrane. The cells were maintained in DMEM supplemented with 10% fetal bovine serum and antibiotics in culture flask according to the manufacturer's instructions. The KCs were harvested by treating with trypsin and re-suspended in the culture medium before seeding into the microfluidic device. Prior to seeding, the microfluidic device was washed with 70% ethanol, dried at a temperature of 70° C. in the oven for 30 min followed by UV irradiation for another 30 min. Then Culture medium was injected into the microfluidic device which was then incubated overnight. The medium within the microfluidic device was replaced with a fresh one and the cells were injected into the upper chamber (on top of the porous membrane) at a concentration of 105/mL using a syringe pump. The cell culture was maintained in a static condition to allow cell attachment onto the membrane. After 5 hours, the media flow was switched ON at a flow rate of 10-20 nL/s and the cell culture were maintained at 37° C. in a humidified incubator with 5% CO2. Air-liquid interface (ALI) on the apical side of the HaCaT layer was created after 20 days of culture. The culture medium was aspirated from the upper compartment and the cells were fed through basolateral compartment only.

Immune cell co-culture: The human leukemic monocyte lymphoma cell line (U937) (Addexbio Biotechnologies, San Diego, USA) was used as a model of human immune responsive dendritic cells (DCs). The immune cells were inoculated into the system after ensuring the differentiation of the pre-adipocytes to adipocytes which is indicated with clear appearance of lipid droplets within the cells. Also, the immune cells were introduced into the intestinal/epidermal models after ensuring a fully confluent layer of the epithelial/epidermal cells on top of the membrane.

Cell Viability: To assess cell viability, a mixture of calcein-AM (2 M) and ethidium homodimer-1 (4 M) was prepared and diluted in D-PBS. The mixture was then introduced into the cell compartment and allowed to incubate for a duration of 10 minutes. Then the cell viability was examined using a fluorescent microscope. Cell viability was calculated as the percentage of calcein AM-labeled cells. Images were captured from various locations within the cell compartment and the percentage values obtained from these images were then averaged. Data were represented as mean±SD.

Biochemical Characterization: Glucose uptake by the adipocytes: Glucose uptake by the differentiated adipocytes was measured using the glucose uptake assay kit, which uses 2-deoxy-2-[(7-nitro-2,1,3-benzoxadiazol-4-yl)amino]-D-glucose (2-NBDG) as a fluorescence-labelled deoxyglucose analog probe (Cayman Chemicals, Ann Arbor, MI, USA).

Cytokine immunoassay: The detection of inflammatory cytokines released from the co-cultured cells was performed using the enzyme-linked immunosorbent assay (ELISA). After treatment, the supernatant from the microfluidic device was collected for analysis at different time intervals. The expression of the inflammatory cytokines, TNF-α and Il-6, were investigated. ~100 μL of the supernatant was collected from each microfluidic device/experiment for subsequent ELISA testing. The cytokine concentrations in the medium were measured using the ELISA assay following the manufacturer's instructions or using fluorescent microscopy. Briefly, antibody-coated 96 well microplates were coated with primary antibody. The supernatant solution was then injected in the antibody-coated microplates and incubated. The plate was washed, and biotin-labelled detection antibody was added, followed by streptavidin-HRP. Finally, the absorbance was measured using a plate reader (Perkin Elmer, USA).

Bead-based immunoassay: The pro-inflammatory cytokine TNFα was captured on microfluidic device using functionalized magnetic beads. Magnetic beads, which pre-conjugated with a biotinylated cytokine capture antibody, were introduced into one of the fluidic chambers which is interfaced with other chambers through porous membrane. Immune cells were inoculated into their dedicated chamber at a concentration of ~5×10$^5$ cells/mL. After cell inoculation, the inlet and outlet of the cell chamber were blocked to prevent cell loss. The cells were supplied with the culture media through the upper chambers through membrane. Cells were treated with LPS through specific inlets and incubated for a certain period and the supernatant from the cell co-culture was allowed to infuse into the immune assay chamber which populated with the magnetic beads. Subsequently, the beads were extracted from the immune assay chamber and washed with PBS. Streptavidin-PE conjugated cytokine detection antibody was added to the bead suspension and incubated for 2 hours. Then, the magnetic bead suspension was washed with PBS and the fluorescent signal was measured using a fluorescent microscope.

Figure 19A:
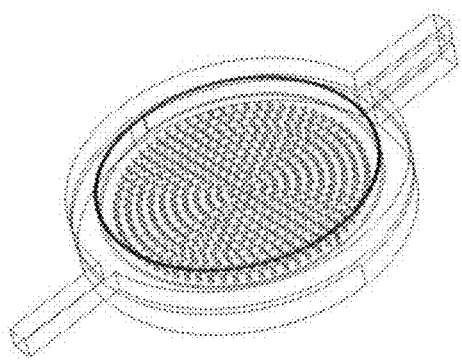
FIG. 19A, FIG. 19B, FIG. 19C and FIG. 19D shows Finite Element Analysis of the flow profile through planar porous membrane FIG. 20A, FIG. 20B
Figure 19B:
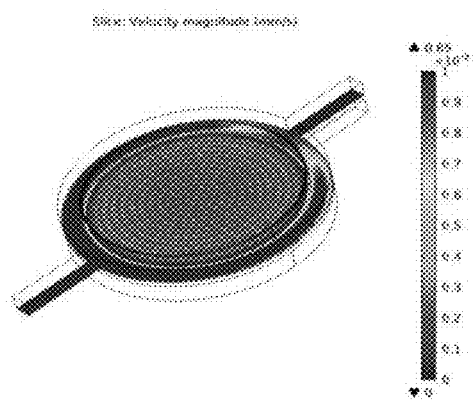
Figure 19C:
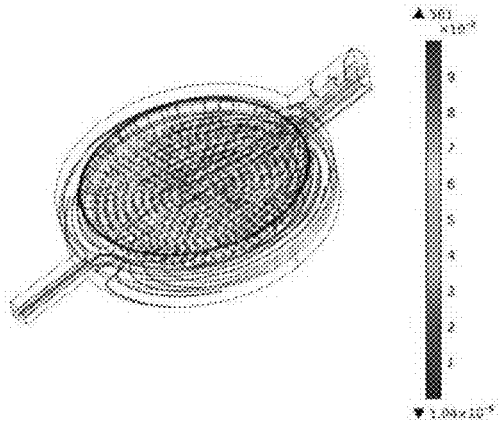
Figure 19D:
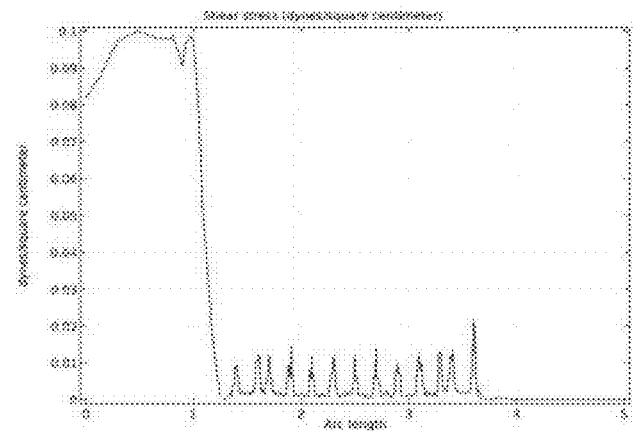

Simulation of the flow profile in the porous chambers: Finite element analysis (FEA) was carried out using the COMSOL Multiphysics software. Three-dimensional models with geometry that imitated the layout of two fluidic microfluidic devices were created: a) a simple circular fluidic chamber surrounded by SPW with a pore size of width, height, and depth of 2 μm, 5 μm and 50 μm; and b) squared multi-compartment microfluidic device with multi SPWs having the same pore size as above. The fluidic boundary conditions, materials and physics were applied. A laminar flow interface was used to compute the velocity of the fluid by solving the Navier-Stokes equations. Various conditions corresponding to the input/output ports were simulated to investigate the flow dynamics through the compartments by selectively applying the fluid flow through individual inlets. The velocity field and shear stress profiles were calculated at a fluid (water) flow rate of 8 nL/s. FIG. 18 shows the simulated velocity profile within compartmentalized microfluidic microfluidic device at different time intervals. The flow and mechanical shear stress were also simulated in a 3D model which comprises a circular chamber with a porous bottom and surrounded with a ring-shaped chamber both are separated with a SPW (FIG. 19a). The velocity field profile and streamlines (FIGS. 19 b and c) Show High Velocity Near Inlets/Outlets and within the Narrow compartments, while the flow velocity profiles tend to be uniformly low within the central compartments due to the high flow resistance imposed by the SPWs. The corresponding shear stresses on the cell membranes were calculated along a central line across the cell culture compartments (FIG. 19d). The resultant shear stresses in all cell culture compartments were found to be within the range of in vivo physiological interstitial shear stress (0.1 dynes per cm$^2$) [27]. It should be noted that shear stress can be adjusted by maneuvering the flow rates within the various compartments.

FIG. 18A shows Finite Element Analysis of the flow profile through the perfusion system with square-shaped and FIG. 18B shows circular-shaped fluidic chambers for the same analysis. FIG. 19a shows the 3D model which comprises a circular chamber with a porous bottom and surrounded with a ring-shaped chamber both are separated with a SPW. FIG. 19B shows the flow field. FIG. 19c flow streamlines profile. FIG. 19d shows the calculated shear stress in across the surface of the microfluidic device. The shear stress within the central chamber is within the physiological range in blood capillaries.

Results and Discussions

Figure 20A:
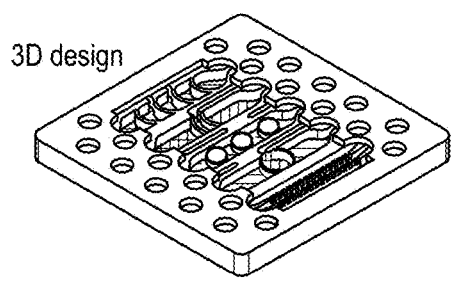
FIG. 20C shows SPW's in different configurations on a modular microfluidic device.
Figure 20B:
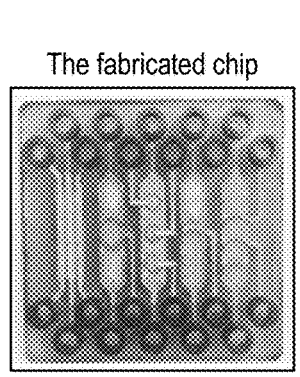
Figure 20C:
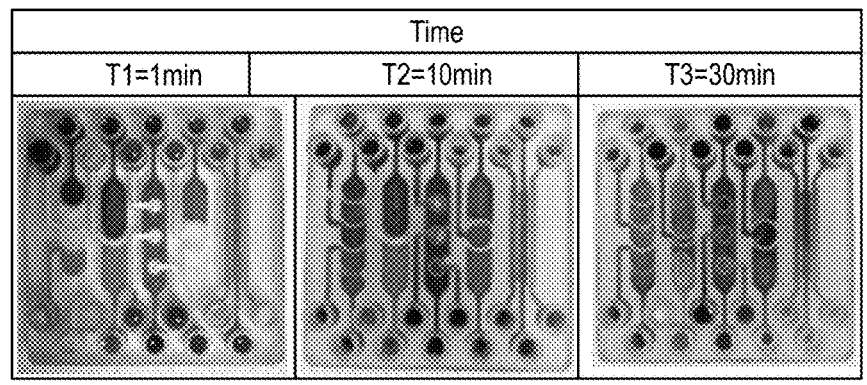
Figure 21A:
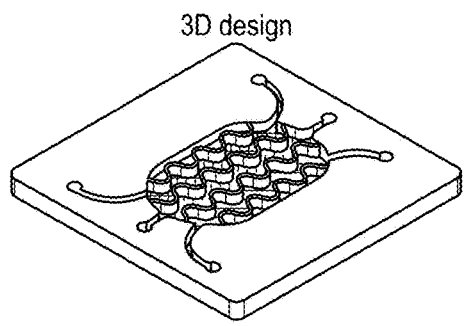
FIG. 21A, FIG. 21B and FIG. 21C shows modular microfluidic device with multiple planar compartments.
Figure 21B:
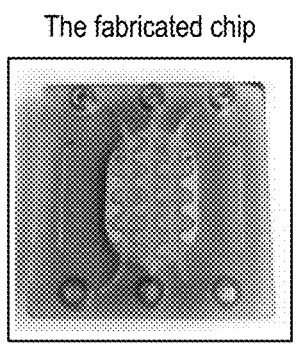
Figure 21C:
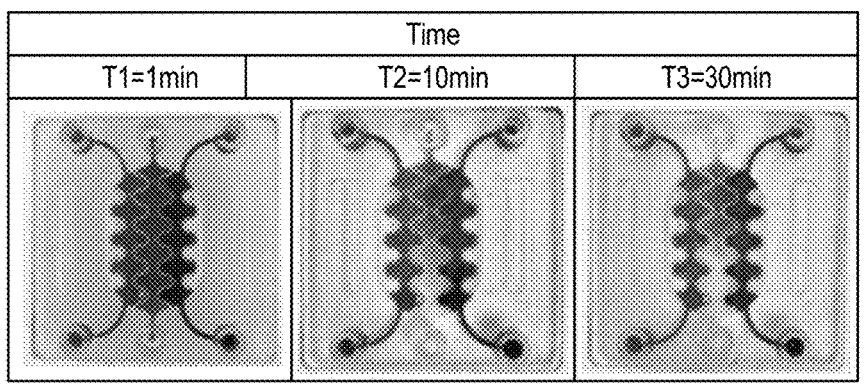
Figure 22A:
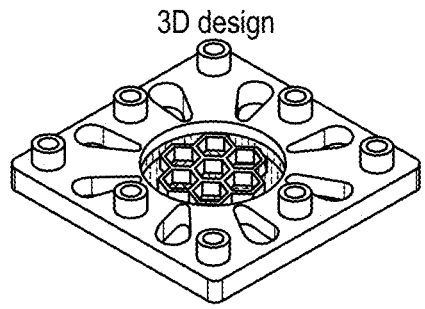
FIG. 22A, FIG. 22B and FIG. 22C shows modular microfluidic device having a honeycomb shaped interconnected compartments.
Figure 22B:
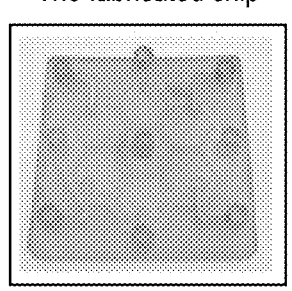
Figure 22C:
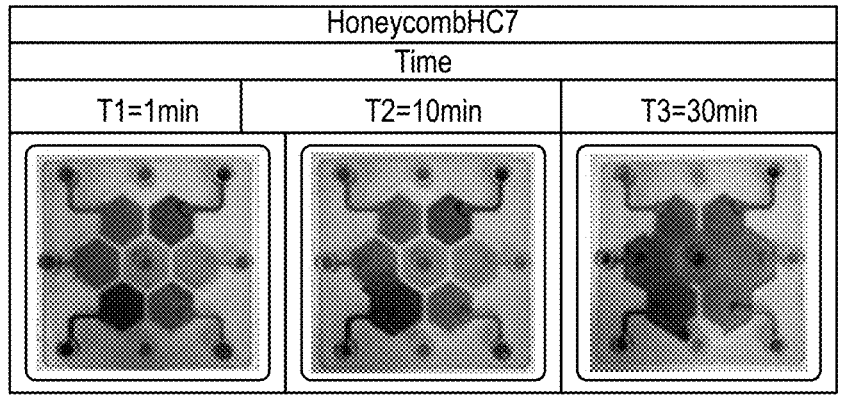
Figure 23A:
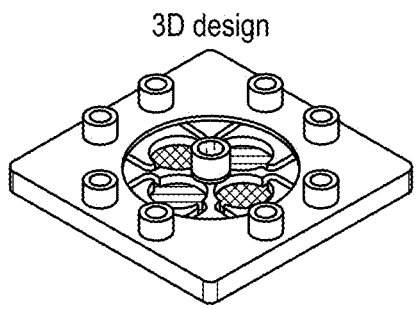
FIG. 23A, FIG. 23B and FIG. 23C shows a designed modular microfluidic device and a 3D fabricated device and color diffusion through the chambers.
Figure 23B:
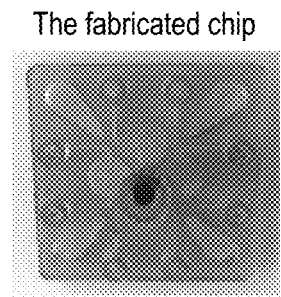
Figure 23C:
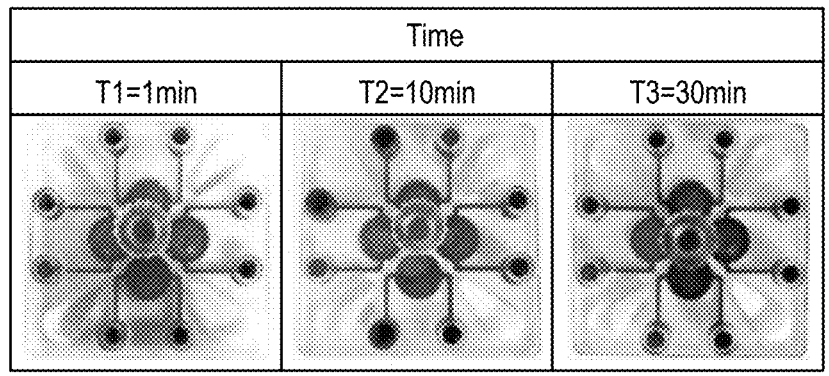
Figure 24A:
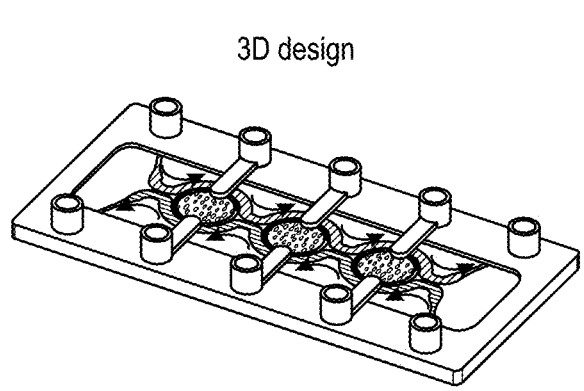
FIG. 24A, FIG. 24B and FIG. 24C shows a designed modular microfluidic device and a 3D fabricated device and color diffusion through the chambers.
Figure 24B:
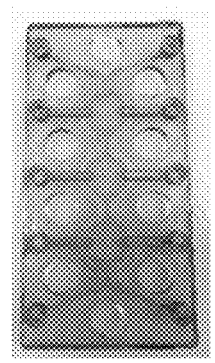
Figure 24C:
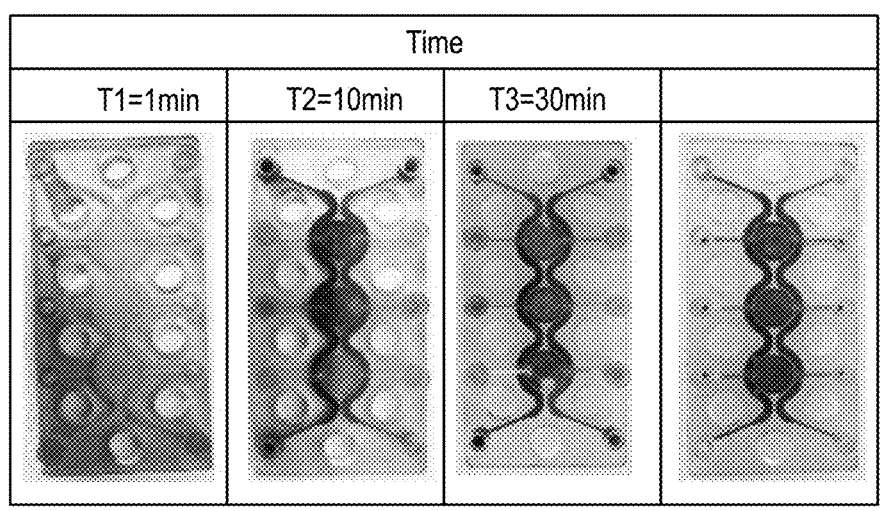
Figure 25A:
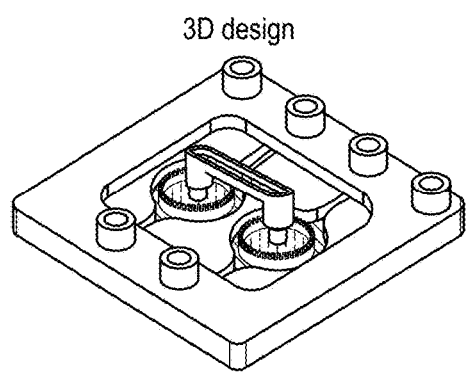
FIG. 25A, FIG. 25B, FIG. 25C and FIG. 25D shows a designed modular microfluidic device and a 3D fabricated device connecting the chambers with bridged channel.
Figure 25B:
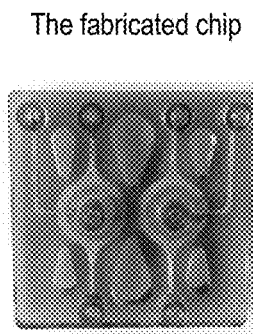
Figures 25C, 25D:
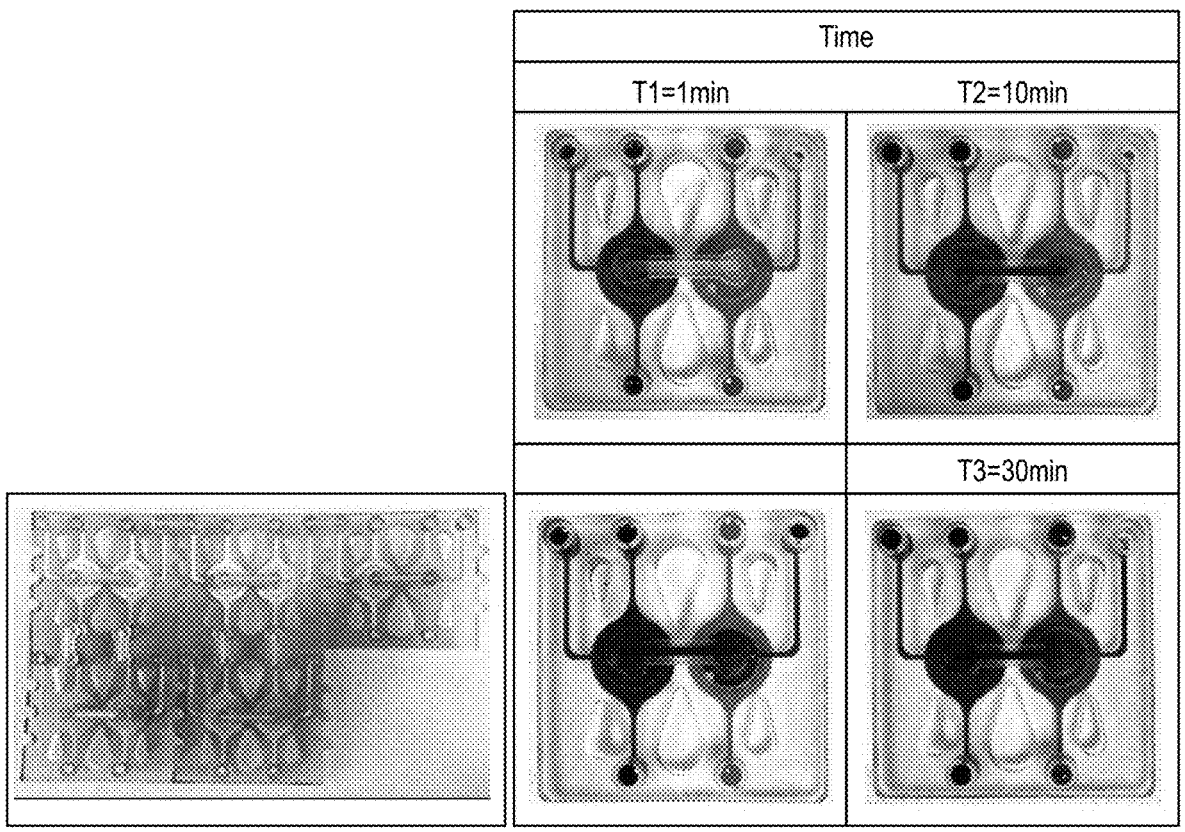
Figures 26A, 26B, 26C:
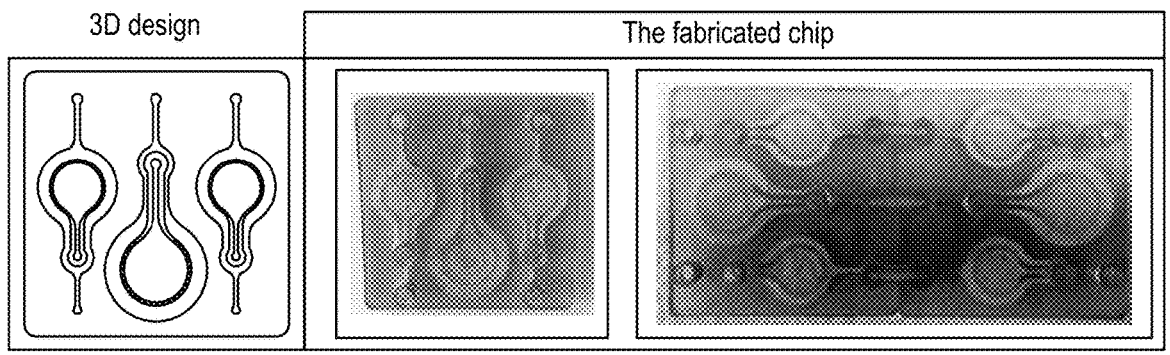
FIG. 26A, FIG. 26B, FIG. 26C and FIG. 26D shows a designed modular microfluidic device and a 3D fabricated device and color diffusion through SPW's.
Figure 26D:
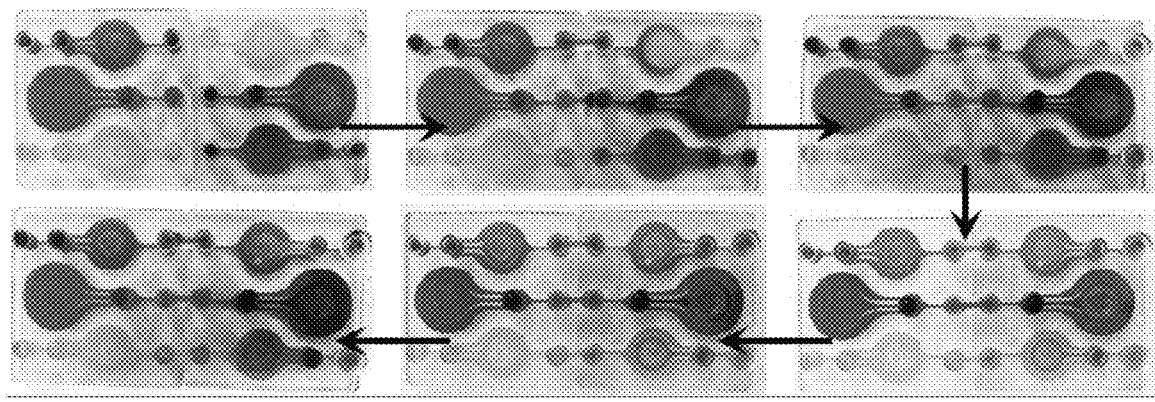
Figure 27A:
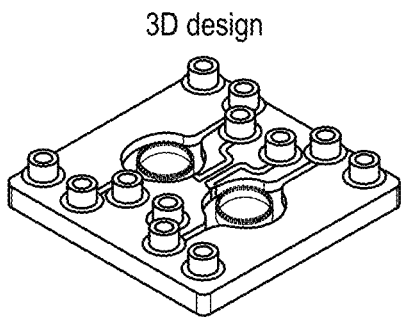
FIG. 27A, FIG. 27B and FIG. 27C shows another embodiment of a 3D fabricated device and color diffusion through SPW's.
Figure 27B:
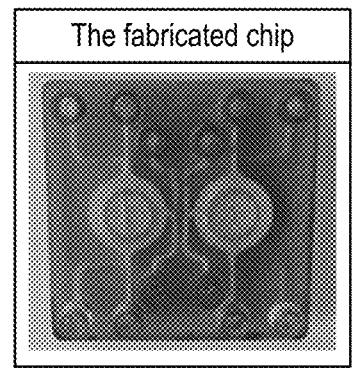
Figure 27C:
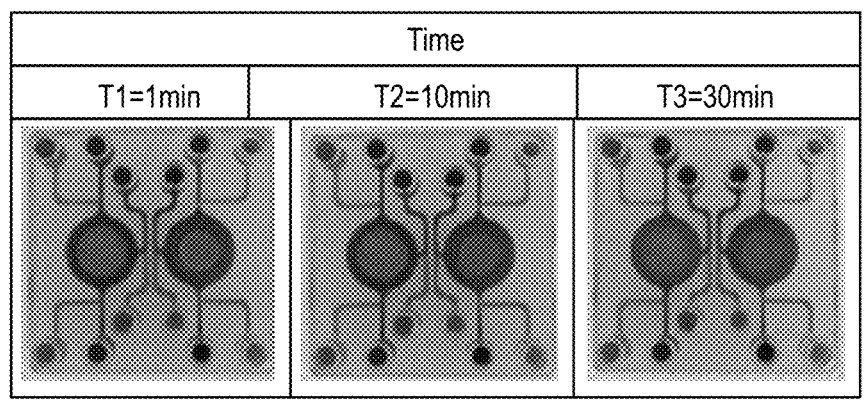
Figure 29A:
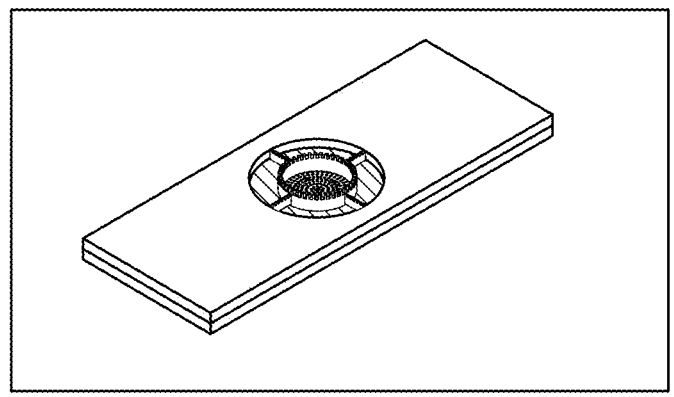
FIG. 29A, FIG. 29B and FIG. 29C shows florescence dye diffusion through a modular microfluidic device with SPW's.
Figure 29B:
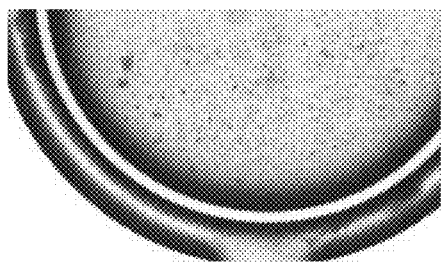
Figure 29C:
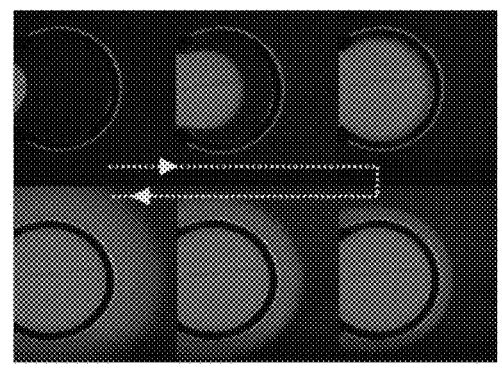

Fluid flow visualization: To visualize the fluid flow profile within the fabricated microfluidic devices, colored water (with food dyes) was injected into the individual microfluidic device and the diffusion of the color through the compartments was monitored. A series of images were taken at different time intervals which show the status of the fluidic exchange between the adjacent compartments. FIG. 20A, FIG. 20B and FIG. 20C shows a test structure of various designs of SPWs between multi-compartments. FIG. 20A shows the 3D structure design. FIG. 20B shows the fabricated microfluidic device. FIG. 20C shows a series of images showing the color diffusion of food color through the SPWs between different compartments. The time dependent flow of food color liquid at T1=1 min, T2=10 min and T3=30 min show the flow through geometrics and position of the porous walls. FIGS. 21A, B and C shows a compartmentalized microfluidic microfluidic device with 3 planar compartments separated by interlaced SPWs. FIG. 21A shows 3D view of the designed system. FIG. 21B shows the fabricated microfluidic device with channels and SPWs. The design is named Interplan 3 for the integrated planner porous barriers in this design. FIG. 21C shows a series of time dependent images (T1=1 min, T2=10 min and T3=30 min) showing the color diffusion through the SPWs between different compartments. FIGS. 22A, B and C show five interconnected compartments arranged in a honeycomb-shaped structure (HC7). Each compartment is separated by SPWs. FIG. 22A shows the 3D structure design. FIG. 22B shows the fabricated microfluidic device from the 3D design. FIG. 22C shows a series of images showing the colour diffusion through the SPWs between different compartments in a time dependent images (T1=1 min, T2=10 min and T3=30 min) manner. FIGS. 23A, B and C show four planner chambers with a central valve (4VC). The valve comprises a cylindrical rode with a hole. Rotating the valve either clockwise or counter clockwise links two opposite chambers while disconnect the other two chambers. FIG. 23A shows the 3D design of the microfluidic device. FIG. 23B shows the fabricated microfluidic device from 3D design. FIG. 23C shows a series of images showing the colour diffusion through the SPWs between different compartments in a time dependent images (T1=1 min, T2=10 min and T3=30 min) manner. FIG. 24 shows the VasChip3×2 system which comprises three circular chambers arranged in planar organization having SPWS. The three chambers are linked with two side channels: (a) The designed microfluidic device (b) The fabricated microfluidic device (c) A series of images showing the colour diffusion through the SPWs between different compartments in a time dependent images (T1=1 min, T2=10 min and T3=30 min) manner. FIGS. 25A, B, C and D show two chambers being connected through a bridging channel (FluBr2) and five microfluidic devices connected together with bridging channel. FIG. 25A shows a 3D designed microfluidic device. FIG. 25B shows the fabricated microfluidic device (single microfluidic device) using the 3D design. FIG. 25C shows five identical microfluidic devices connected with a bridging channel. FIG. 25D shows a series of images showing the colour diffusion through the SPWs between different compartments in a time dependent images (T1=1 min, T2=10 min and T3=30 min) manner. FIGS. 26A, B and C shows two microfluidic devices connected together through bridge channels and the configuration is called FluBrix. FIG. 26A shows the designed microfluidic device. FIG. 26B shows the fabricated microfluidic device (single microfluidic device). FIG. 26C shows two identical microfluidic devices connected with a bridging channel. FIG. 26D shows a series of images showing the colour diffusion through the SPWs between different compartments. FIGS. 27A, B and C show a VAS2xC configuration which represents vascularized complex microfluidic device connected through a bottom chamber. FIG. 27A shows the 3D designed microfluidic device. FIG. 27B shows the fabricated microfluidic device. FIG. 27C shows a series of images showing the colour diffusion through the SPWs between different compartments in a time dependent images (T1=1 min, T2=10 min and T3=30 min) manner. FIGS. 28A, B and C show a multi cell chamber with a bottom chamber attached to it (Vas4xC). FIG. 28A shows the 3D designed microfluidic device. FIG. 28 B shows the fabricated microfluidic device with multiple wells and a bottom chamber attached. FIG. 28C shows a series of images showing the colour diffusion through the SPWs between different compartments in a time dependent images (T1=1 min, T1=10 min, T1=20, T1=30 min) manner. FIG. 29A shows the designed Simicrofluidic device (COMPOS). FIG. 29B shows a microscopic image of the fabricated microfluidic device. FIG. 29C shows series of images showing the diffusion of fluorescent dye through the SPWs between the central and outer compartments.

Inter-compartment permeability: The crosstalk between various adjacent compartments in selected fabricated devices was investigated by injecting FITC-dextran 4k Da tracer into one compartment (upstream) at a concentration of 5 µg/mL and the fluorescence intensity was recorded at different time intervals across the downstream compartment.

Figure 30A:
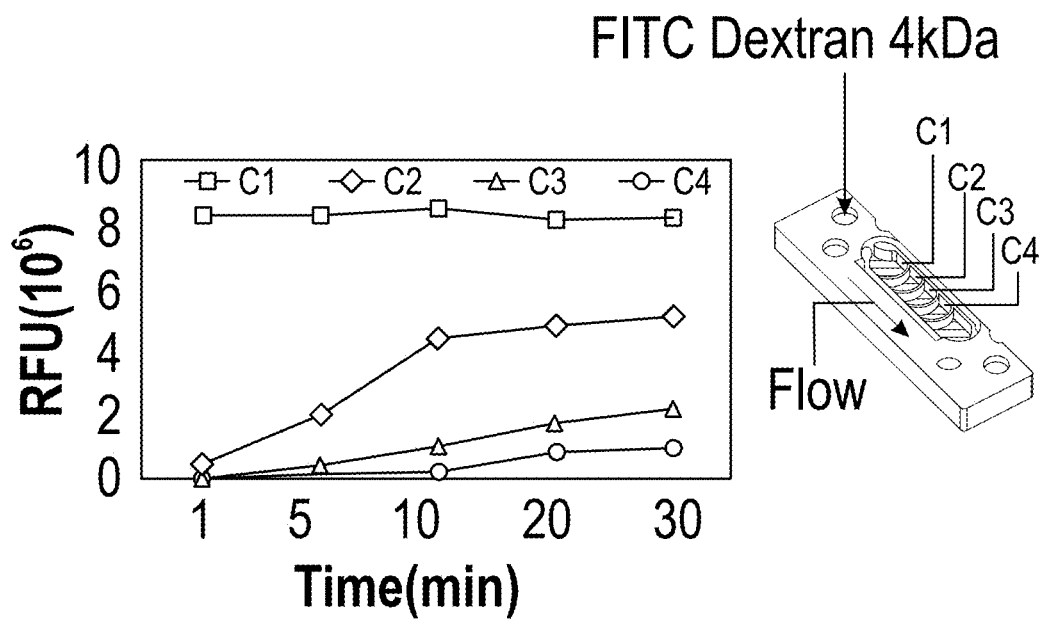
FIG. 30A, FIG. 30B, FIG. 30C, FIG. 30D, FIG. 30E and FIG. 30F relative fluorescence intensity measure in various downstream compartments.
Figure 30B:
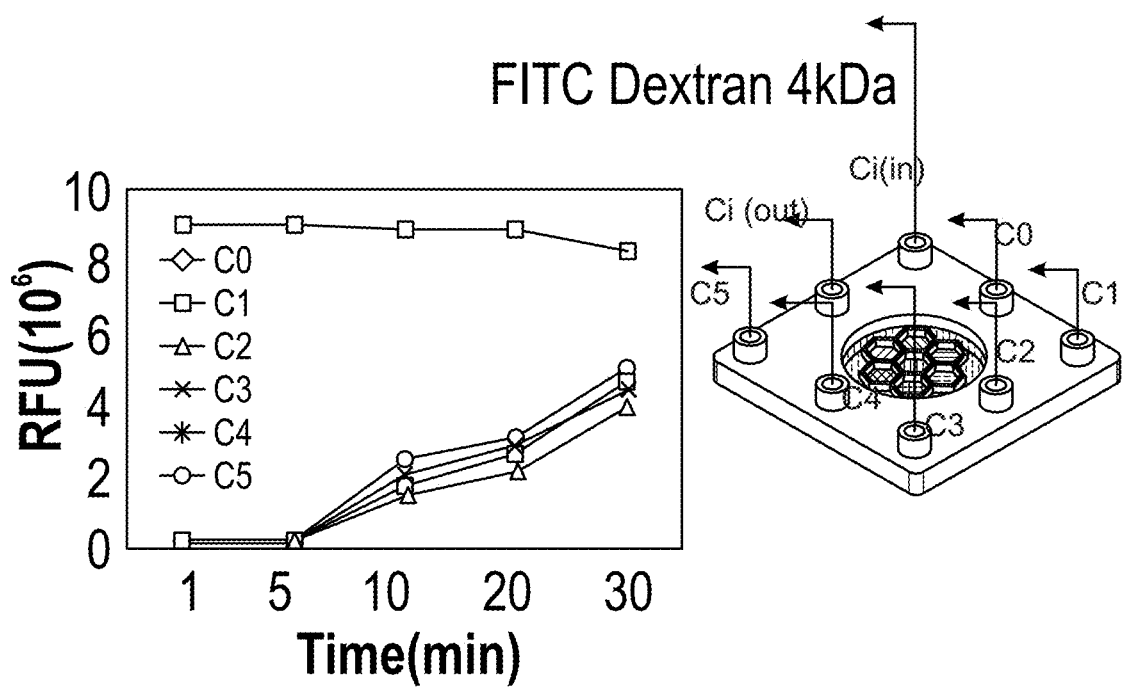
Figure 30C:
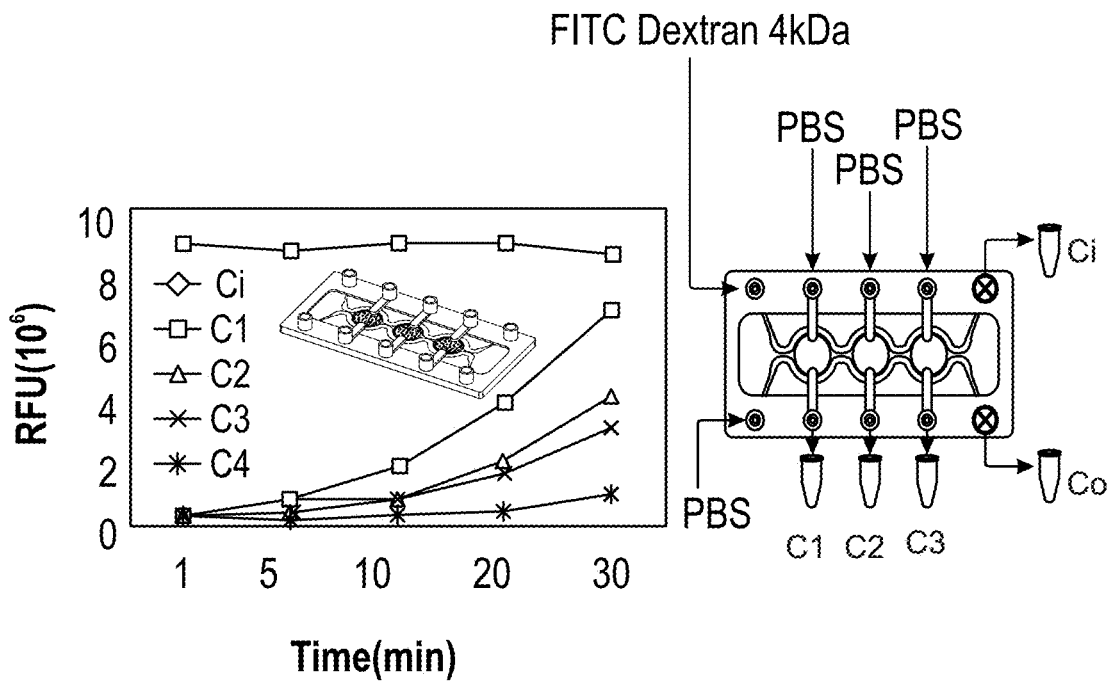
Figure 30D:
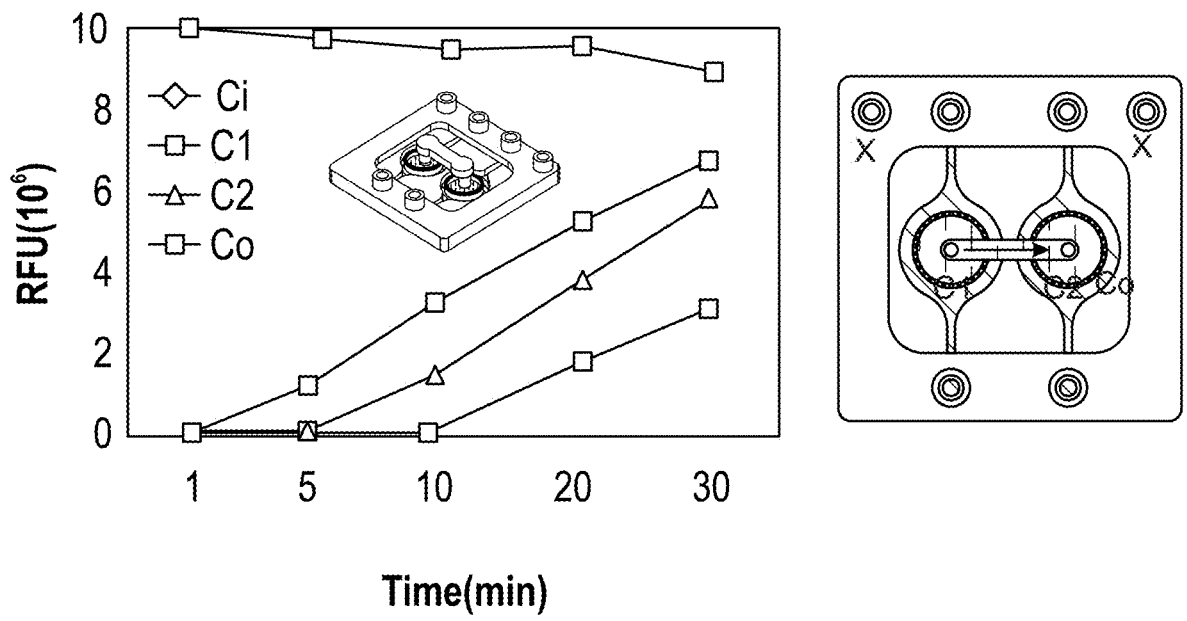
Figure 30E:
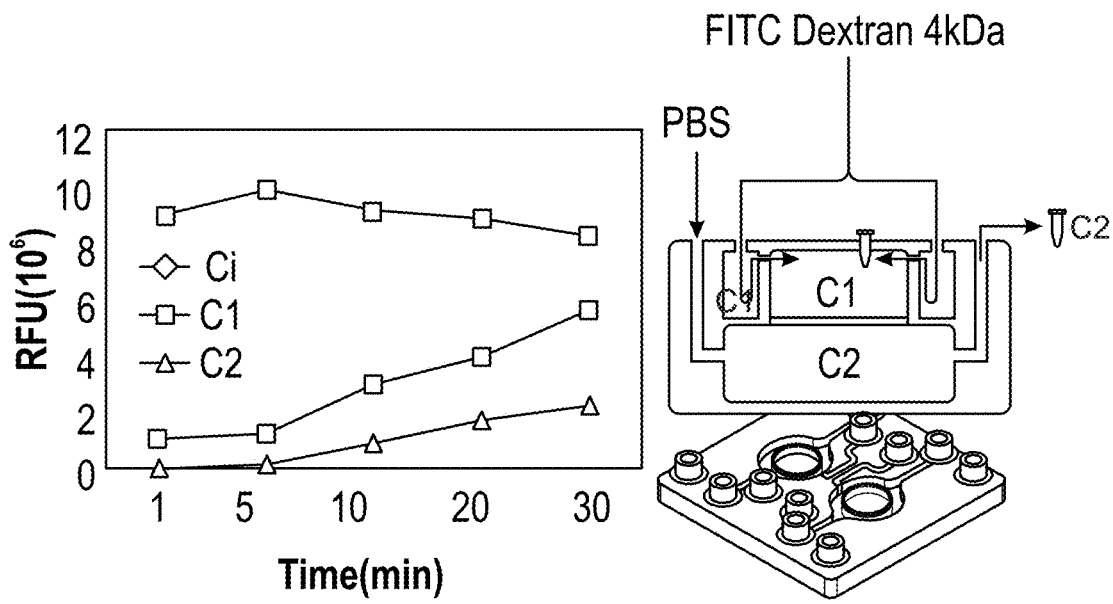
Figure 30F:
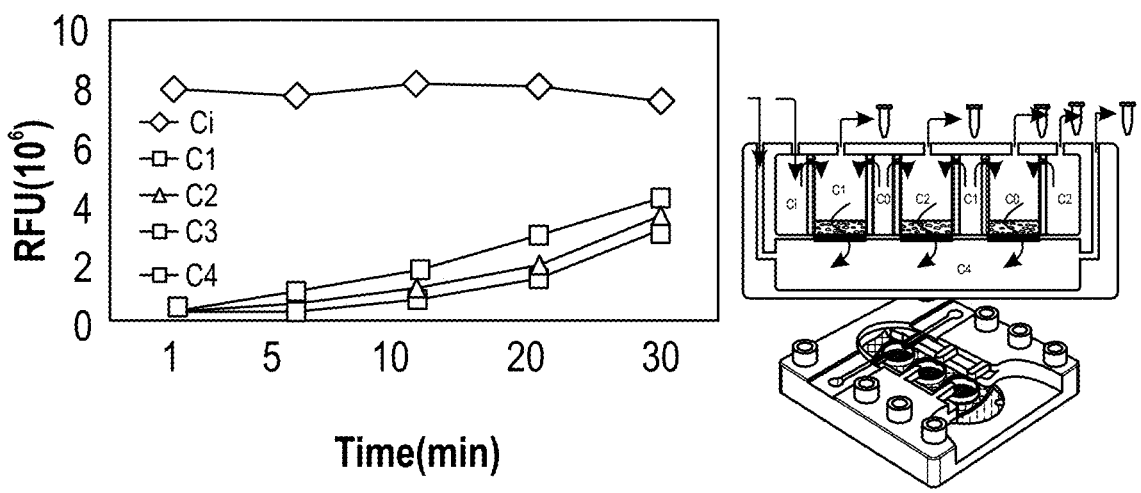

FIGS. 30A, B, C, D, E, and F shows the permeability profile between various adjacent compartments as indicated by the fluorescence intensities (FIs). The inset on the right shows the route of interest of FITC transport. The FI was measured when the compartments were filled with a clear PBS solution (no FITC-dextran) and subtracted from the total apparent FI to obtain the actual FI due to the dextran permeability. The results in FIG. 30A, FIG. 30B, FIG. 30C, FIG. 30D, FIG. 30E, and FIG. 30F shows the relative fluorescence intensity measured in the various downstream compartments after injection of 4KDa FITC-dextran at a concentration of 5 µg/ml in the inlet compartment (Ci). The FI which is used as an indicator of the permeability increases with time. FIG. 30A shows TS FITC-dextran was injected in C1, and the fluorescence intensities were measured in all compartments at different time intervals. The flow direction is from C1 to C4. FIG. 30B shows HC7 C0, C1, C2, C3, C4, C5, C6 label the honeycomb compartments with C0 is the central compartment and C1-C6 are the outer compartments). FITC-dextran was injected into the compartment Ci and the fluorescence intensity within every compartment was measured at different time intervals. The ligands in the diagram (left) indicate the fluorescence intensities. FIG. 30C shows Vascular3x2 FITC-dextran was injected through Ci, PBS was injected in the compartments C1, C2, C3 independently and the fluorescence intensities were measured in C1, C2. C3, Ci and Co at different time intervals. The flow direction is from left to right. FIG. 30D shows FluBr2 FITC-dextran was injected through Ci, PBS was injected in the compartments C1 and C2 independently and the fluorescence intensities were measured in C1, C2, Ci and Co at different time intervals. The bridging channel enables the fluid to travel from C1 to C2. FIG. 30E shows Vascular2xC FITC-dextran was injected through Ci, and the fluorescence intensities were measured in Ci, C1 and C2 at different time intervals. The SPW enables the liquid to diffuse from Ci to C1 and the porous membrane enables the liquid to diffuse from C1 to C2. FIG. 30F shows Vacular4xC FITC-dextran was injected through Ci, and the fluorescence intensities were measured in Ci, C1, C2, C3 and C4 at different time intervals.

Cell (co)-culture characterization: Cell culture/co-culture was implemented in selected devices and the crosstalk between the grown cells was examined for modelling specific (patho)-physiological conditions:

Insulin resistance in the inflamed adipose tissue: Infiltration of immune cells into adipose tissue is associated with chronic low-grade inflammation in obese individuals. In obese individuals, the adipose tissue becomes heavily infiltrated by inflammatory immune cells such as monocytes, macrophages, and Th1 cells. These immune cells interact with adipocytes, triggering chronic inflammation that ultimately leads to the impairment of insulin action on adipocytes and the development of insulin resistance. Among the immune cells present in adipose tissue, macrophages are the most abundant. In lean adipose tissue, macrophages make up approximately 5% of the total cell population. However, in obese adipose tissue, this ratio can increase significantly, reaching up to 50%. It is widely accepted that the expansion of adipose tissue, which occurs in obesity, disrupts the secretion of adipokines, such as upregulated MCP-1 and downregulated adiponectin production. Consequently, this dysregulation induces the infiltration of peripheral monocytes into the adipose tissue. To demonstrate the practical application of our fabricated devices, we utilized VasChip3x2 to create an organotypic co-culture system of adipocytes and monocytes/macrophages. This co-culture system has been previously used to construct an in vitro model of inflamed human adipose tissue. It has proven valuable in studying the interplay between immune cells and adipocytes in the context of human obesity and insulin resistance. The interaction between human adipocytes, immune cells, and tissue-resident macrophages serves as an exemplary model for understanding how the interplay between different cell types contributes to the pathogenesis of various diseases, including type 2 diabetes. For the immune-metabolic analysis, the adipocytes and immune cells were cultured in their designated compartments within the microfluidic device. This co-culture was maintained for two weeks before conducting the immune-metabolic analysis. Adipocytes and U937 cells were cultured on the microfluidic device as previously described, and an inflammatory state was induced by treating the cells with 100 ng/ml of lysophosphatidic acid (LPA). The glucose uptake by the adipocytes and the secretion of TNF and IL-6 in the supernatants were quantified from the same set of adipocytes. The cell viability over the course of 14 days was within an acceptable range, being above 80%. The immune-metabolic status of the co-culture was assessed as shown in FIGS. 31d and 31e. A correlation was observed between the cytokine profile and glucose uptake. In the adipocyte monoculture, a significant glucose uptake was observed, particularly after insulin treatment, with a negligible regulation of cytokines. However, in the co-culture set, a slight decrease in glucose uptake was observed, accompanied by a notable increase in cytokine secretion.

Figure 31A:
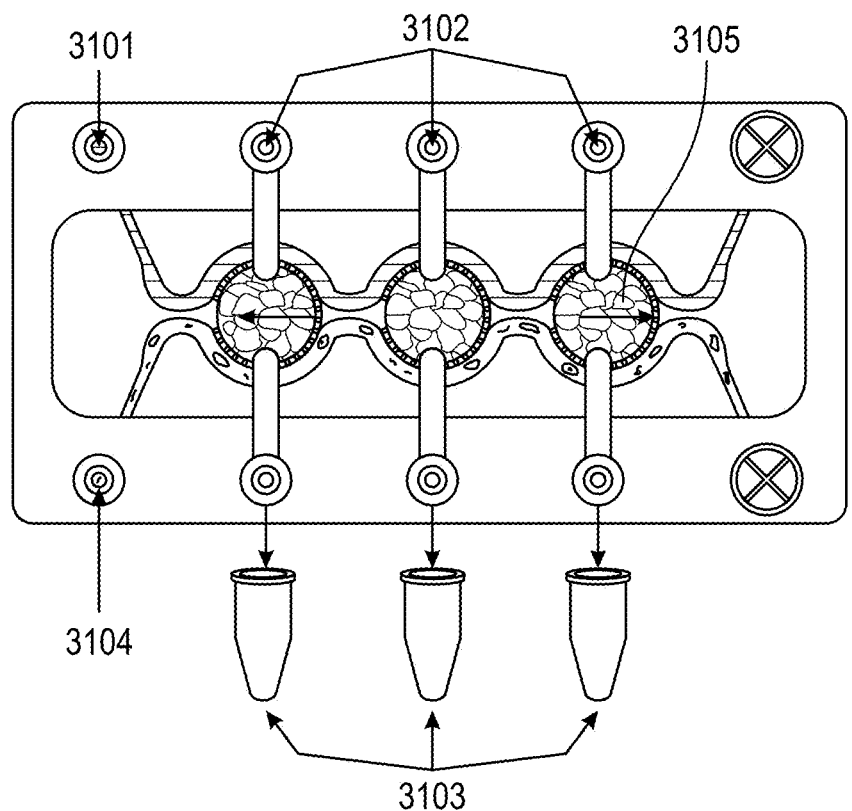
FIG. 31A, FIG. 31B, FIG. 31C FIG. 31D and FIG. 31E shows an example of adipocyte immune cell co-culture in a modular microfluidic device.
Figure 31B:
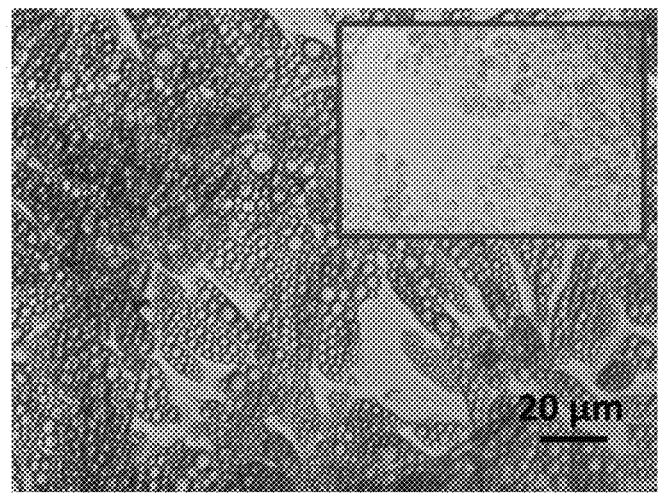
Figure 31C:
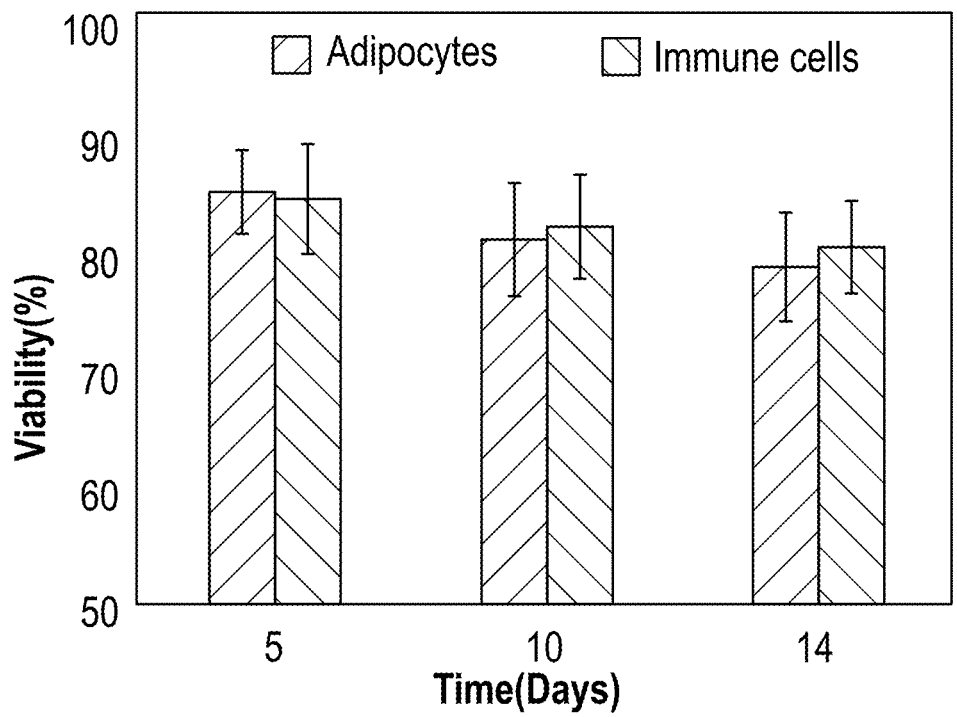
Figure 31D:
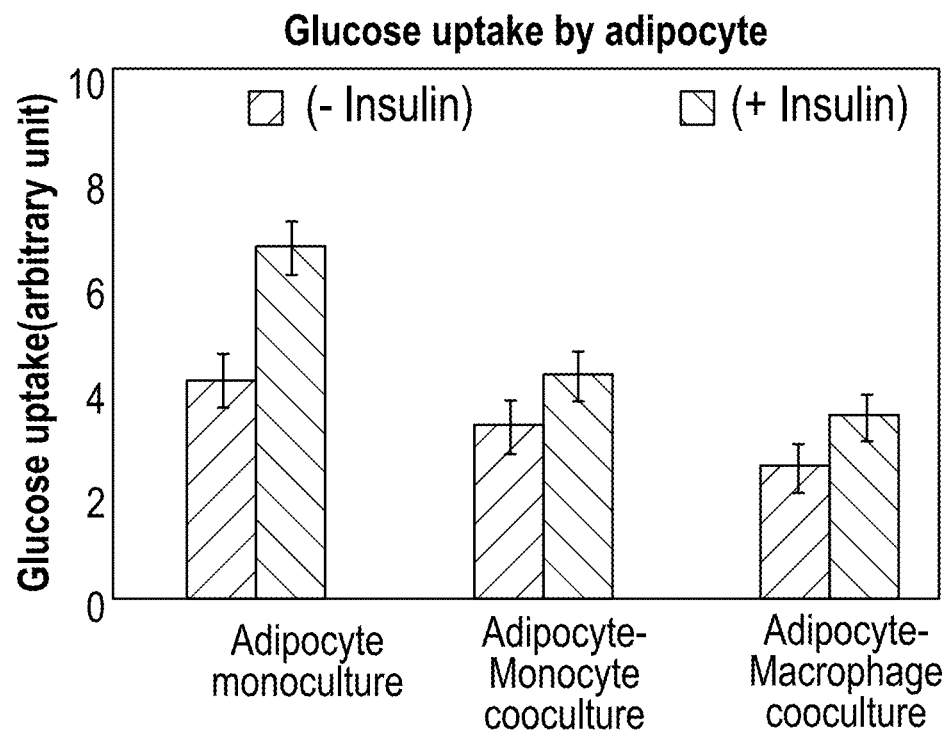
Figure 31E:
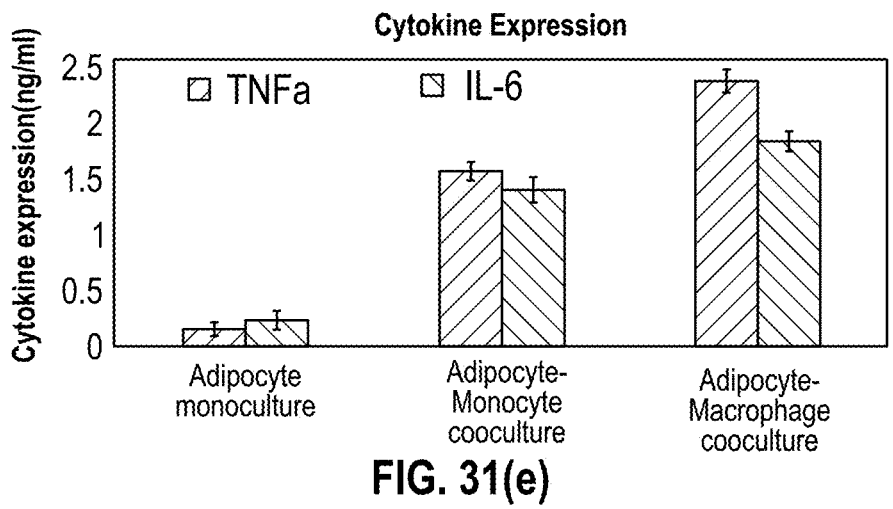

FIG. 31a shows schematic drawing of the adipocyte-immune cell coculture 3105 for modelling the immune cell (macrophage) infiltration in the insulin resistance. The cell culture supernatants from the cell growth chambers 3105 were collected in the tubes 3103. The input of nutrients were provided by 3101, 3102, and collected by outlets 3104. FIG. 31b shows fully differentiated and hypertrophied adipocytes after 14 days of culture. U937-based macrophages are shown in the inset. FIG. 31c shows Cell viability of the cocultured cells. FIG. 31d shows Glucose uptake by the adipocytes at three different cell culture setups. FIG. 31e shows Cytokine expression at three different cell culture setups. This system mimics the relevant microenvironment found in the human body. Human pre-adipocytes were cultivated within the central compartments, while human monocytes were grown in the surrounding meandering channels [FIG. 31a]. The unique architecture of the cell-cell interfacing structure ensures an organotypic culture, with porous barriers separating the different cell types into dedicated compartments.

Furthermore, when the inflammation state was induced by treatment with LPA, resulting in differentiation into macrophages, a significant increase in cytokine secretion and a decrease in glucose uptake were observed. The key feature of our microfluidic system is its ability to host a co-culture of two or more cell types in close proximity. Although physically separated, the cells continuously exchange bio/chemical signals, creating an environment similar to in vivo conditions.

Figure 32A:
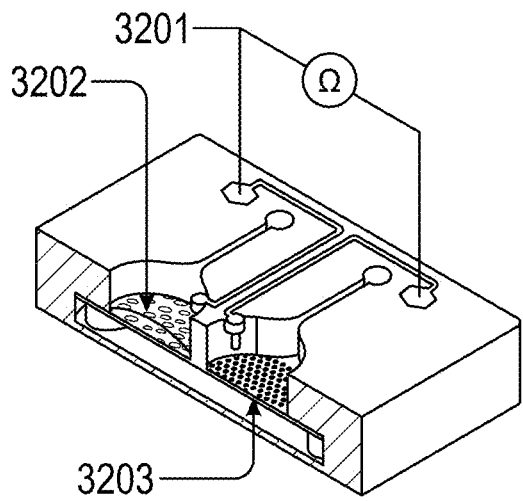
FIG. 32A, FIG. 32B, FIG. 32C and FIG. 32D shows cross sectional view of TEER microfluidic device in another embodiment of cell culture in modular microfluidic device.
Figure 32B:
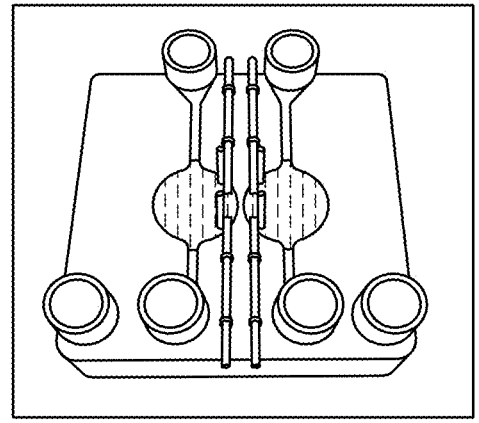
Figure 32C:
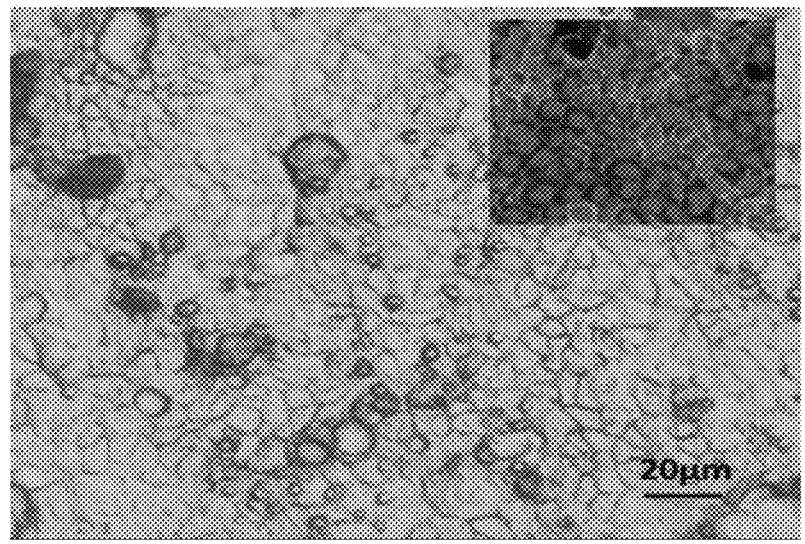
Figure 32D:
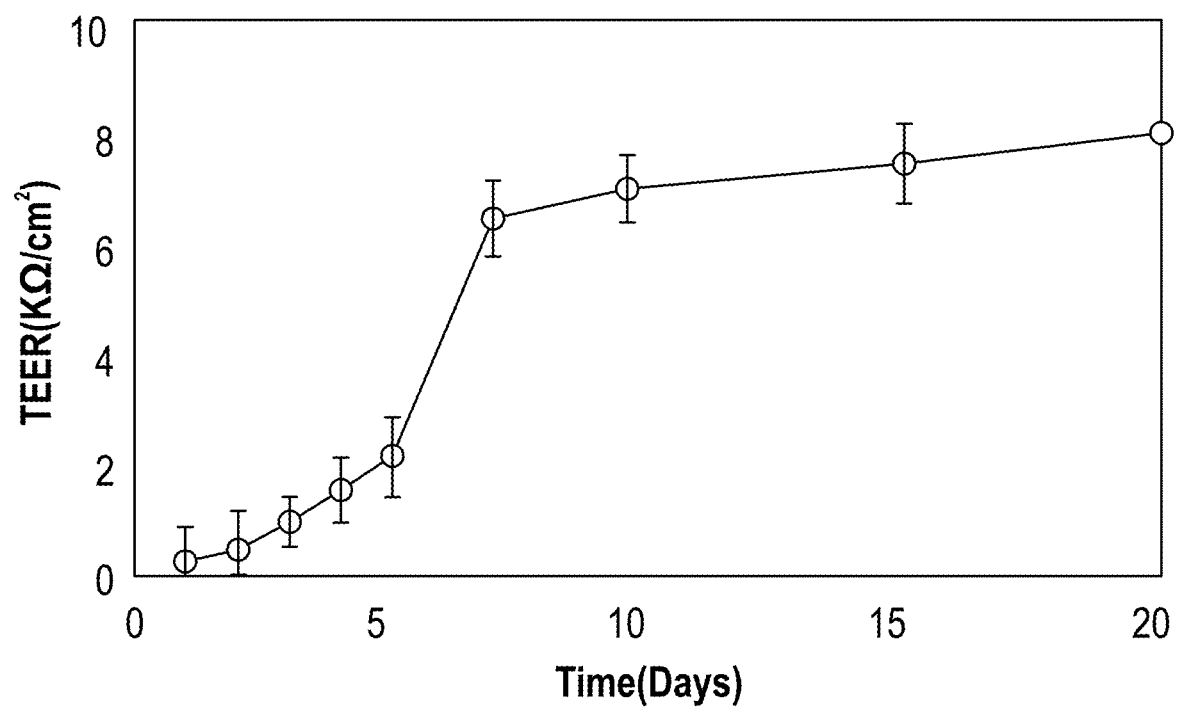

Measurement of TEER using the TeerMicrofluidic device: Here, we employ the TeerMicrofluidic device system to construct an in vitro model of the human intestinal that is interfaced with a co-culture of immune cells to demonstrate the activation of the immune cells through the intestinal barrier which emulate some pathophysiological conditions such as infection. FIG. 32a shows Cross-sectional view of the TeerMicrofluidic device illustrating the arrangement of the cell culture. FIG. 32b shows an optical image of the device. FIG. 32c shows Caco-2 cell monolayer grown on the membrane in the upper compartment after 14 days of seeding. A fully confluent monolayer was formed after 4 days of cell culture. FIG. 32d shows the measured TEER of the epithelial monolayer. The intestinal barrier is modeled by a monolayer of Human intestinal cell line (Caco-2 cells) cultured on a porous membrane. The Caco-2 cells were seeded on the porous membrane in the first upper compartment at a concentration of ~5 x$10^5$ cell/mL and the U937 cells were seeded in the lower compartment. The second upper compartment, which is fluidically connected to the lower compartment, is utilized for TEER measurements as explained in section 3.3. The fluid perfusion through the apical and basolateral compartments was driven by two independent syringe pumps so that the flow conditions can be selectively modulated for a different condition or switched ON/OFF. The cell growth in the microdevice was monitored visually to ensure the formation of a fully confluent monolayer and TEER was measured every 12 hours. A fully confluent monolayer of caco-2 cells was observed after 4-5 days after cell seeding (FIG. 32c). Cells appeared to cover the entire membrane surface from the fourth day and beyond and maintained cell viability of >90% for 14 days which demonstrates the importance of the dynamic cell culture condition over static culture in modeling the interaction between various cell/tissue types. FIG. 32d shows the measured TEER values over a 20-day duration. The TEER values exhibit a consistent increase over time, with a notable sharp increase observed starting from day 5. This significant increase suggests the initiation of tight junctions (TJs) formation, which is indicative of the establishment of a functional intestinal epithelium. The sustained high TEER values observed for three weeks indicate the viability of the cells and the presence of a healthy intestinal epithelium. This robust cellular environment makes it suitable for conducting permeability studies over extended periods.

Figure 33A:
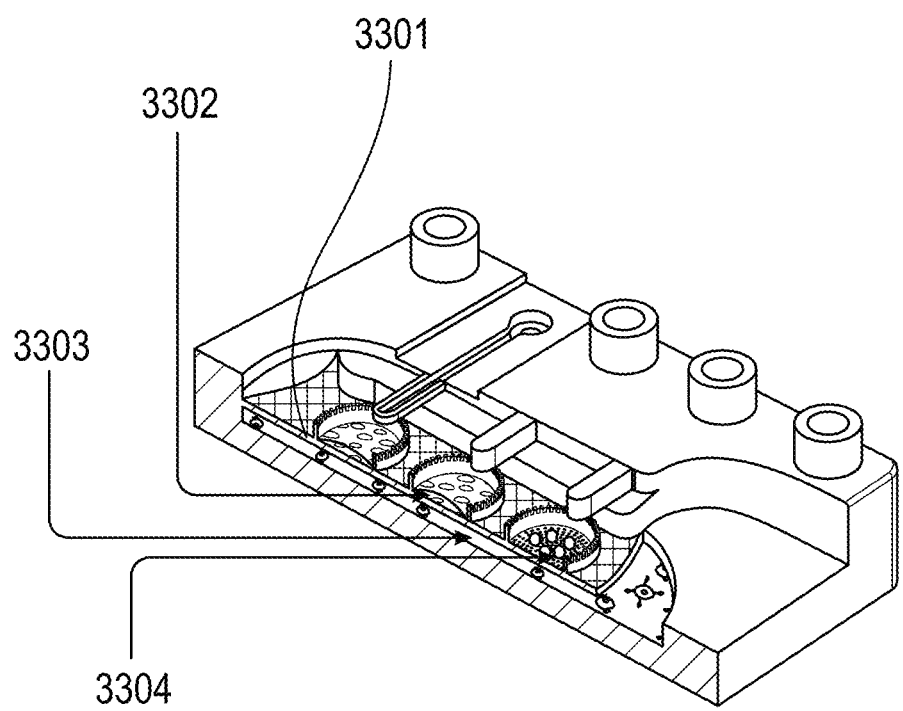
Figure 33E:
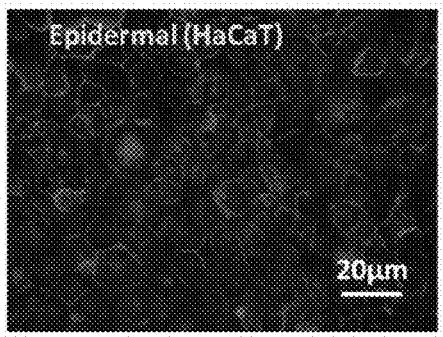

Intestinal-epidermal-immune cell tri-culture: Here, we used the Vascular4xC microfluidic device to activate immune cells using the leukemic monocyte lymphoma cell line (U937) as the immune responsive cells, through an epithelial intestinal layer and a skin epidermal layer (FIGS. 33a and b). This device comprises three upper chambers (3301, 3302 and 3303) with a porous membrane bottom (3304) and surrounded with a common feeding chamber. Underneath these chambers, there is a large lower chamber that overlaps with all the upper chambers and exchanges the fluid/molecules through the porous membranes. Intestinal epithelial cells (caco2 cell line) were grown in the first upper chamber and epidermal cells (HaCaT cell line) were grown in the second upper chamber while the third chamber was dedicated to cytokine capturing using magnetic-bead immune assay. The lower chamber was populated with immune responsive cells (U937 cell line) (FIG. 33b). The flow of the experiment is illustrated in FIG. 33c. The microfluidic device is fabricated and prepared 3313. Initially, the intestinal and epidermal layers were grown in two adjacent upper compartments 3314 and 3315. The cells were monitored until fully confluent and differentiated cell layers were established. FIGS. 33 d and e show optical images of the fully differentiated intestinal and epidermal cell layers after two weeks of culture. After the successful establishment of the epithelial and epidermal layers, immune cells were introduced (3316) into the lower common chamber as depicted in FIGS. 33a and 33b. Given that monocytes are suspended cells, precautions were taken to prevent cell leakage from the microfluidic device. To ensure cell retention, the inlet and outlet of the chambers were securely closed after the inoculation of immune cells, effectively preventing any undesired cell flow out of the microfluidic device. This precautionary measure aimed to maintain the desired cell distribution and facilitate the subsequent stages of the experiment.

Figure 33F:
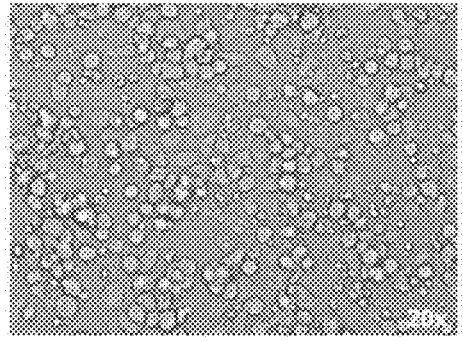
Figure 33G:
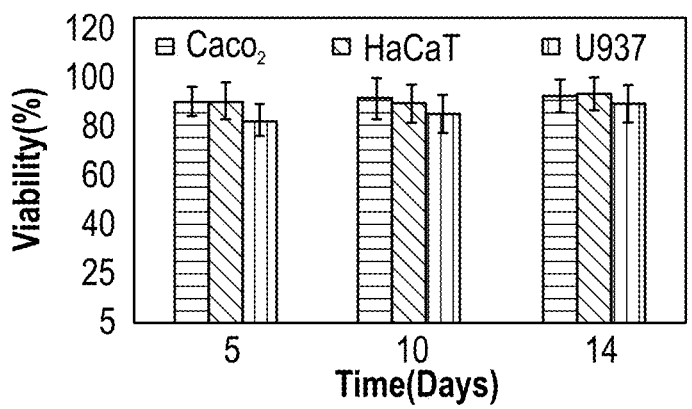
Figure 33H:
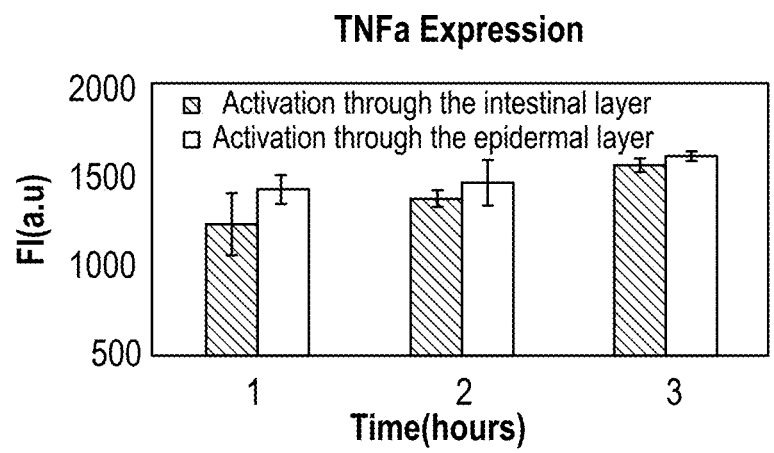

On the following day, conjugated immune cells were injected into the third upper chamber of the microfluidic device. To induce an inflammatory state in the immune cells, the intestinal or epidermal layer was treated with lipid polysaccharide (LPS) at a concentration of 1 µg/mL, 24 hours after the immune cells were inoculated. Specifically, the intestinal cell (caco-2) monolayer was first treated with LPS (3318) and incubated. Subsequently, the magnetic beads (3317) were extracted and replaced with a fresh bead suspension. This process was repeated three times at intervals of 1, 3, and 6 hours. Subsequently, the microfluidic device was maintained under perfusion for an additional three days without any further treatment. On the following day, the epidermal cells were subjected to LPS treatment, similar to the previous procedure with the intestinal cells. The cytokine was captured using the magnetic bead-based immune assay, following the same methodology employed for the intestinal cells (3319). FIG. 33c shows an image of the epidermal cells layer. FIG. 33f shows an image of the immune cells. FIG. 33g shows cell viability in the tri-culture. FIG. 33h shows the TNFα expression (expressed with the fluorescent intensity) due to the activation of the immune cell through the intestinal and epidermal layers.

Planar compartmentalized microfluidic devices were created having several fluidic compartments with different organizations/orders that are separated by semi-porous sidewalls with modular porosity. The pores in the side walls create microchannels, or perfusion channels, with a length equal to the thickness of the sidewalls. The perfusion channels that connect the fluidic compartments within the same plane can be created on either the upper or lower side of the sidewalls. While the side walls physically separate the cell of different types in distinct compartments, the high-density perfusion channels surrounding these compartments provides steady flow of cell culture media/stimuli and enables cell-cell crosstalk between the heterogenous cell populations in the adjacent compartments. By arranging multiple fluidic chambers in close proximity to each other, different types of cells can be cultured in a dynamic environment which enables mimicking the structure and function of a specific human organ or multi-organs. The porous compartmentalized fluidic structure allows for the hosting of multi-cellular structures that are physically separated yet fluidically connected, enabling chemical interactions between different cell types. The fluidic compartments can be organized in different orders, such as a simple organization with two compartments separated by a thin, porous wall, a concentric organization with two or more compartments arranged in a concentric format to model an individual organ, or a complex organization with compartments arranged in parallel or in series to model the structure of multiple organs. The architecture of the multi-compartment is determined by the desired biological model (structure) and the physiological parameters need to be investigated.

3D compartmentalized modular microfluidic devices were designed, fabricated, and characterized. These modular microfluidic devices are characterized by multi-compartment structure with a combination of planar (horizontal) and vertical organization and interfaced with planar and vertical porous barriers (i.e., semi-porous sidewalls and planar porous membranes). The semi-porous sidewalls and membranes create a 3D porous fluidic structure that allows for improved perfusion and cell-cell/tissue-tissue interaction. The 3D fluidic structure can be designed in various ways, such as a simple two vertically stacked compartment with a porous membrane and porous sidewalls, or with several compartments in the upper and lower layers. The membrane between the upper and lower layers can be customized to be porous in specific locations and non-porous in others, facilitating direct and indirect cell-cell interactions between different cell types. The combination of semi-porous walls and planar membrane enables connecting multi-compartments in complex multi-directions.

The porous structure of the membrane and sidewalls can serve as a scaffold to construct biological barriers found in the human body, such as intestinal epithelium, blood vessel endothelium, and skin epidermis. Additionally, microelectrodes can be integrated within the porous structure and used to monitor ion transport through these biological barriers, specifically measuring the TEER. By applying a voltage through one pair of electrodes, the current passing through the other pair can indicate the integrity and transport properties of the epithelial layer. In general, to measure TEER across the epithelial layer, the electrodes must be arranged such that one electrode faces the apical side of the layer and the other faces the basolateral side. In the device "TeerMicrofluidic device", the electrodes can be arranged in the upper compartments by connecting the lower (basolateral) compartment of the epithelium model to an auxiliary compartment located in close proximity. In this setup, ions and other biochemical substances can transport from the basolateral compartment of the epithelium model to the apical compartment of the auxiliary chamber in the upper layer. Therefore, TEER electrodes can be fabricated on only one substrate, simplifying the fabrication and measurement process.

This study presents the design of versatile and modular microfluidic systems for organotypic cell co-culture, each with its own unique features and applications. The modular microfluidic device comprise of compartmentalized structures with semi-porous sidewalls and membranes, creating fluidic compartments and perfusion channels. These structures allow for the steady flow of cell culture media and facilitate cell-cell crosstalk between different cell populations. By arranging multiple fluidic chambers in close proximity, the system enables the culture of different cell types in a dynamic environment that mimics the structure and function of human organs. These systems have the potential to advance our understanding of organ physiology and contribute to the development of new therapeutic approaches.

What is claimed is:

1. A method of making a modular microfluidic device, comprising:
    layering a top and a bottom layer of the modular microfluidic device with a transparent material;
    fabricating a porous membrane between the top and bottom layer to form a cell growth compartment;
    etching a compartmentalized fluidic system to integrate flow of a fluidic material between the cell growth compartment; and
    creating a semi porous wall around the cell growth compartment to contain a growth media for a different type of cells to mimic the human body system.

2. The method of claim 1, further comprising:
    creating a multi-cell growth compartment with a combination of planar and vertical organization interfaced with a planar and a vertical porous barrier.

3. The method of claim 1, wherein the cell growth compartment is one of a parallel, horizontal, sequential in design in relation to each other.

4. The method of claim 1, wherein the compartmentalized fluidic system is organized in a planar and a vertical organization.

5. The method of claim 1, wherein the semi porous wall around the cell growth compartment has a specific structure for fluidic material to flow from one cell growth compartment to another.

6. The method of claim 4, wherein the specific structure has an array of small pores which are located in the upper side, lower side, middle and entire wall length of the semi porous wall.

7. The method of claim 1, further comprising:
monitoring a tissue integrity in real time in the cell growth compartment using a trans-epithelial electrical resistance device.

8. The method of claim 1, further comprising:
Controlling an inter-cell growth compartment flow of a nutrient, extracellular matrix fluid between two cell growth chambers using a set of an external pump.

9. The method of claim 1, wherein the modular microfluidic device prior to layering is fabricated using one of a silicon micromachining, soft lithography, injection molding, 2D printing, 3D printing and laser machining.

10. The method of claim 1, further comprising:
mapping of several tissues with a spatial and temporal architecture that emulate an in vivo human organ orientation for testing a drug effect.

11. A method of making a modular microfluidic device, comprising:
layering a top and a bottom layer of the modular microfluidic device with a transparent material;
fabricating a porous membrane between the top and bottom layer to form a cell growth compartment;
etching a compartmentalized fluidic system to integrate flow of a fluidic material between the cell growth compartment; and
creating a multi-cell growth compartment structure with a combination of planar and vertical organization and interfaced with a planar and a vertical porous barrier.

12. The method of claim 11, wherein the modular microfluidic device prior to layering is fabricated using one of a silicon micromachining, soft lithography, injection molding, 3D printing and laser machining.

13. The method of claim 11, further comprising:
creating a semi porous wall around the a cell growth compartment to contain a growth media for a different type of cells to mimic the human body system.

14. The method of claim 11, wherein the multi-a cell growth compartment structure is one of a linear order structure, parallel structure, honey comb structure and concentric structure.

15. The method of claim 13, wherein the semi porous wall is one of a straight, curved and meandering.

16. The method of claim 11, wherein the fluidic material flow is directed from a most outer compartment to a most inner one or vice versa.

17. The method of claim 13, wherein the semi porous wall has a pore size of 500 nm with a porosity of ~ 50% and a perfusion channel with width, height, and length of 3 μm, 10 μm and 50 μm.

18. A method of making a modular microfluidic device, comprising:
layering a top and a bottom layer of the modular microfluidic device with a transparent material;
fabricating a porous membrane between the top and bottom layer to form a cell growth compartment;
etching a compartmentalized fluidic system to integrate flow of a fluidic material between the cell growth compartment, wherein the compartmentalized fluidic system is one of a channel, a bridging channel or a combination of the channel and a bridging channel; and
creating a multi-cell growth compartment structure with a combination of planar and vertical organization and interfaced with a planar and a vertical porous barrier.

19. The method of claim 18, further comprising:
creating a semi porous wall around the cell growth compartment to contain a growth media for a different type of cells to mimic the human body system.

20. The method of claim 19, wherein the semi porous wall has a pore size of 500 nm with a porosity of ~ 50% and a perfusion channel with width, height, and length of 3 μm, 10 μm and 50 μm.

* * * * *